(12) United States Patent
Park et al.

(10) Patent No.: US 11,787,789 B2
(45) Date of Patent: Oct. 17, 2023

(54) COMPOUND FOR AN ORGANIC ELECTRIC ELEMENT, AN ORGANIC ELECTRIC ELEMENT USING THE SAME, AND AN ELECTRONIC DEVICE THEREOF

(71) Applicant: DUK SAN NEOLUX CO., LTD., Cheonan-si (KR)

(72) Inventors: Hyoung Keun Park, Cheonan-si (KR); Won Sam Kim, Cheonan-si (KR); Jung Hwan Park, Cheonan-si (KR); Hak Young Lee, Cheonan-si (KR); Min Ji Jo, Cheonan-si (KR)

(73) Assignee: DUK SAN NEOLUX CO., LTD., Cheonan-si (KR)

( * ) Notice: Subject to any disclaimer, the term of this patent is extended or adjusted under 35 U.S.C. 154(b) by 713 days.

(21) Appl. No.: 16/763,873

(22) PCT Filed: Oct. 12, 2018

(86) PCT No.: PCT/KR2018/012062
§ 371 (c)(1),
(2) Date: May 13, 2020

(87) PCT Pub. No.: WO2019/098535
PCT Pub. Date: May 23, 2019

(65) Prior Publication Data
US 2021/0171510 A1 Jun. 10, 2021

(30) Foreign Application Priority Data
Nov. 14, 2017 (KR) .................. 10-2017-0151604

(51) Int. Cl.
*C09K 11/06* (2006.01)
*C07D 413/04* (2006.01)
(Continued)

(52) U.S. Cl.
CPC ......... *C07D 413/04* (2013.01); *C07D 403/04* (2013.01); *C07D 487/14* (2013.01);
(Continued)

(58) Field of Classification Search
CPC .............. C07D 413/04; H01L 51/0052; H01L 51/0067; H01L 51/0069; H01L 51/0072–0074
(Continued)

(56) References Cited

U.S. PATENT DOCUMENTS

2017/0288148 A1* 10/2017 Park .................... H01L 51/0067
2018/0337361 A1* 11/2018 Lee ..................... H01L 51/5036

FOREIGN PATENT DOCUMENTS

| KR | 10-2014-0101807 A | 8/2014 |
| KR | 10-2016-0142792 A | 12/2016 |

(Continued)

OTHER PUBLICATIONS

Machine translation of WO-2017138755, translation generated Jan. 2023, 15 pages. (Year: 2023).*

(Continued)

*Primary Examiner* — Robert S Loewe
(74) *Attorney, Agent, or Firm* — Vorys, Sater, Seymour and Pease LLP; Mih Suhn Koh

(57) ABSTRACT

The present invention provides the compound represented by Formula 1, an organic electric element comprising a first electrode, a second electrode, and an organic material layer formed between the first electrode and the second electrode, and electronic device thereof, and by comprising the compound represented by Formula 1 in the organic material layer, the driving voltage of the organic electric element can be lowered, and the luminous efficiency and life time of the organic electric element can be improved.

11 Claims, 1 Drawing Sheet

(51) Int. Cl.
- *C07D 403/04* (2006.01)
- *C07D 487/14* (2006.01)
- *H10K 85/60* (2023.01)
- *H10K 50/11* (2023.01)
- *H10K 50/15* (2023.01)
- *H10K 50/16* (2023.01)
- *H10K 50/17* (2023.01)
- *H10K 101/10* (2023.01)

(52) U.S. Cl.
CPC ............ *C09K 11/06* (2013.01); *H10K 85/615* (2023.02); *H10K 85/622* (2023.02); *H10K 85/654* (2023.02); *H10K 85/656* (2023.02); *H10K 85/6572* (2023.02); *H10K 85/6574* (2023.02); *H10K 85/6576* (2023.02); *H10K 50/11* (2023.02); *H10K 50/15* (2023.02); *H10K 50/16* (2023.02); *H10K 50/171* (2023.02); *H10K 2101/10* (2023.02)

(58) Field of Classification Search
USPC .......................................................... 257/40
See application file for complete search history.

(56) References Cited

FOREIGN PATENT DOCUMENTS

| KR | 10-2017-0092128 A | | 8/2017 | |
|----|-------------------|---|--------|---|
| KR | 10-2017-0094767 A | | 8/2017 | |
| KR | 10-2017-0116983 A | | 10/2017 | |
| KR | 10-2018-0008336 A | | 1/2018 | |
| KR | 20180008336 A | * | 1/2018 | ........... C07D 487/14 |

OTHER PUBLICATIONS

Machine translation of KR-20180008336, translation generated Apr. 2023, 22 pages. (Year: 2023).*

* cited by examiner

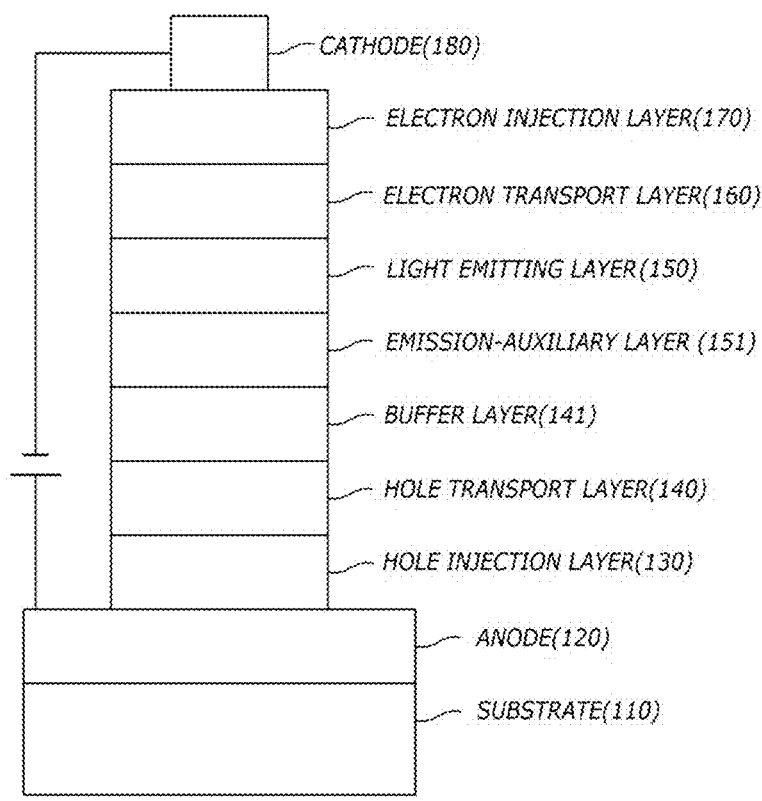

COMPOUND FOR AN ORGANIC ELECTRIC ELEMENT, AN ORGANIC ELECTRIC ELEMENT USING THE SAME, AND AN ELECTRONIC DEVICE THEREOF

CROSS-REFERENCE TO RELATED APPLICATION

This patent application claims priority from and the benefit under 35 U.S.C. § 119 to § 121, and § 365 of Korean Patent Application No. 10-2017-0151604, filed on Nov. 14, 2017 which is hereby incorporated by reference for all purposes as if fully set forth herein. Further, this application claims the benefit of priority in countries other than U.S., which is hereby incorporated by reference herein.

BACKGROUND

Technical Field

The present invention relates to compound for an organic electric element, an organic electric element comprising the same, and an electronic device thereof.

Background Art

In general, an organic light emitting phenomenon refers to a phenomenon in which electric energy is converted into light energy of an organic material. An organic electric element utilizing the organic light emitting phenomenon usually has a structure including an anode, a cathode, and an organic material layer interposed therebetween. In many cases, the organic material layer has a multi-layered structure having respectively different materials in order to improve efficiency and stability of an organic electric element, and for example, may include a hole injection layer, a hole transport layer, a light emitting layer, an electron transport layer, an electron injection layer, or the like.

Materials used as an organic material layer in an organic electric element may be classified into a light emitting material and a charge transport material, for example, a hole injection material, a hole transport material, an electron transport material, an electron injection material, and the like according to its function. Further, the light emitting material may be divided into a high molecular weight type and a low molecular weight type according to its molecular weight, and may also be divided into a fluorescent material derived from excited singlet states of electron and a phosphorescent material derived from excited triplet states of electron according to its light emitting mechanism. Further, the light emitting material may be divided into blue, green, and red light emitting material and yellow and orange light emitting material required for better natural color reproduction according to its light emitting color.

Meanwhile, when only one material is used as a light emitting material, there occur problems of shift of a maximum luminescence wavelength to a longer wavelength due to intermolecular interactions and lowering of the efficiency of a corresponding element due to a deterioration in color purity or a reduction in luminous efficiency. On account of this, a host/dopant system may be used as the light emitting material in order to enhance the color purity and increase the luminous efficiency through energy transfer. This is based on the principle that if a small amount of dopant having a smaller energy band gap than a host forming a light emitting layer is mixed in the light emitting layer, then excitons generated in the light emitting layer are transported to the dopant, thus emitting light with high efficiency. With regard to this, since the wavelength of the host is shifted to the wavelength band of the dopant, light having a desired wavelength can be obtained according the type of the dopant.

Currently, the power consumption is required more than more as size of display becomes larger and larger in the portable display market. Therefore, the power consumption is a very important factor in the portable display with a limited power source of the battery, and efficiency and life span issue also is solved.

Efficiency, life span, driving voltage, and the like are correlated with each other. For example, if efficiency is increased, then driving voltage is relatively lowered, and the crystallization of an organic material due to Joule heating generated during operation is reduced as driving voltage is lowered, as a result of which life span shows a tendency to increase. However, efficiency cannot be maximized only by simply improving the organic material layer. This is because long life span and high efficiency can be simultaneously achieved when an optimal combination of energy levels and Ti values, inherent material properties (mobility, interfacial properties, etc.), and the like among the respective layers included in the organic material layer is given.

Therefore, there is a need to develop a light emitting material that has high thermal stability and can efficiently a charge balance in the light-emitting layer. That is, in order to allow an organic electric element to fully exhibit excellent features, it should be prerequisite to support a material constituting an organic material layer in the element, for example, a hole injection material, a hole transport material, a light emitting material, an electron transport material, an electron injection material, or the like, by a stable and efficient material. However, the stable and efficient material of organic material layer for an organic electronic element has not been fully developed yet, in particular, it is strongly required to develop host material of the light emitting layer.

Object, Technical Solution and Effects of the Invention

The present invention is to provide a compound lowering a driving voltage, improving luminous efficiency and lifetime of the element, an organic electric element comprising the same, and an electronic device thereof.

In an aspect of the present invention, the present invention provides the compound represented by the following formula.

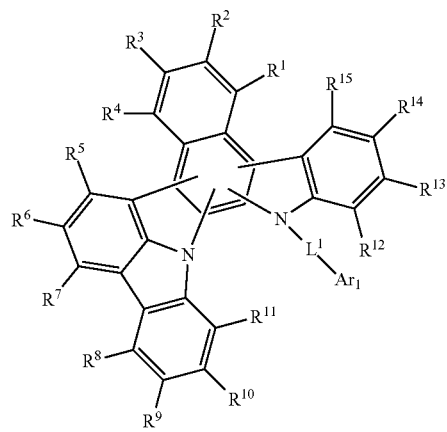

In another aspect of the present invention, the present invention provides an organic electric element using the compound represented by formula above and an electric device thereof.

By using the compound according to embodiment of the present invention, a driving voltage of element can be lowered and the luminous efficiency and lifetime of the element can be significantly improved.

BRIEF DESCRIPTION OF THE DRAWINGS

FIGURE illustrate an example of an organic electroluminescent element according to the present invention: 100 is an organic electric element, 110 is a substrate, 120 is a first electrode, 130 is a hole injection layer, 140 is a hole transport layer, 141 is a buffer layer, 150 is a light emitting layer, 151 is an emission-auxiliary layer, 160 is an electron transport layer, 170 is an electron injection layer, and 180 is a second electrode.

DETAILED DESCRIPTION

Unless otherwise stated, the term "aryl group" or "arylene group" as used herein has, but not limited to, 6 to 60 carbon atoms. The aryl group or arylene group in the present invention may comprise a monocyclic ring, ring assemblies, a fused polycyclic system, spiro compounds and the like.

The term "heterocyclic group" as used herein means a non-aromatic ring as well as an aromatic ring like "heteroaryl group" or "heteroarylene group", and unless otherwise stated, it means a ring comprising one or more heteroatoms and having 2 to 60 carbon atoms, but not limited thereto. Unless otherwise stated, the term "hetero atom" as used herein represents N, O, S, P or Si, and the heterocyclic group means a monocyclic form, ring assemblies, a fused polycyclic system or a spiro compound comprising heteroatom.

In addition, "heterocyclic group" means a ring comprising a heteroatom such as N, O, S, P, Si and so on instead of carbon forming a ring, it comprises a non-aromatic ring as well as an aromatic ring like "heteroaryl group" or "heteroarylene group", and it comprises the compound comprising a heteroatom group such as $SO_2$, $P=O$ etc. instead of carbon forming a ring such as the following compound.

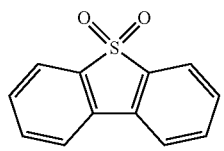 [SMILES: O=S1(=O)c2ccccc2-c2ccccc21]

Unless otherwise stated, the term "fluorenyl group" or "fluorenylene group" as used herein means univalent or bivalent functional group in which R, R' and R" are all hydrogen in the following structure, "substituted fluorenyl group" or "substituted fluorenylene group" means that at least any one of R, R' and R" is a substituent other than hydrogen, and it comprises the case where R and R' are bonded to each other to form the spiro compound together with the carbon to which they are bonded.

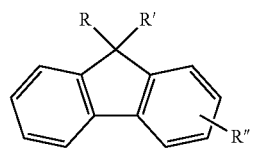

The term "spiro compound" as used herein has, a spiro union which means union having one atom as the only common member of two rings. The common atom is designated as 'spiro atom'. The compounds are defined as 'monospiro', 'dispiro' or 'trispiro' depending on the number of spiro atoms in one compound.

In this specification, a 'group name' corresponding to an aryl group, an arylene group, a heterocyclic group, and the like exemplified for each symbol and its substituent may be written in the name of functional group reflecting the valence, and may also be described as the name of a parent compound. For example, in the case of phenanthrene which is a kind of aryl group, it may be described by distinguishing valence such as 'phenanthryl (group)' when it is 'monovalent group', and as 'phenanthrylene (group)' when it is 'divalent group', and it may also be described as a parent compound name, 'phenanthrene', regardless of its valence. Similarly, in the case of pyrimidine, it may be described as 'pyrimidine' regardless of its valence, and it may also be described as the name of corresponding functional group such as pyrimidinyl (group) when it is 'monovalent group', and as 'pyrimidylene (group)' when it is 'divalent group'.

In addition, otherwise specified, the formulas used in the present invention are as defined in the index definition of the substituent of the following formula.

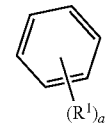

Here, when a is an integer of zero, the substituent $R^1$ is absent, when a is an integer of 1, $R^1$ is linked to any one of the carbon atoms constituting the benzene ring, when a is an integer of 2 or 3, the substituent $R^1$s are linked to the benzene ring as follows and the substituent $R^1$s may be the same and different. When a is an integer of 4 to 6, the substituents $R^1$s are linked to the benzene ring in a similar manner to that when a is an integer of 2 or 3, hydrogen linked to carbon constituents of the benzene ring may be omitted.

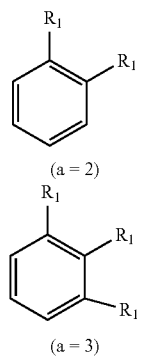

Hereinafter, a laminated structure of the electric element comprising the compound of the present invention will be described with reference to FIGURE.

In the following description of the present invention, a detailed description of known functions and configurations incorporated herein will be omitted when it may make the subject matter of the present invention rather unclear.

In addition, it will be understood that when an element such as a layer, film, region or substrate is referred to as being "on" or "over" another element, it can be directly on the other element or intervening elements may also be present. In contrast, when an element is referred to as being "directly on" another element, there are no intervening elements present.

The Figures shows an example of an organic electric element according to an embodiment of the present invention.

Referring to the FIGURE, an organic electric element 100 according to an embodiment of the present invention includes a first electrode 120 formed on a substrate 110, a second electrode 180, and an organic material layer formed between the first electrode 120 and the second electrode 180 and comprising the compound of the present invention. Here, the first electrode 120 may be an anode (positive electrode), and the second electrode 180 may be a cathode (negative electrode). In the case of an inverted organic electroluminescent element, the first electrode may be a cathode, and the second electrode may be an anode.

The organic material layer may include a hole injection layer 130, a hole transport layer 140, a light emitting layer 150, an electron transport layer 160, and an electron injection layer 170 formed in sequence on the first electrode 120. Here, at least one layer of the organic material layer may be omitted, or the organic material layer may further include a hole blocking layer, an electron blocking layer, an emission-auxiliary layer 151, a buffer layer 141, etc., and the electron transport layer 160 or the like may serve as a hole blocking layer.

In addition, although not shown, the organic electric element according to an embodiment of the present invention may further include a protective layer or a layer for improving luminous efficiency formed on at least one side of sides of the first electrode and the second electrode, wherein at least one side is not facing the organic material layer.

The inventive compound employed in the organic material layer may be used as a material of a hole injection layer 130, a hole transport layer 140, electron transport layer 160, an electron injection layer 170, a light emitting layer 150, a layer for improving luminous efficiency, an emission-auxiliary layer and so on. For example, the inventive compound may be used as material of a light emitting layer 150, preferably, as host material of a light emitting layer.

The organic electric element according to an embodiment of the present invention may be manufactured using various deposition methods. The organic electric element according to an embodiment of the present invention may be manufactured using a PVD (physical vapor deposition) method or CVD (chemical vapor deposition) method. For example, the organic electric element may be manufactured by depositing a metal, a conductive metal oxide, or a mixture thereof on the substrate to form the anode 120, forming the organic material layer including the hole injection layer 130, the hole transport layer 140, the light emitting layer 150, the electron transport layer 160, and the electron injection layer 170 thereon, and then depositing a material, which can be used as the cathode 180, thereon. Also, an emitting auxiliary layer 151 may be formed between a hole transport layer 140 and a light emitting layer 150.

Also, the organic material layer may be manufactured in such a manner that a smaller number of layers are formed using various polymer materials by a soluble process or solvent process, for example, spin coating, nozzle printing, inkjet printing, slot coating, dip coating, roll-to-roll, doctor blading, screen printing, or thermal transfer, instead of deposition. Since the organic material layer according to the present invention may be formed in various ways, the scope of protection of the present invention is not limited by a method of forming the organic material layer.

The organic electric element according to the present invention may be any one of an organic light emitting diode, an organic solar cell, an organic photo conductor, an organic transistor, an element for monochromatic or white illumination and an element quantum dot display.

Another embodiment of the present invention provides an electronic device including a display device which includes the above described organic electric element, and a control unit for controlling the display device. Here, the electronic device may be a wired/wireless communication terminal which is currently used or will be used in the future, and covers all kinds of electronic devices including a mobile communication terminal such as a cellular phone, a personal digital assistant (PDA), an electric dictionary, a point-to-multipoint (PMP), a remote controller, a navigation unit, a game player, various kinds of TVs, and various kinds of computers, and the display device may comprise an electroluminescent display, a quantum dot display and so on.

Hereinafter, the compound according to an aspect of the present invention will be described.

The compound according to an aspect of the present invention is represented by Formula 1 below.

[Formula 1]

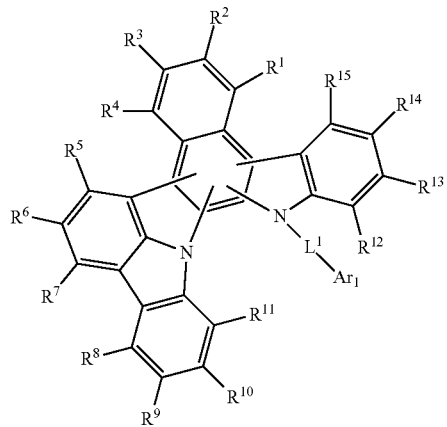

In the formula 1, each of symbols may be defined as follows.

$R^1$ to $R^{15}$ may be each independently selected from the group consisting of hydrogen, deuterium, halogen, a $C_6$-$C_{60}$ aryl group, a fluorenyl group, a $C_2$-$C_{60}$ heterocyclic group containing at least one heteroatom of O, N, S, Si, and P, a $C_3$-$C_{60}$ aliphatic ring, a fused ring group formed by a $C_3$-$C_{60}$ aliphatic ring with a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group and a $C_6$-$C_{30}$ aryloxy group.

In addition, adjacent $R^1$ to $R^{15}$ together may be bonded to each other to form a ring. That is, adjacent $R^1$ and $R^2$, $R^2$ and $R^3$, $R^3$ and $R^4$, $R^5$ and $R^6$, $R^6$ and $R^7$, $R^8$ and $R^9$, $R^9$ and $R^{19}$, $R^{19}$ and $R^{11}$, $R^{12}$ and $R^{13}$, $R^{13}$ and $R^{14}$, or $R^{14}$ and $R^{15}$ may be bonded to each other to form a ring. Here, the ring formed by bonding between adjacent groups may be selected from the group consisting of a O6-O60 aromatic ring, a $C_2$-$C_{60}$ heterocycle, a $C_3$-$C_{60}$ aliphatic ring and a combination thereof.

Where $R^1$ to $R^{15}$ are an aryl group, the aryl group may be preferably a $C_6$-$C_{30}$ or $C_6$-$C_{20}$ aryl group, more preferably a $C_6$-$C_{12}$ aryl group, for example, phenyl, biphenyl, naphthyl and the like. Where $R^1$ to $R^{15}$ are a heterocyclic group, the heterocyclic group may be preferably a $C_2$-$C_{30}$ or $C_2$-$C_{20}$ heterocyclic group, more preferably a $C_2$-$C_{12}$ heterocyclic group, for example, pyridine, pyrimidine, triazine, carbazole, dibenzofuran, dibenzothiophene and the like. Where $R^1$ to $R^{15}$ are an alkyl group, the alkyl group may be preferably a $C_1$-$C_{10}$ alkyl group, more preferably, a $C_1$-$C_4$ alkyl group, for example, methyl, ethyl and the like.

Where $R^1$ to $R^{15}$ are bonded to adjacent groups to form an aromatic ring, preferably a $C_6$-$C_{30}$ aromatic ring, more preferably a $C_6$-O14 aromatic ring may be formed, for example, a ring such as benzene, naphthalene, phenanthrene, anthracene and the like may be formed.

$L^1$ may be selected from the group consisting of a single bond, a $C_6$-$C_{60}$ arylene group, a fluorenylene group, a $C_2$-$C_{60}$ heterocyclic group containing at least one heteroatom of O, N, S, Si, and P, a $C_3$-$C_{60}$ aliphatic ring, and a fused ring group formed by a $C_3$-$C_{60}$ aliphatic ring with a $C_6$-$C_{60}$ aromatic ring.

Where $L^1$ are an arylene group, the arylene group may be preferably a $C_6$-$C_{30}$ or $C_6$-$C_{20}$ arylene group, more preferably a $C_6$-$C_{12}$ arylene group, for example, phenylene, biphenyl, naphthalene and the like. Where $L^1$ are a heterocyclic group, the heterocyclic group may be preferably a $C_2$-$C_{30}$ or $C_2$-$C_{20}$ heterocyclic group, more preferably a $C_2$-$C_{16}$ heterocyclic group, for example, pyridine, pyrimidine, pyrazine, triazine, quinazoline, quinoxaline, indole, isoquinoline, benzimidazole, benzoquinazoline, benzoquinoxaline, dibenzoquinoxaline, carbazole, dibenzothiophene, dibenzofuran, benzothienopyrimidine, benzofuropyrimidine, phenoxazine, phenothiazine and the like.

$Ar_1$ may be selected from the group consisting of a $C_6$-$C_{60}$ aryl group, a fluorenyl group, a $C_2$-$C_{60}$ heterocyclic group containing at least one heteroatom of O, N, S, Si, and P, a $C_3$-$C_{60}$ aliphatic ring, a fused ring group formed by a $C_3$-$C_{60}$ aliphatic ring with a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxy group and -L'-N($R_a$)($R_b$).

Where $Ar_1$ are an aryl group, the aryl group may be preferably a $C_6$-$C_{30}$ or $C_6$-$C_{20}$ aryl group, more preferably a $C_6$-$C_{18}$ aryl group, for example, phenyl, biphenyl, naphthyl, phenanthrene, triphenylene, pyrene, chrysene, terphenyl, anthracene and the like. Where $Ar_1$ are a heterocyclic group, the heterocyclic group may be preferably a $C_2$-$C_{30}$ or $C_2$-$C_{20}$ heterocyclic group, more preferably a $C_2$-$C_{19}$ heterocyclic group, for example, pyridine, pyrimidine, pyrazine, triazine, benzimidazole, diphenylbenzoimidazole, quinoxaline, quinazoline, benzoquinazoline, isoquinoline, benzoquinoxaline, dibenzoquinoxaline, carbazole, phenylcarbazole, benzocarbazole, indole, phenylindole, imidazopyridine, dibenzothiophene, dibenzofuran, benzothienopyrimidine, benzofuropyrimidine, phenothiazine, phenylphenothiazine, phenoxazine, phenylphenoxazine, phenoxthine, dibenzodioxine and the like. Where $Ar_1$ are a fluorenyl group, the fluorenyl group may 9,9-dimethyl-9H-fluorene, 9,9-diphenyl-9H-fluorene, 9,9'-spyrobifluorene, methylphenylfluorene and the like.

$L'$ may be selected from the group consisting of a single bond, a $C_6$-$C_{60}$ arylene group, a fluorenylene group, a $C_2$-$C_{60}$ heterocyclic group containing at least one heteroatom of O, N, S, Si, and P, a $C_3$-$C_{60}$ aliphatic ring, and a fused ring group formed by a $C_3$-$C_{60}$ aliphatic ring with a $C_6$-$C_{60}$ aromatic ring.

$R_a$ and $R_b$ may be each independently selected from the group consisting of hydrogen, a $C_6$-$C_{60}$ aryl group, a fluorenyl group, a $C_2$-$C_{60}$ heterocyclic group containing at least one heteroatom of O, N, S, Si, and P, and a fused ring group formed by a $C_3$-$C_{60}$ aliphatic ring with a $C_6$-$C_{60}$ aromatic ring.

Preferably, when $L^1$ is a single bond, a $C_6$-$C_{20}$ arylene group or a $C_2$-$C_{20}$ heterocyclic group, $Ar_1$ may be a $C_6$-$C_{20}$ aryl group, a $C_2$-$C_{20}$ heterocyclic group, a fluorene or -L'-N($R_a$)($R_b$), more preferably, when $L^1$ is a single bond, a $C_6$-$C_{12}$ arylene group or a $C_2$-$C_{16}$ heterocyclic group, $Ar_1$ may be a $C_6$-$C_{18}$ aryl group, a $C_2$-$C_{19}$ heterocyclic group, a fluorene or -L'-N($R_a$)($R_b$). For example, when $L^1$ is a single bond, phenylene, biphenyl, naphthalene, pyridine, pyrimidine, pyrazine, triazine, quinazoline, quinoxaline, indole, isoquinoline, benzimidazole, benzoquinazoline, benzoquinoxaline, dibenzoquinoxaline, carbazole, dibenzothiophene, dibenzofuran, benzothienopyrimidine, benzofuropyrimidine, phenoxazine, phenothiazine, etc., $A_n$ may be phenyl, biphenyl, naphthyl, phenanthrene, triphenylene, pyrene, chrysene, terphenyl, anthracene, pyridine, pyrimidine, pyrazine, triazine, benzimidazole, diphenylbenzoimidazole, quinoxaline, quinazoline, benzoquinazoline, isoquinoline, benzoquinoxaline, dibenzoquinoxaline, carbazole, phenylcarbazole, benzocarbazole, indole, phenylindole, imidazopyridine, dibenzothiophene, dibenzofuran, benzothienopyrimidine, benzofuropyrimidine, phenothiazine, phenylphenothiazine, phenoxazine, phenylphenoxazine, phenoxthine, dibenzodioxine, 9,9-dimethyl-9H-fluorene, 9,9-diphenyl-9H-fluorene, 9,9'-spyrobifluorene, methylphenylfluorene and the like.

In addition, preferably, when $R^1$ to $R^{15}$ are a $C_6$-$C_{20}$ aryl group, a $C_2$-$C_{20}$ heterocyclic group, a $C_1$-$C_{10}$ alkyl group or $R^1$ to $R^{15}$ are bonded to adjacent group to form a $C_6$-$C_{20}$ aromatic ring, $L^1$ may be a single bond, a $C_6$-$C_{20}$ arylene group or a $C_2$-$C_{20}$ heterocyclic group and $Ar_1$ may be a $C_6$-$C_{20}$ aryl group, a $C_2$-$C_{20}$ heterocyclic group, a fluorene or -L'-N($R_a$)($R_b$).

In addition, more preferably, when $R^1$ to $R^{15}$ are a $C_6$-$C_{12}$ aryl group, a $C_2$-$C_{12}$ heterocyclic group, a $C_1$-$C_4$ alkyl group or $R^1$ to $R^{15}$ are bonded to adjacent group to form a $C_6$-$C_{14}$ aromatic ring, $L^1$ may be a single bond, a $C_6$-$C_{12}$ arylene group or a $C_2$-$C_{16}$ heterocyclic group and $Ar_1$ may be a $C_6$-$C_{18}$ aryl group, a $C_2$-$C_{19}$ heterocyclic group, a fluorene or -L'-N($R_a$)($R_b$).

For example, $R^1$ to $R^{15}$ may be phenyl, biphenyl, naphthyl, pyridine, pyrimidine, triazine, carbazole, dibenzofuran, dibenzothiophene, methyl, ethyl and the like, $L^1$ may be a single bond, phenylene, biphenyl, naphthalene, pyridine, pyrimidine, pyrazine, triazine, quinazoline, quinoxaline, indole, isoquinoline, benzimidazole, benzoquinazoline, benzoquinoxaline, dibenzoquinoxaline, carbazole, dibenzothiophene, dibenzofuran, benzothienopyrimidine, benzofuropyrimidine, phenoxazine, phenothiazine and the like, and $Ar_1$ may be phenyl, biphenyl, naphthyl, phenanthrene, triphenylene, pyrene, chrysene, terphenyl, anthracene, pyridine, pyrimidine, pyrazine, triazine, benzimidazole, diphenylbenzoimidazole, quinoxaline, quinazoline, benzoquinazoline, isoquinoline, benzoquinoxaline, dibenzoquinoxaline, carbazole, phenylcarbazole, benzocarbazole, indole, phenylindole, imidazopyridine, dibenzothiophene, dibenzofuran, benzothienopyrimidine, benzofuropyrimidine, phenothiazine, phenylphenothiazine, phenoxazine, phenylphenoxazine, phenoxthine, dibenzodioxine, 9,9-dimethyl-9H-fluorene, 9,9-diphenyl-9H-fluorene, 9,9'-spyrobifluorene, methylphenylfluorene and the like.

The above $R^1$ to $R^{15}$, $L^1$, $Ar_1$, a ring formed by adjacent groups among $R^1$ to $R^{15}$, L', $R_a$ and $R_b$ may be each optionally substituted with one or more substituents selected from the group consisting of deuterium, halogen, a silane group unsubstituted or substituted with a $C_1$-$C_{20}$ alkyl group or a $C_6$-$C_{20}$ aryl group, a siloxane group, a boron group, a germanium group, a cyano group, a nitro group, a phosphine oxide group unsubstituted or substituted with a $C_1$-$C_{20}$ alkyl group or a $C_6$-$C_{20}$ aryl group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom of O, N, S, Si, and P, a $C_3$-$C_{20}$ cycloalkyl group, a fused ring group formed by a $C_3$-$C_{60}$ aliphatic ring with a $C_6$-$C_{60}$ aromatic ring, a $C_7$-$C_{20}$ arylalkyl group, a $C_8$-$C_{20}$ arylalkenyl group and -L'-N($R_a$)($R_b$).

For example, $R^1$ to $R^{15}$ may be further substituted with CN, and $Ar_1$ may be further substituted with one or more substituents selected from the group consisting of deuterium, a $C_1$-$C_4$ alkyl group, a $C_6$-$C_{14}$ aryl group, a $C_6$-$C_{16}$ aryl group substituted with deuterium, a fluorenyl group, and a $C_2$-$C_{18}$ heterocyclic group containing at least one heteroatom of O, N, S, Si, and P. For example, $Ar_1$ is may be further substituted with deuterium, t-butyl, phenyl, naphthyl, biphenyl, phenanthrene, pyrene, methylphenyl, fluorphenyl, phenyl substituted with CN, phenyl substituted with deuterium, quinazoline, dibenzothiophene, dibenzofuran, carbazole, phenylcarbazole, dimethylfluorene, and the like.

For example, Formula 1 may be represented by one of Formula 2 to Formula 5 below.

<Formula 2>

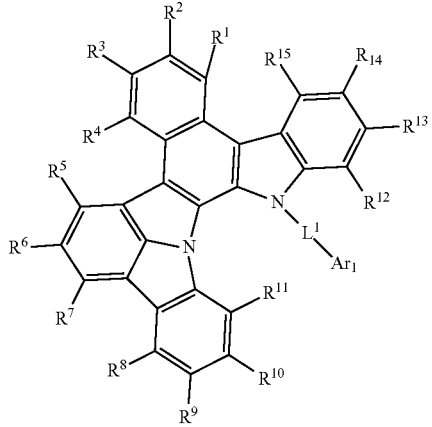

<Formula 3>

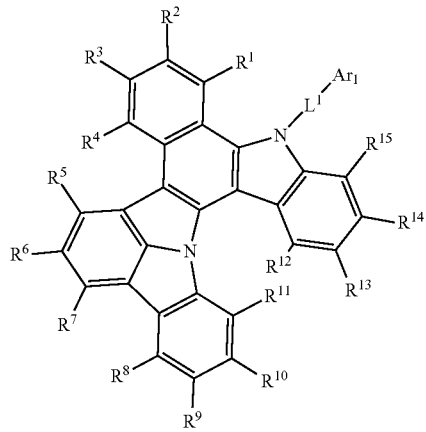

<Formula 4>

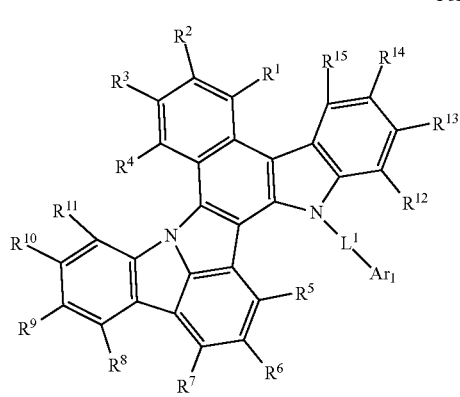

<Formula 5>

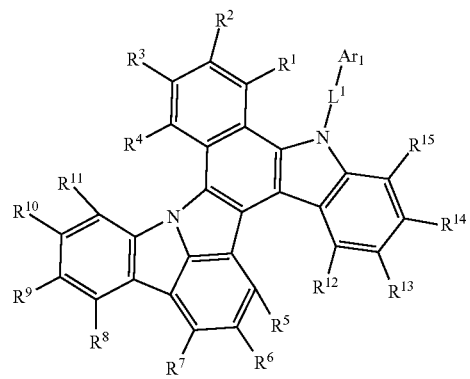

In Formulas 2 to 5, $R^1$ to $R^{15}$, $L^1$ and $Ar_1$ are the same as defined for Formula 1.

Specifically, the compound represented by formula 1 may be one of the following compounds.

P-1
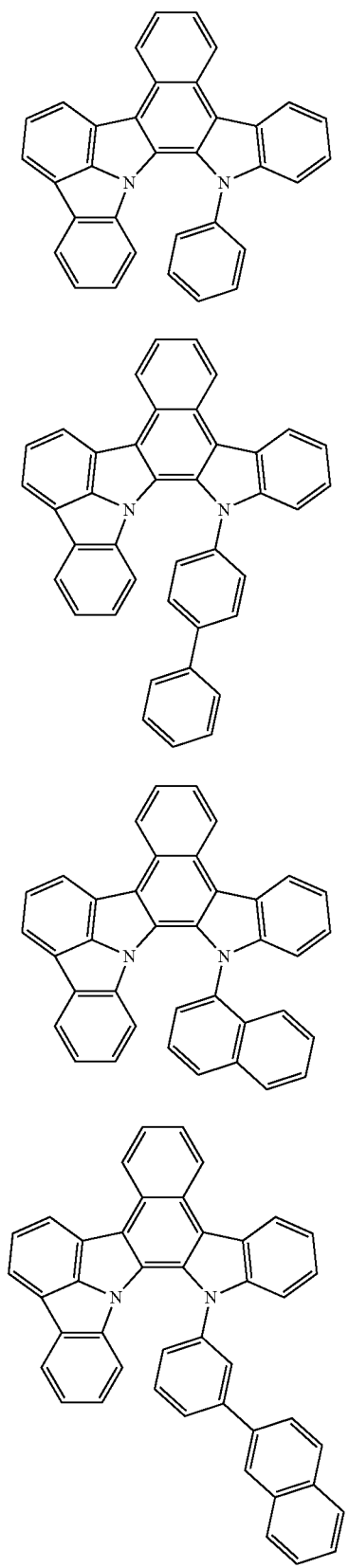
P-2
P-3
P-4
P-5
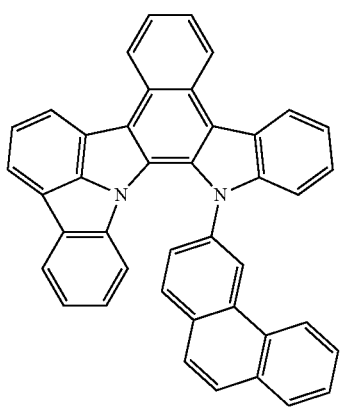
P-6
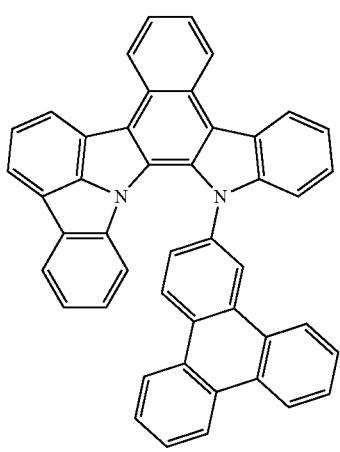
P-7
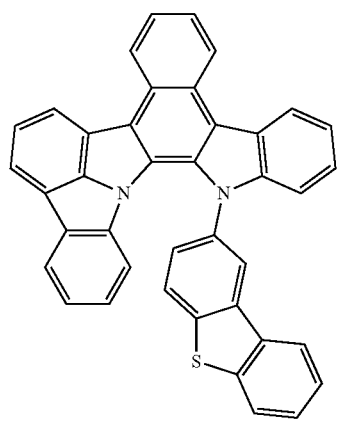

-continued
P-8
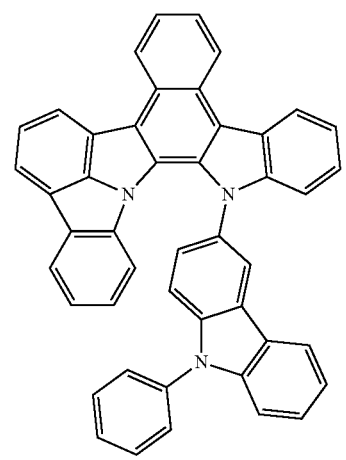
P-9
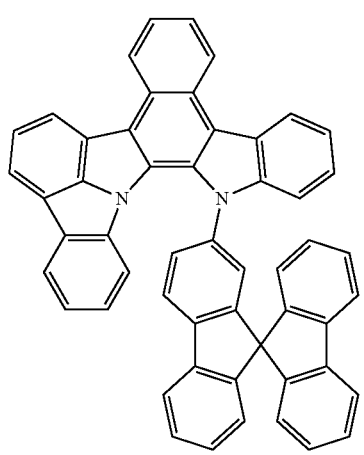
P-10
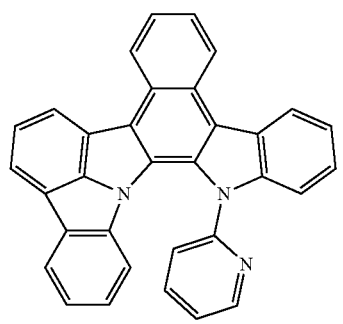
P-11
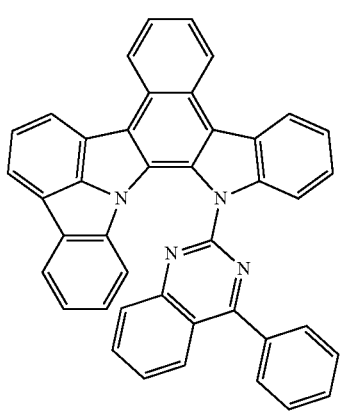
P-12
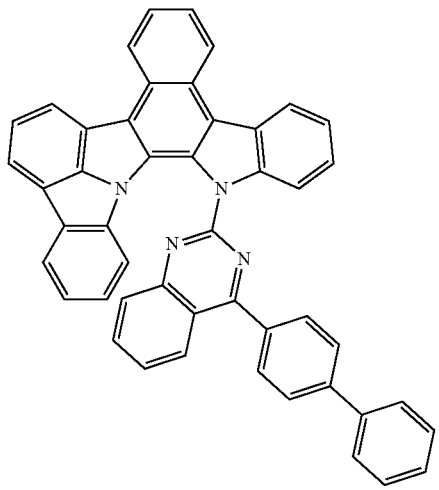
P-13
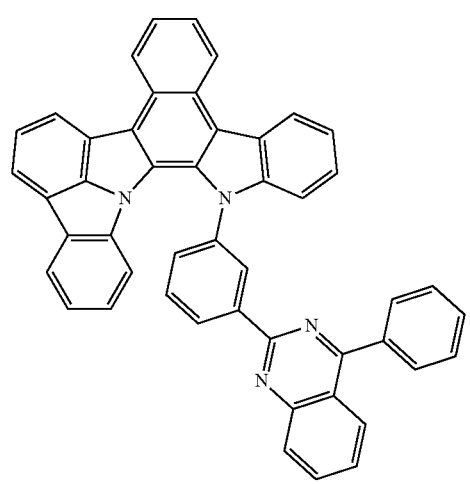
P-14
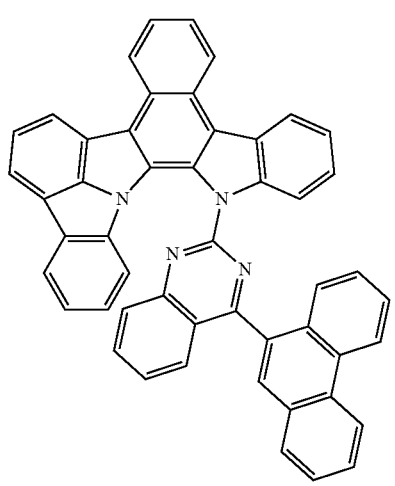

-continued
P-15
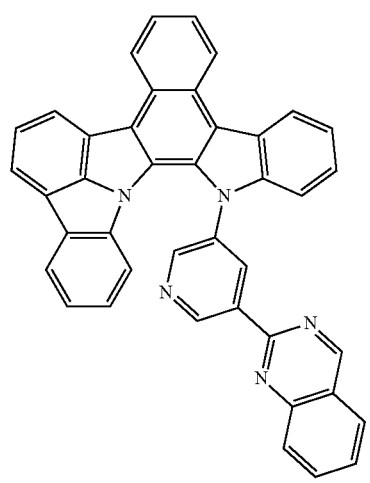
P-16
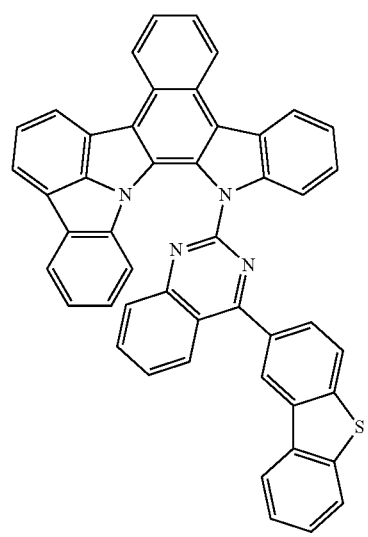
P-17
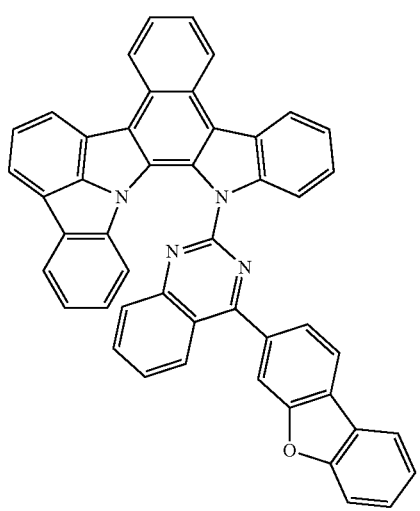
-continued
P-18
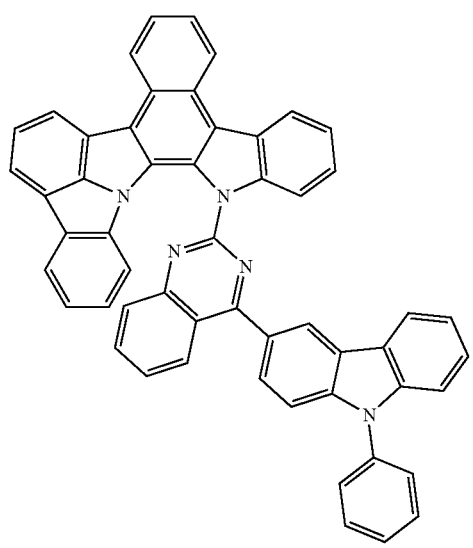
P-19
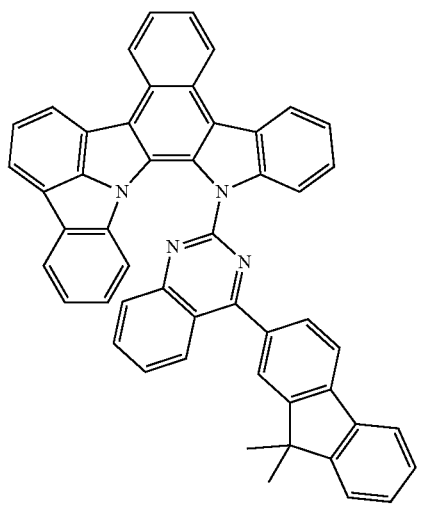
P-20
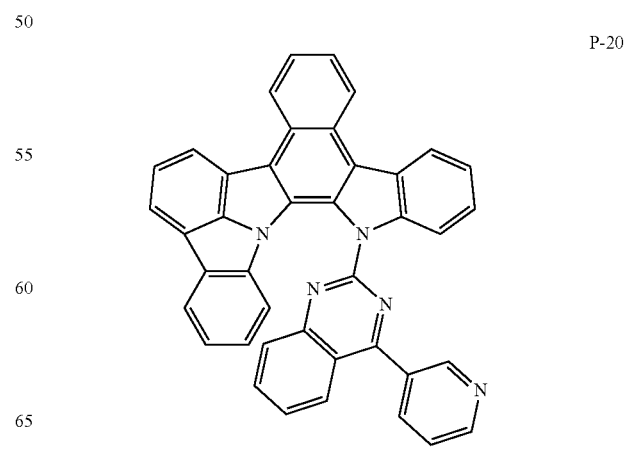

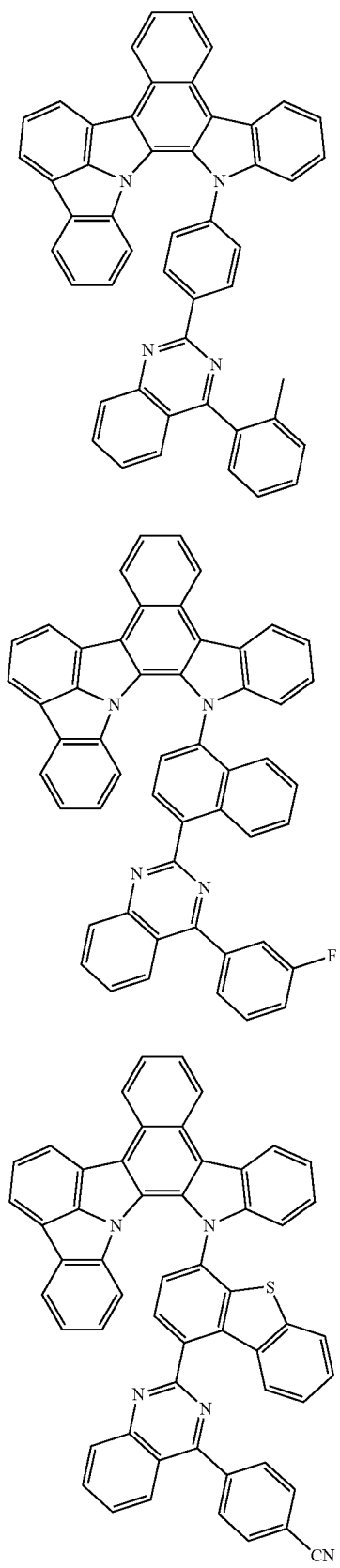
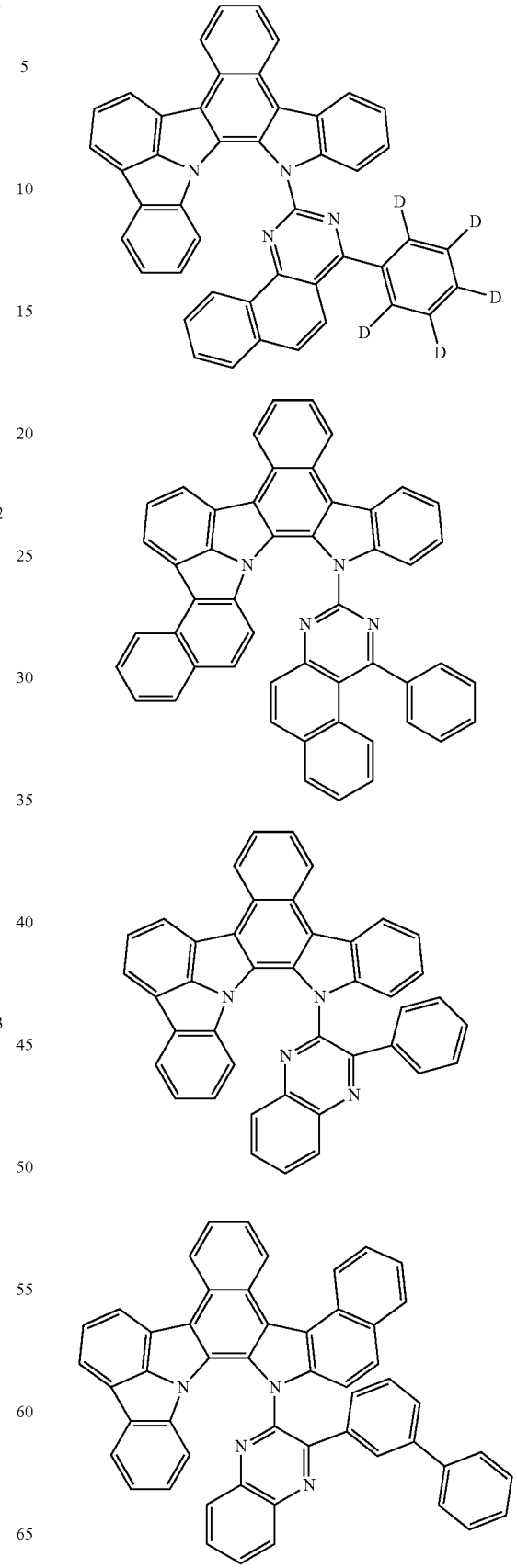

P-28
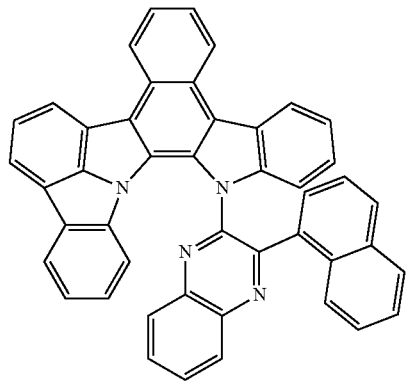
P-29
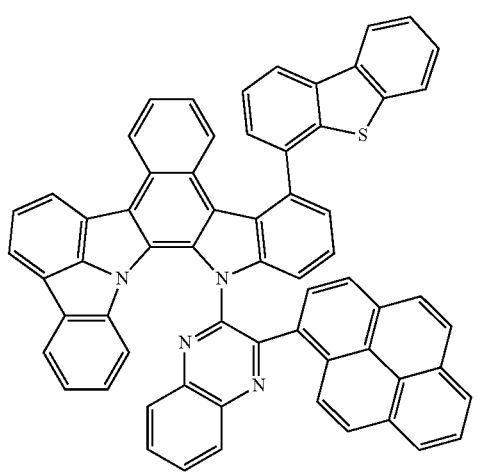
P-30
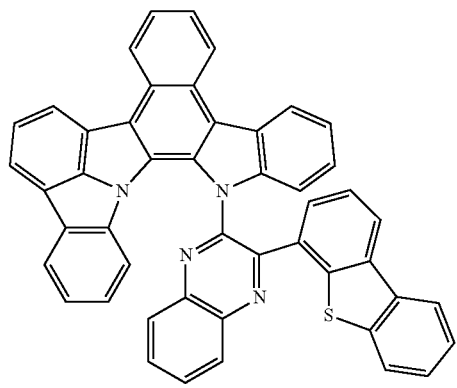
P-31
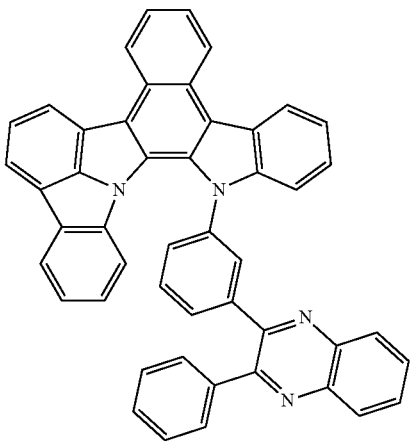
P-32
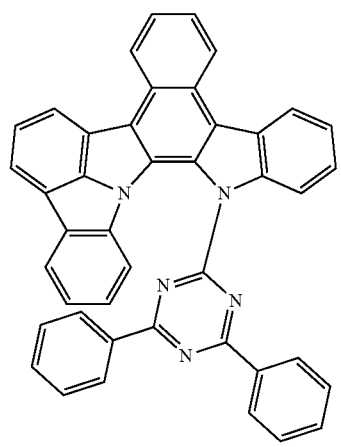
P-33
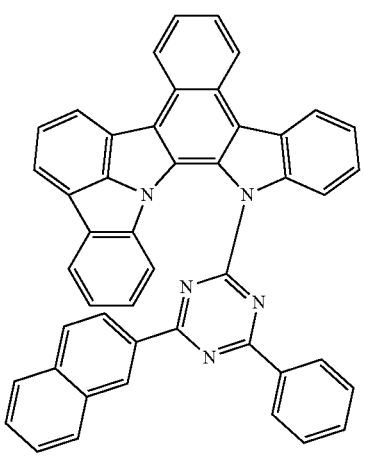

-continued
P-34
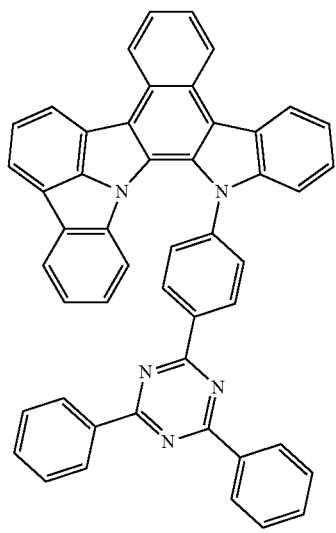
P-35
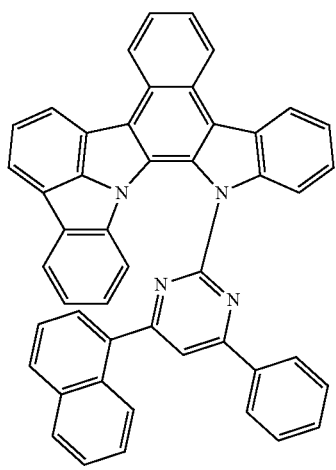
P-36
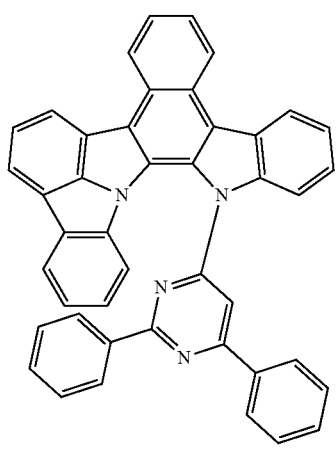
P-37
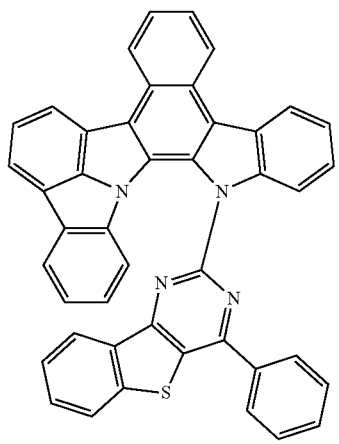
P-38
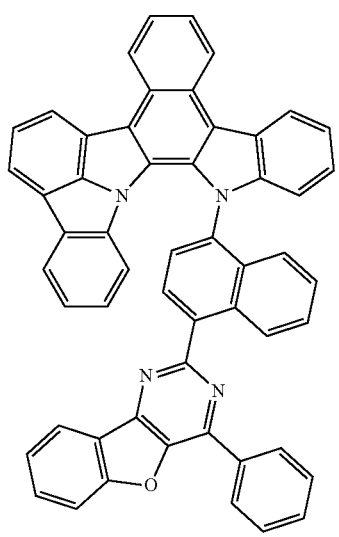
P-39
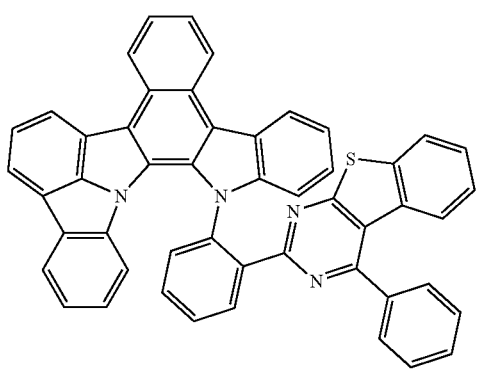

P-40
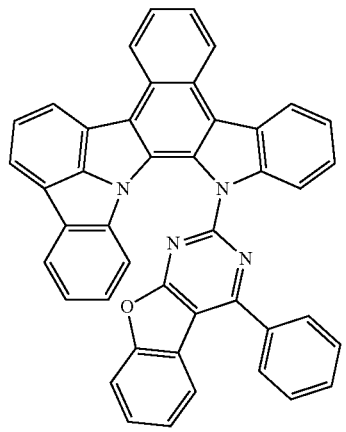
P-41
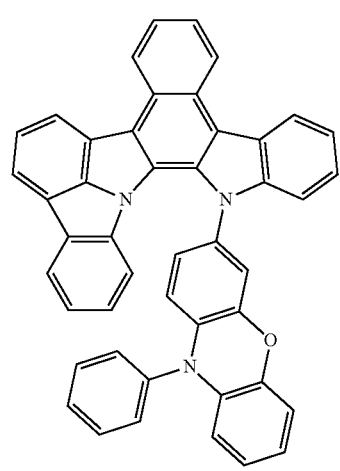
P-42
P-43
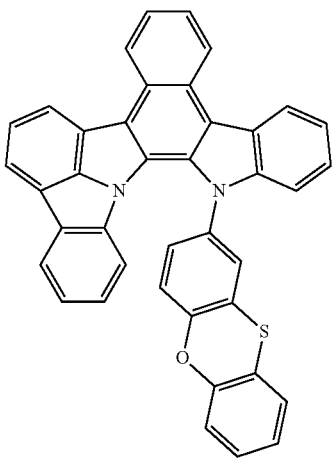
P-44
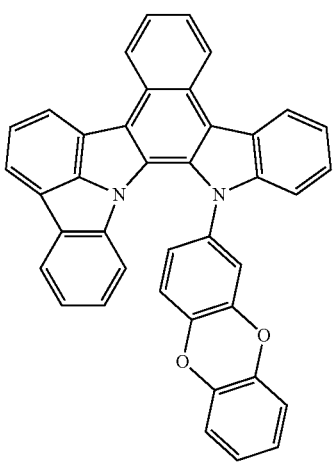
P-45
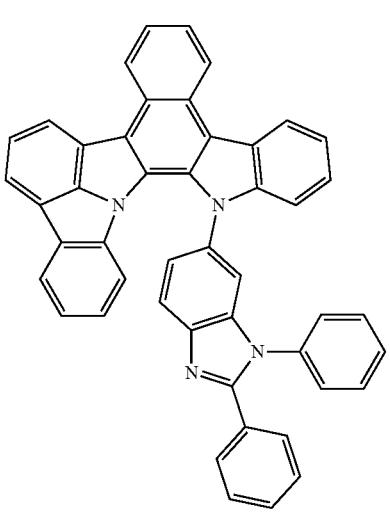

P-46
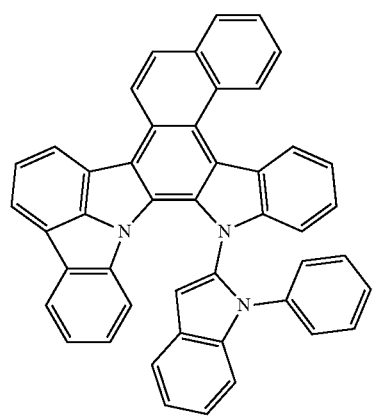
P-47
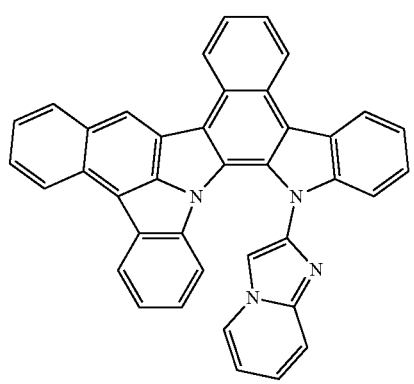
P-48
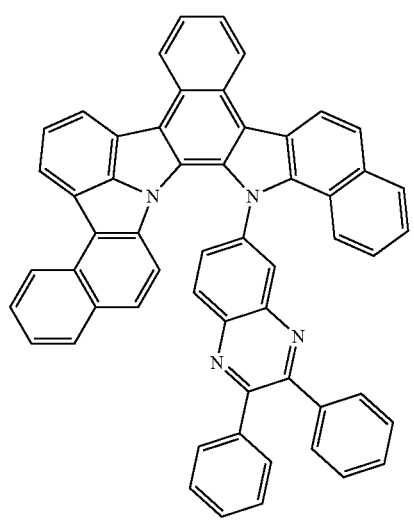
P-49
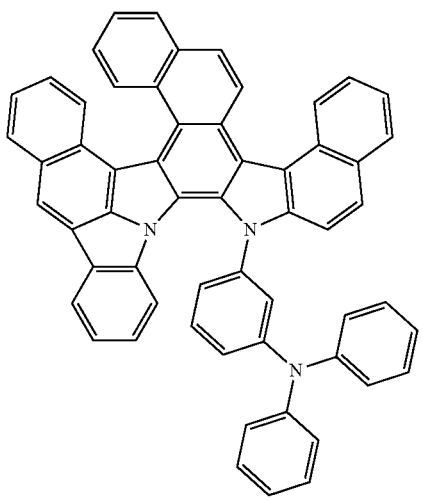
P-50
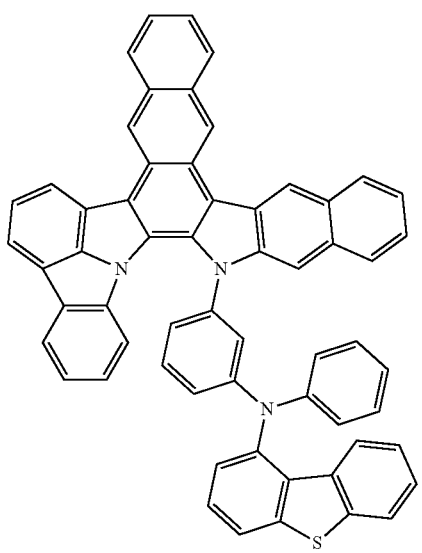
P-51
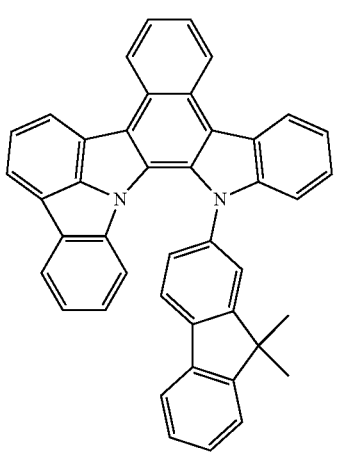

P-52
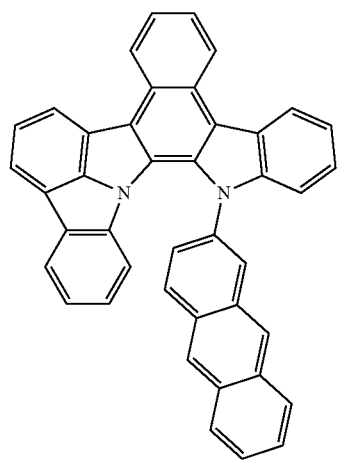
P-55
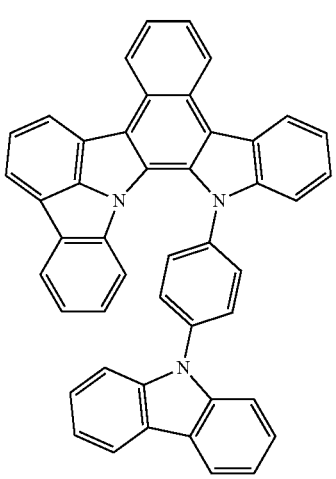
P-53
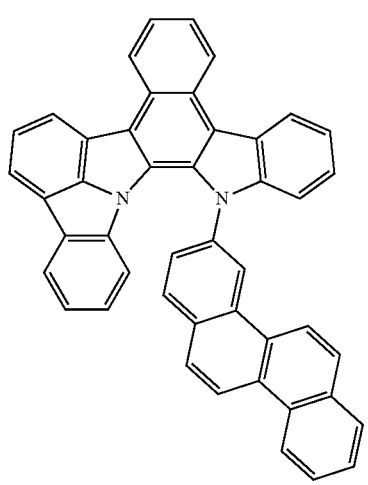
P-56
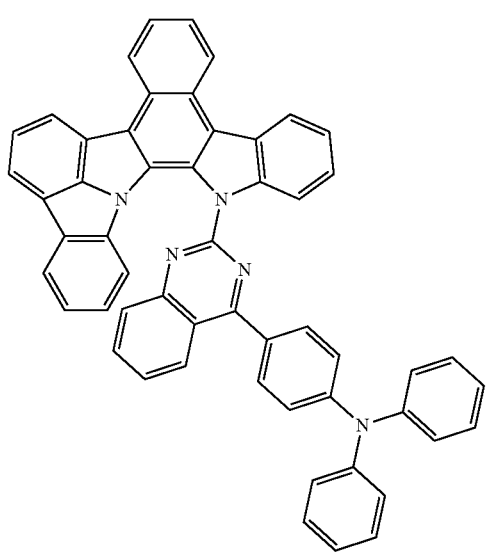
P-54
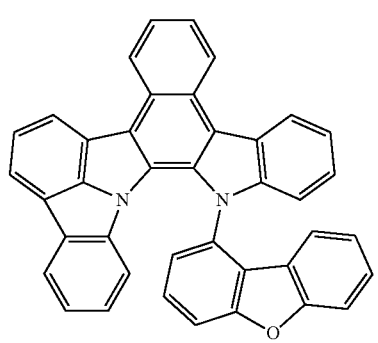
P-57
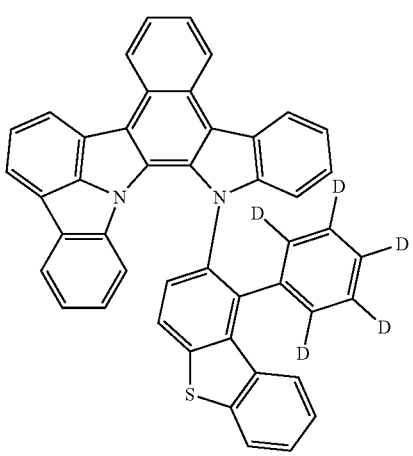

P-58
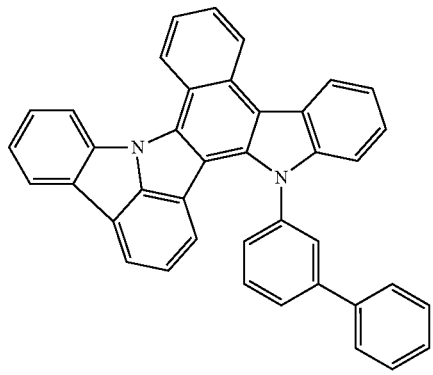
P-59
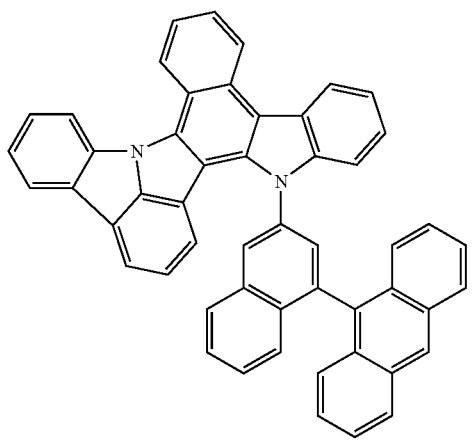
P-60
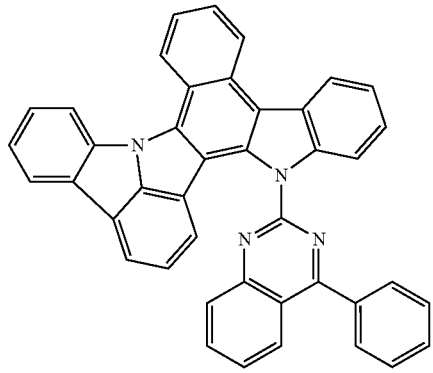
P-61
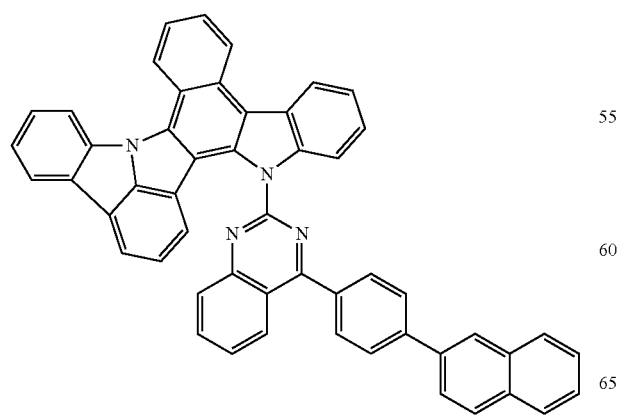
P-62
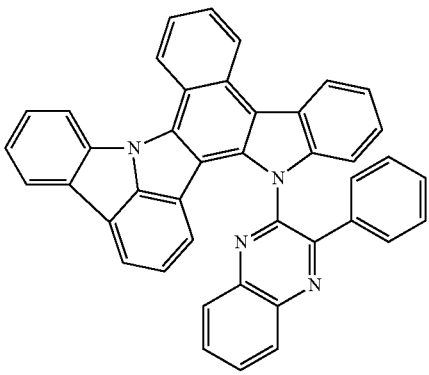
P-63
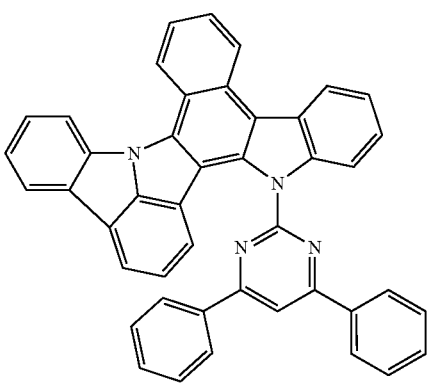
P-64
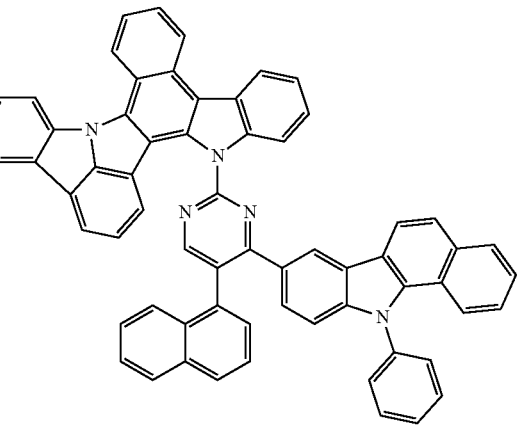
P-65
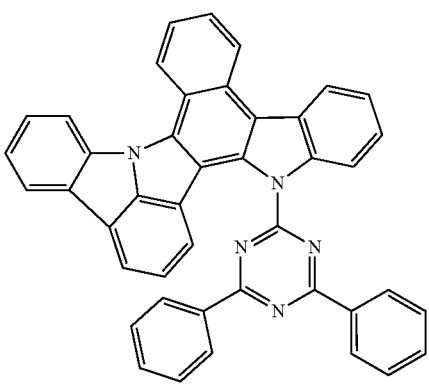

P-66
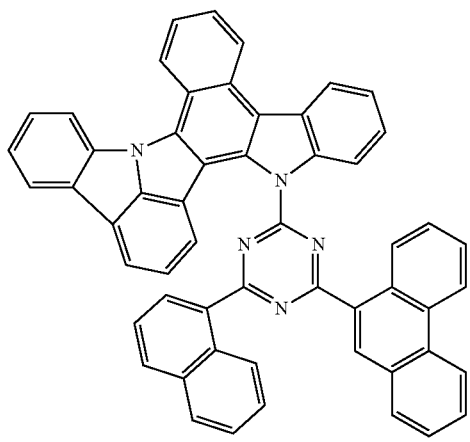
P-67
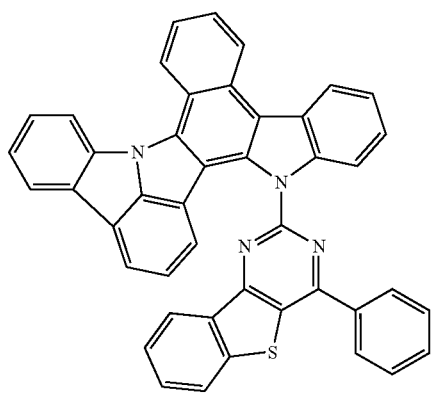
P-68
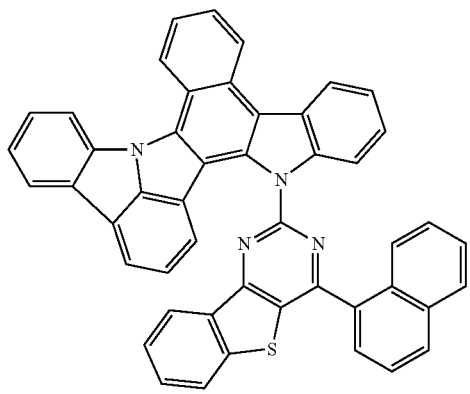
P-69
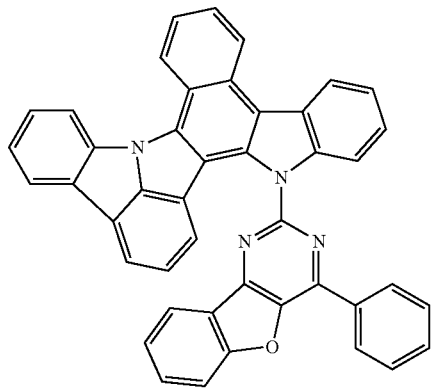
P-70
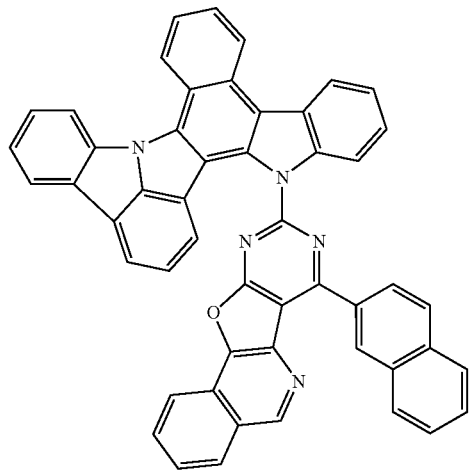
P-71
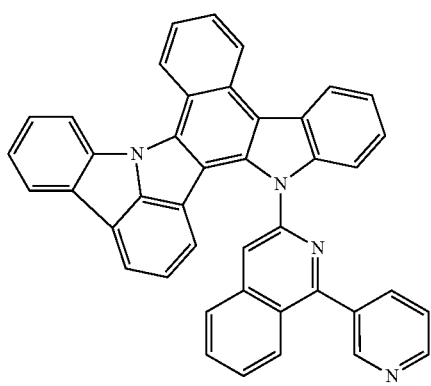
P72
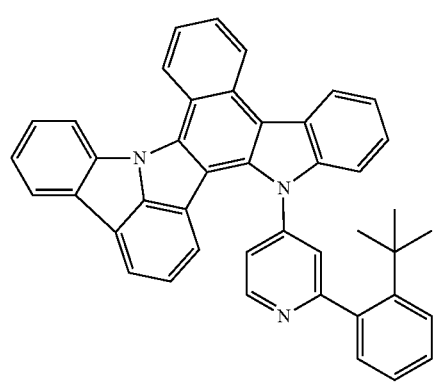
P73
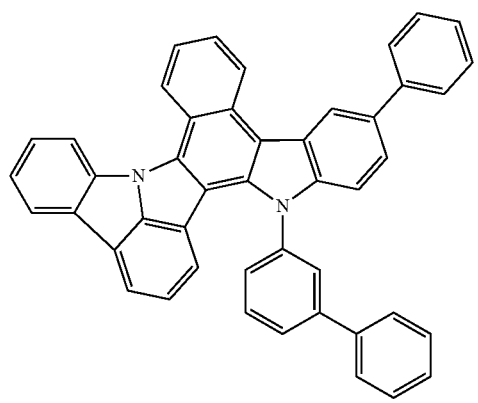

-continued
P-74
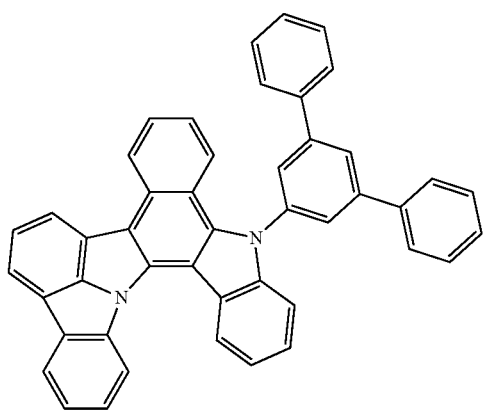
P-75
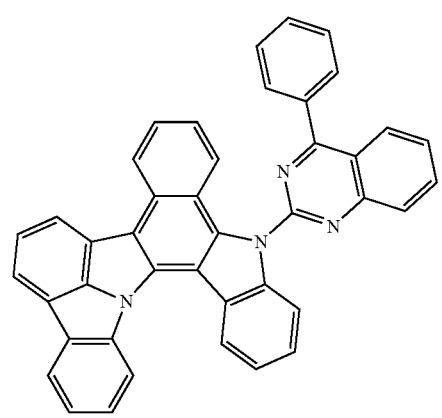
P-76
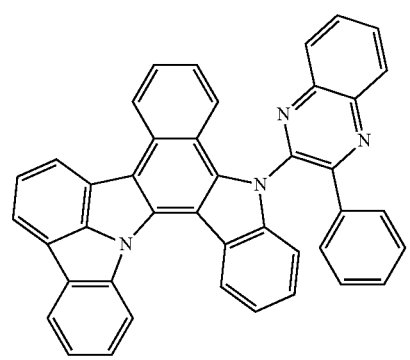
P-77
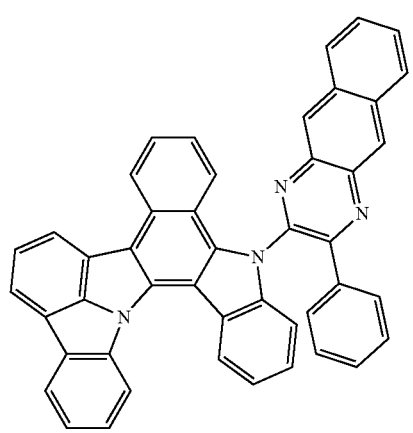
-continued
P-78
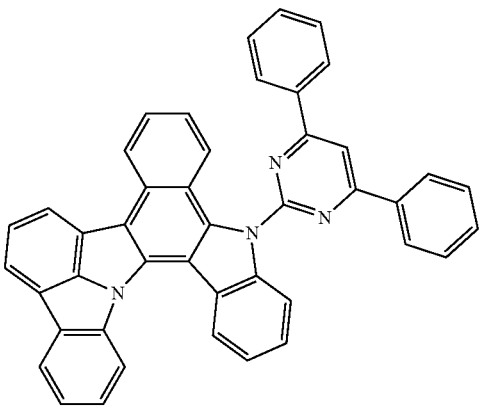
P-79
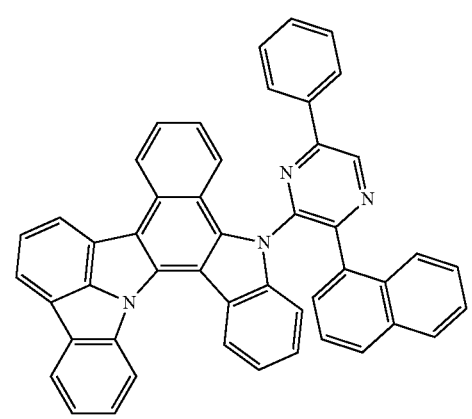
P-80
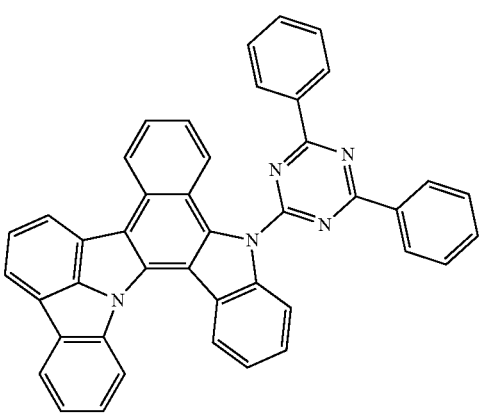
P-81
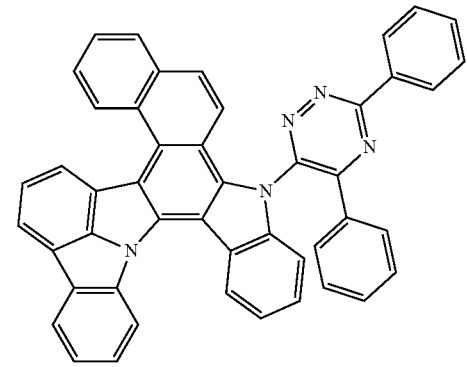

-continued
P-82
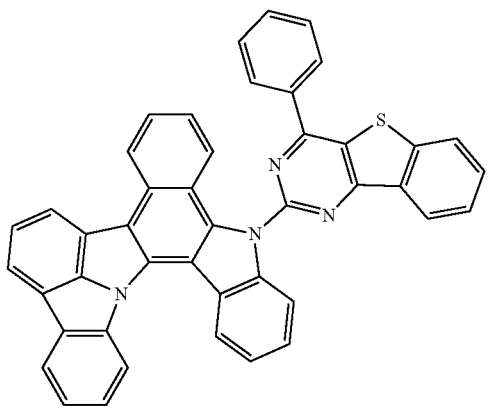
P-83
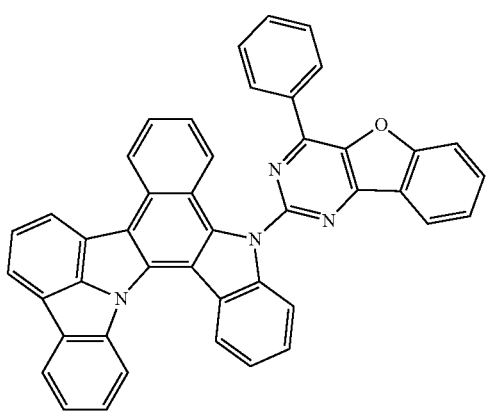
P-84
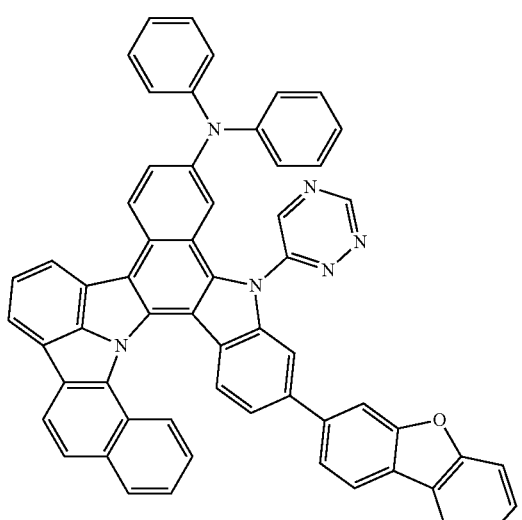
-continued
P-85
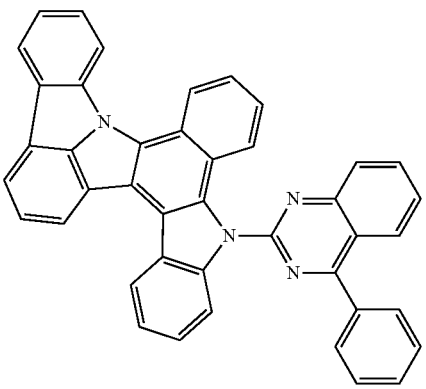
P-86
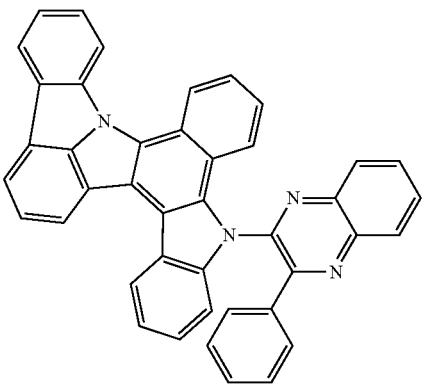
P-87
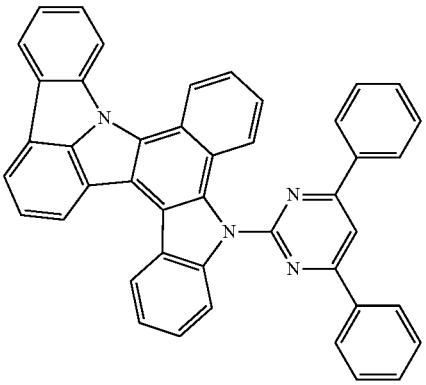
P-88
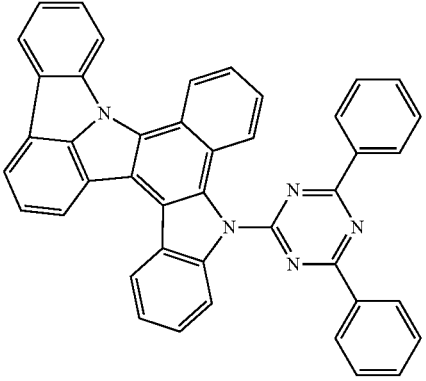

P-89
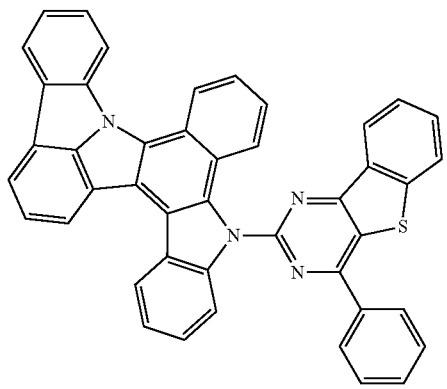

P-90
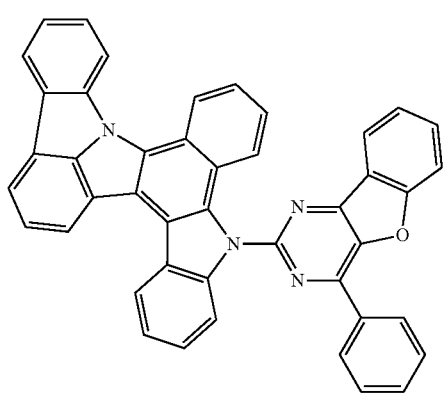

P-91
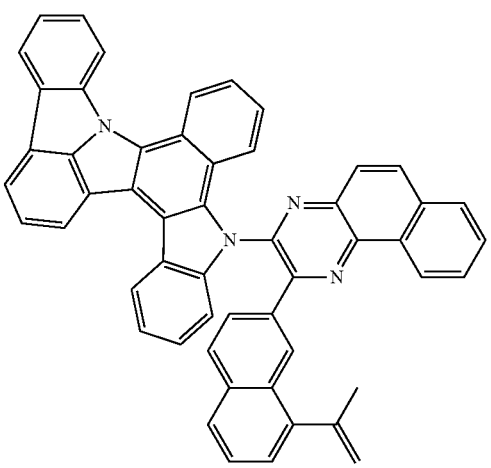

P-92
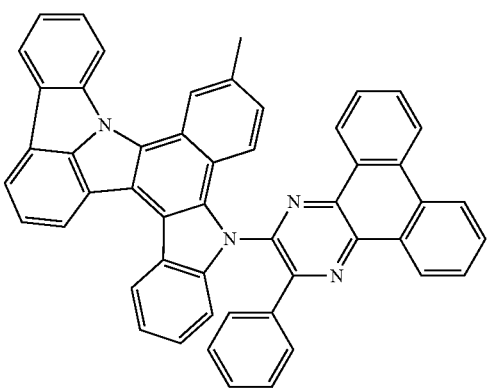

P-93
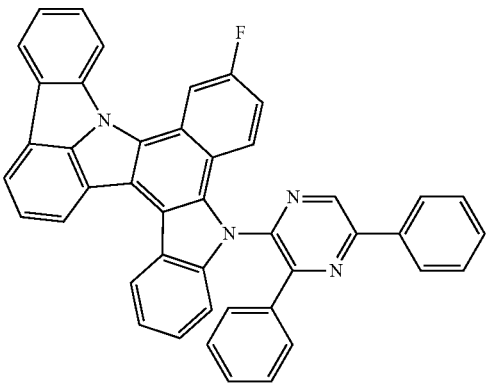

P-94
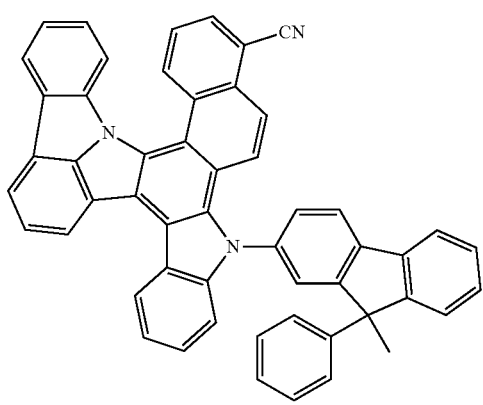

P-95
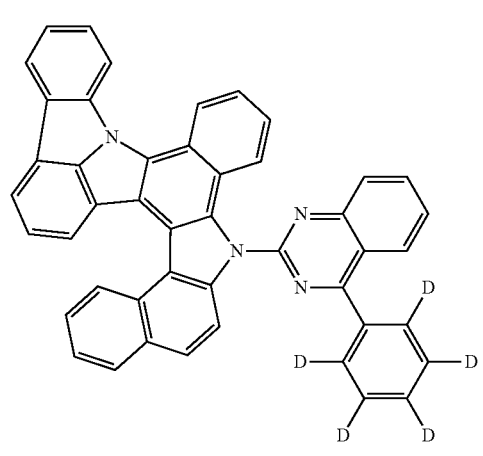

In an aspect of the present invention, the present invention provides an organic electric element comprising a first electrode, a second electrode, and an organic material layer formed between the first electrode and the second electrode, wherein the organic material layer comprises the compound represented by Formula 1 as a single compound or a mixture of two or more kinds.

The organic material layer comprises at least one of a hole injection layer, a hole transport layer, an emission-auxiliary layer, a light emitting layer, an electron transport auxiliary layer and an electron injection layer, preferably, the compound or the mixture is comprised in a light emitting layer.

In another aspect of the present invention, the present invention provides an electric device comprising a display device and a control unit for driving the display device, wherein the display device comprises the organic electric element.

Hereinafter, synthesis example of the compound represented by Formula and preparation method of an organic electric element according to one embodiment of the present invention will be described in detail by way of examples. However, the present invention is not limited to the following examples.

SYNTHESIS EXAMPLE

Synthesis Example 1

The compound represented by Formula 1 according to the present invention can be synthesized by reacting Core and Sub as shown in Reaction Scheme 1 below, but there is no limitation thereto. Here, Hal represents Br or $C_1$.

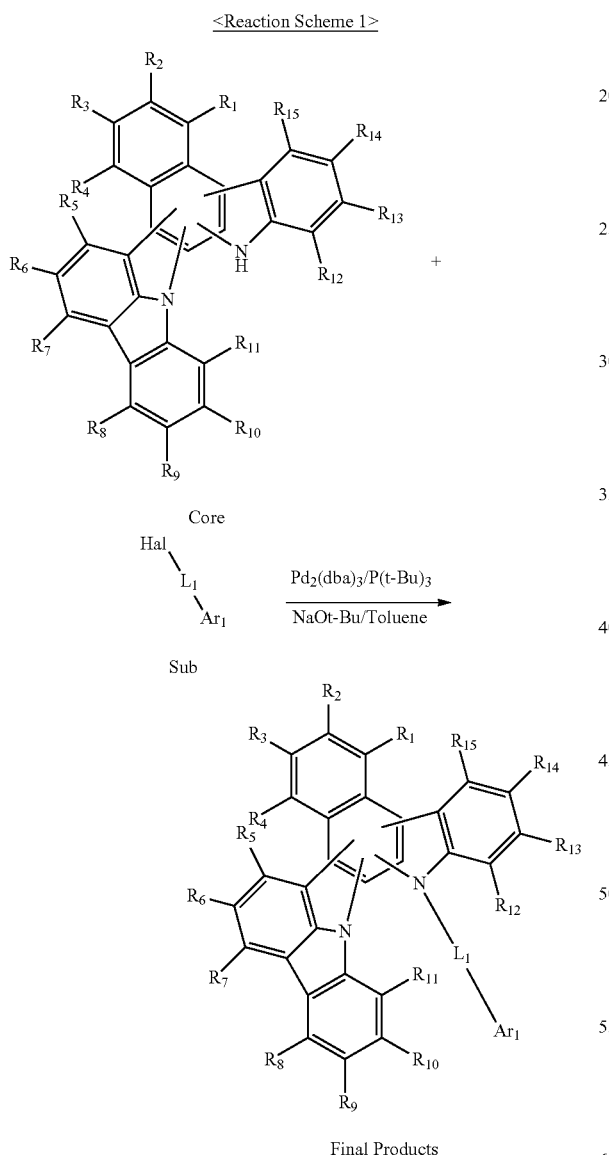

I. Synthesis Example of Core

The compound belonging to Core of the Reaction Scheme 1 may be synthesized by the following Reaction Scheme 2, but there is no limitation thereto.

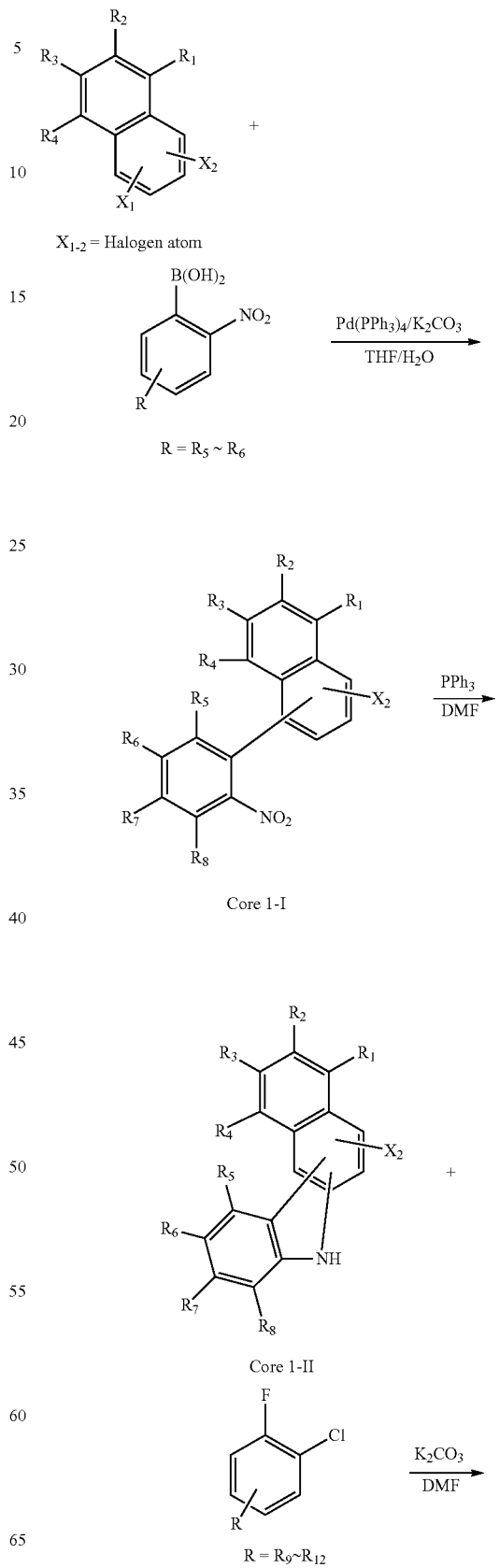

-continued

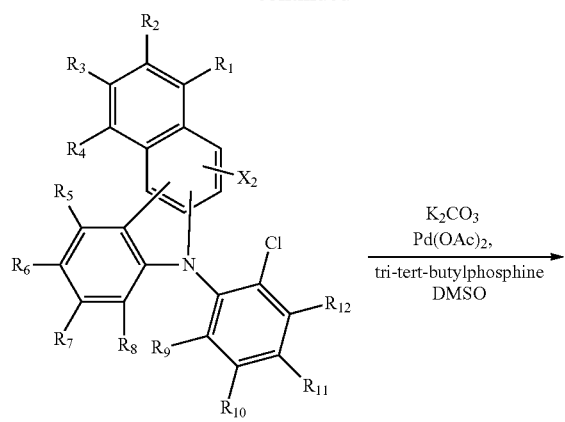

Core 1-III

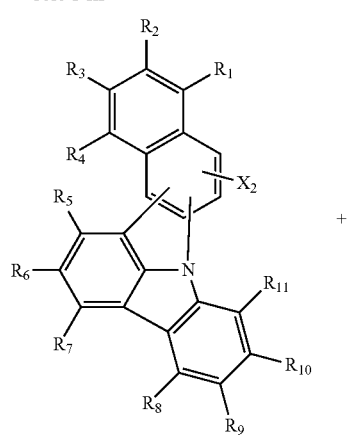

Core 1-IV

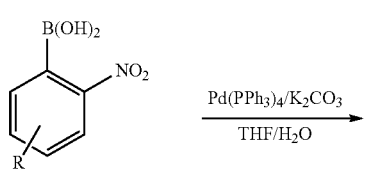

R = R₁₂~R₁₅

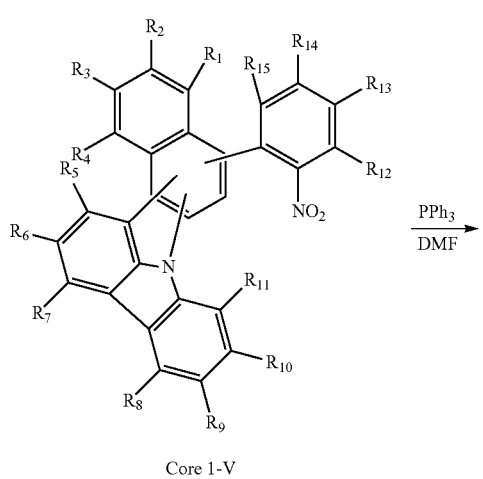

Core 1-V

-continued

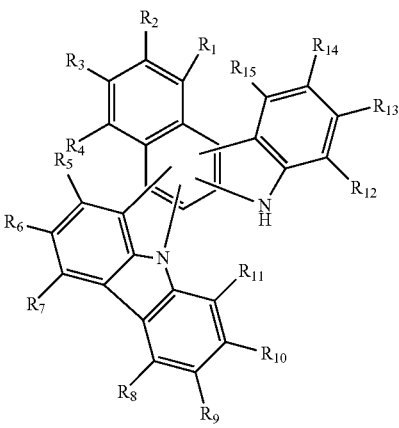

Core

Synthesis examples of the compounds belonging to Core of the Reaction Scheme 2 are the same as Schemes 3 to 7, but are not limited thereto.

Synthesis Example of Core 1-I

<Reaction Scheme 3>

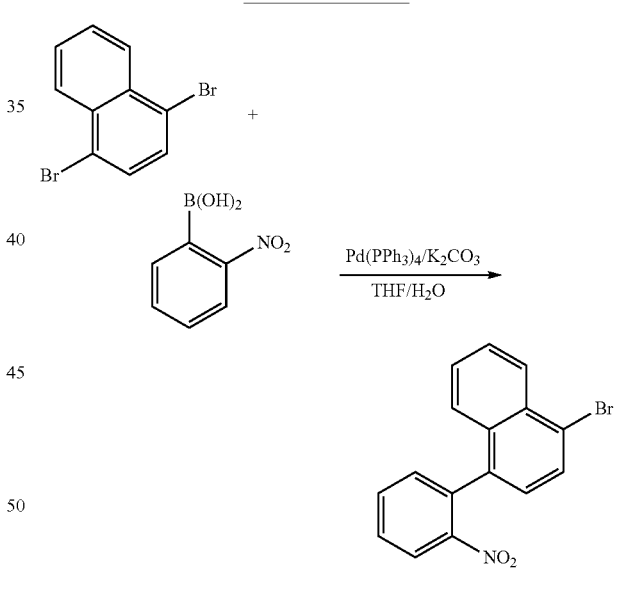

Core 1-I

After 1,4-dibromonaphthalene (40.0 g, 139.9 mmol) and (2-nitrophenyl)boronic acid (23.3 g, 139.9 mmol) were dissolved in THF (700 mL), Pd(PPh₃)₄ (4.9 g, 4.2 mmol), K₂CO₃ (58.0 g, 419.6 mmol) and water (300 mL) were added thereto and the mixture was stirred under reflux. When the reaction was completed, the reaction product was extracted with ether and water and the organic layer was concentrated. The concentrated organic layer was dried with MgSO₄ and concentrated once more. The final concentrate was passed through silica gel column and recrystalized to obtain 35.5 g (yield: 77%) of the product.

Synthesis Example of Core 1-II

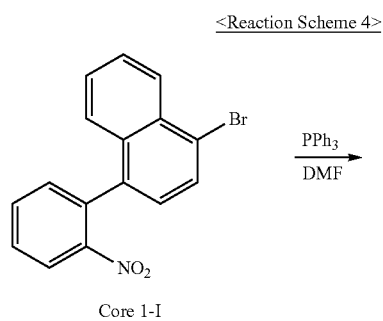

After Core 1-I (35.5 g, 108.2 mmol) was dissolved in DMF (350 mL) in a round bottom flask, PPh₃ (85.12 g, 324.5 mmol) was added thereto and the mixture was stirred at 165° C. When reaction was completed, the reaction product was extracted with CH₂Cl₂ and water. The organic layer was dried with MgSO₄ and concentrated.

The concentrate was passed through silica gel column and recrystallized to obtain 28.0 g (yield: 87%) of the product.

Synthesis Example of Core 1-III

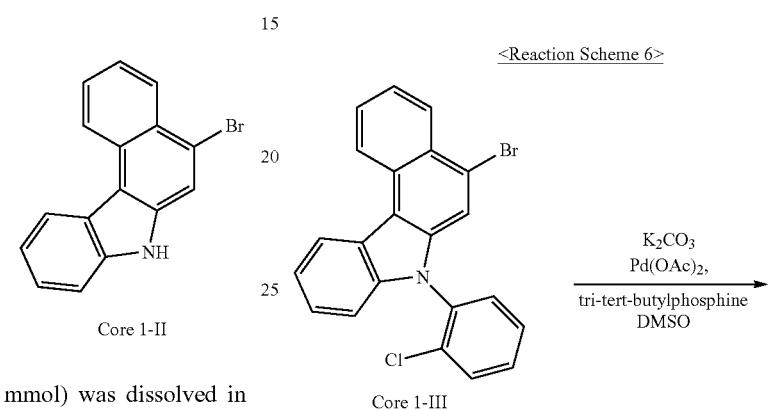

Core 1-II (28.0 g, 99.5 mmol) and 1-chloro-2-fluorobenzene (18.5 g, 141.8 mmol) were placed into a round bottom flask and dissolved in DMF (300 mL). K₂CO₃ (39.2 g, 283.6 mmol) was added thereto and the mixture was stirred at 165° C. When reaction was completed, the reaction product was extracted with CH₂Cl₂ and water. The organic layer was dried with MgSO₄ and concentrated. The concentrate was passed through silica gel column and recrystallized to obtain 31.0 g (yield: 81%) of the product.

Synthesis Example of Core 1-IV

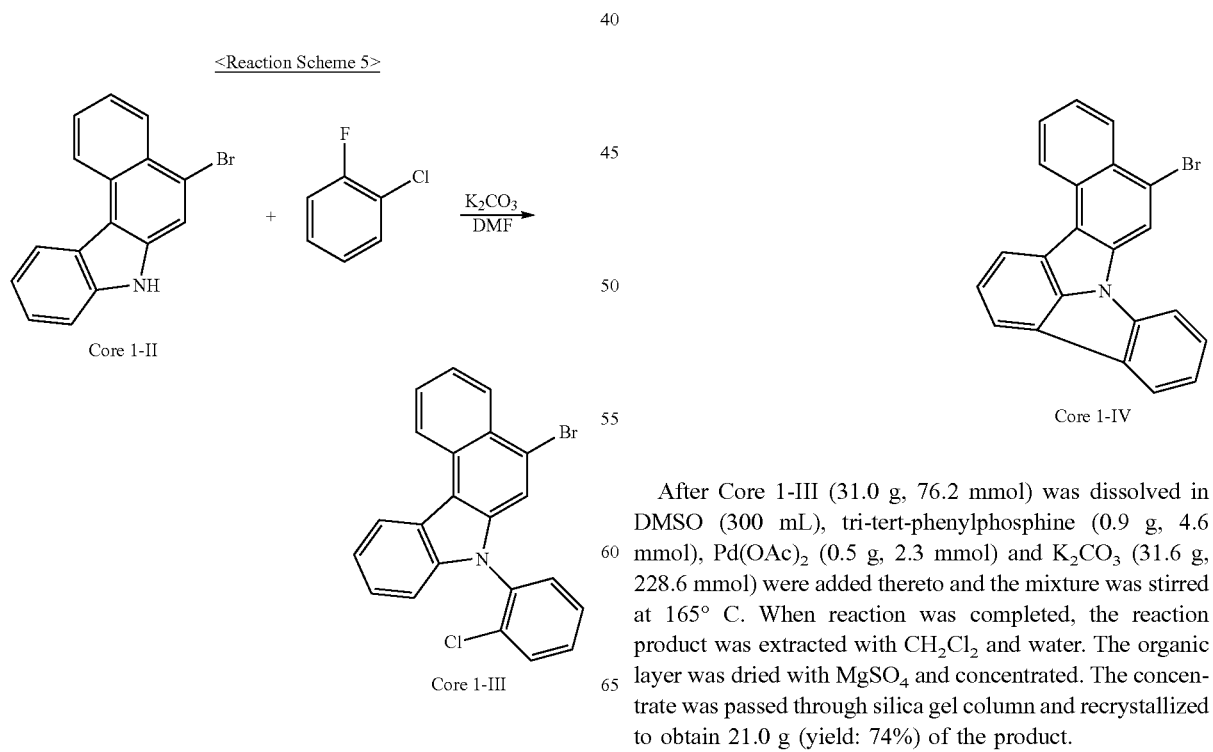

After Core 1-III (31.0 g, 76.2 mmol) was dissolved in DMSO (300 mL), tri-tert-phenylphosphine (0.9 g, 4.6 mmol), Pd(OAc)₂ (0.5 g, 2.3 mmol) and K₂CO₃ (31.6 g, 228.6 mmol) were added thereto and the mixture was stirred at 165° C. When reaction was completed, the reaction product was extracted with CH₂Cl₂ and water. The organic layer was dried with MgSO₄ and concentrated. The concentrate was passed through silica gel column and recrystallized to obtain 21.0 g (yield: 74%) of the product.

Synthesis Example of Core 1-V

<Reaction Scheme 7>

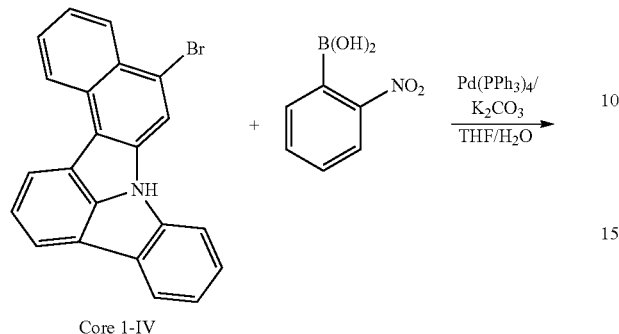

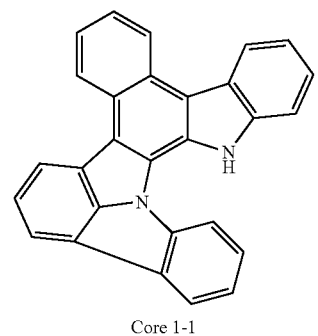

Core 1-V (21.0 g, 56.7 mmol) was carried out in the same manner as the synthesis method of Core 1-II and 14.0 g (yield: 78%) of the product was obtained.

Synthesis Example of Core 1-3

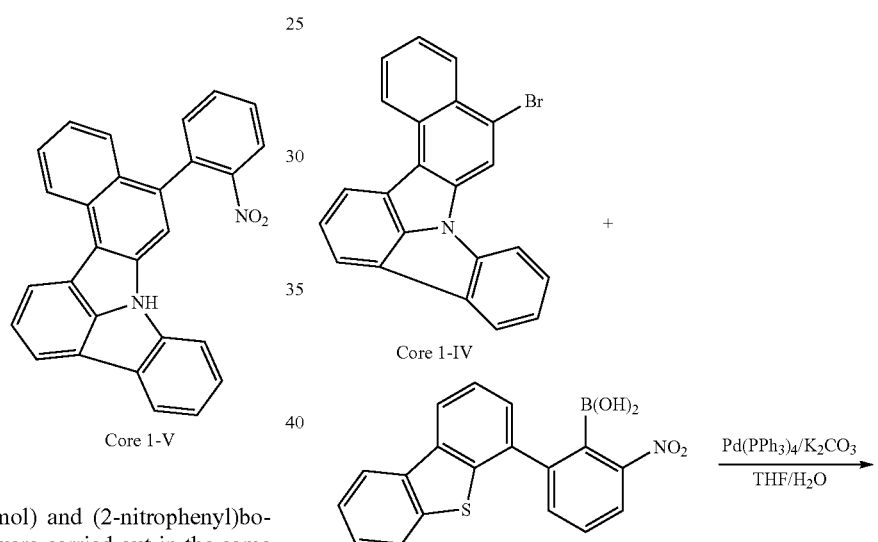

Core 1-IV (21.0 g, 56.7 mmol) and (2-nitrophenyl)boronic acid (9.5 g, 56.7 mmol) were carried out in the same manner as the synthesis method of Core 1-I and 19.5 g (yield: 83%) of the product was obtained.

Synthesis Example of Core 1-I

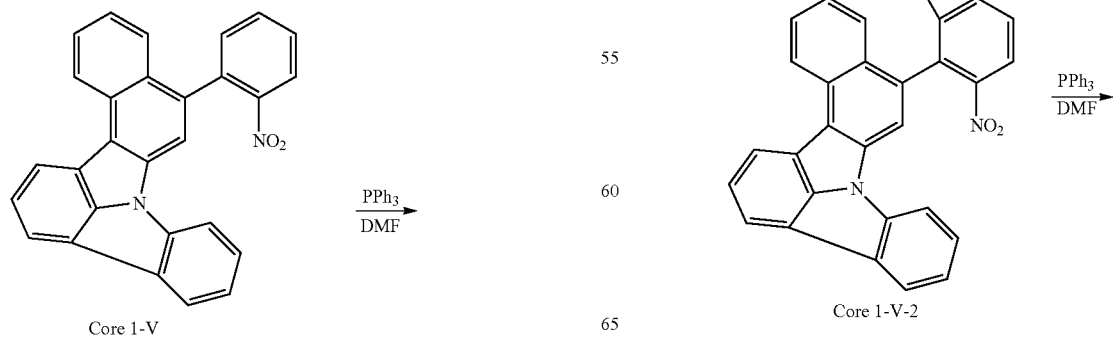

Core 1-3

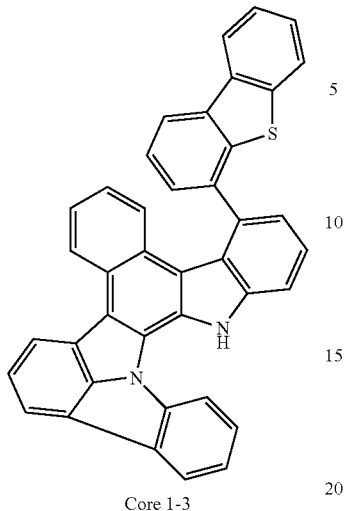

(1) Synthesis of Core 1-V-2

Core 1-IV (12.0 g, 32.4 mmol) and ((2-(dibenzo[b,d]thiophen-4-yl)-6-nitrophenyl)boronic acid (11.3 g, 32.4 mmol) were carried out in the same manner as the synthesis method of Core 1-I and 15.5 g (yield: 80%) of the product was obtained.

(2) Synthesis of Core 1-3

Core 1-V-2 (15.5 g, 26.1 mmol) obtained in the above synthesis was carried out in the same manner as the synthesis method of Core 1-11 and 10.5 g (yield: 72%) of the product was obtained.

Compounds belonging to Core may be, but not limited to, the following compounds, and FD-MS (Field Desorption-Mass Spectrometry) values of the following compounds are shown in Table 1 below.

Core 1-1

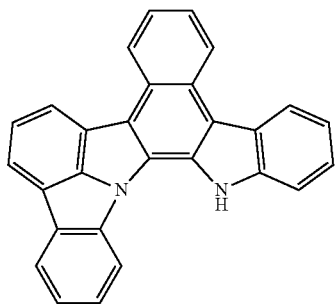

Core 1-2

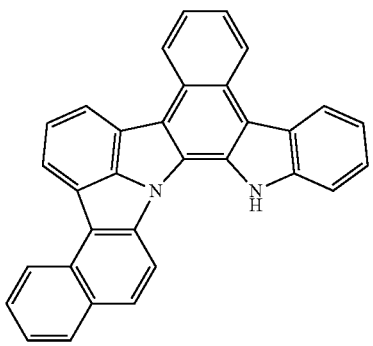

Core 1-3

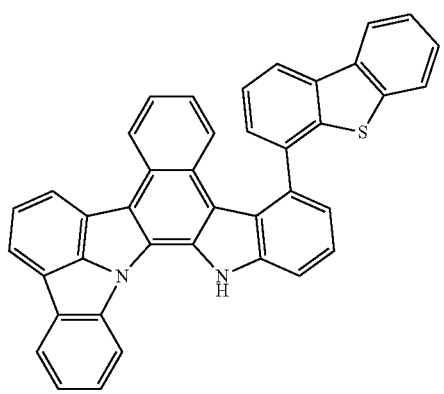

Core 1-4

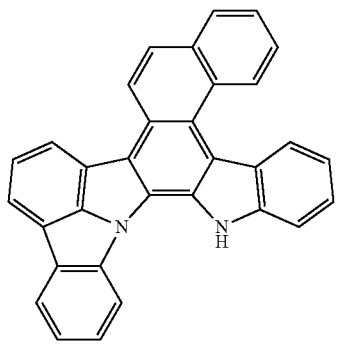

Core 1-5

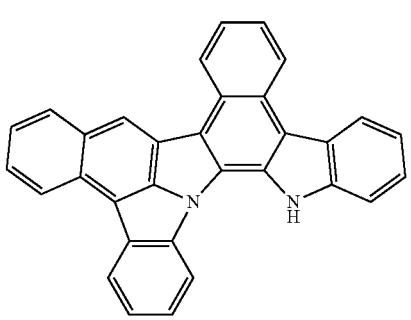

Core 1-6
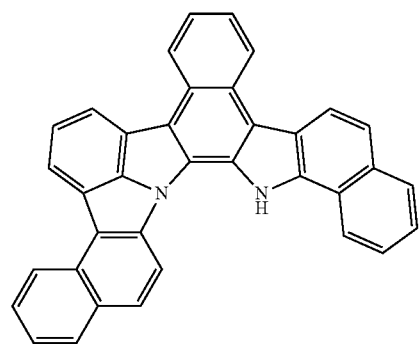
Core 1-7
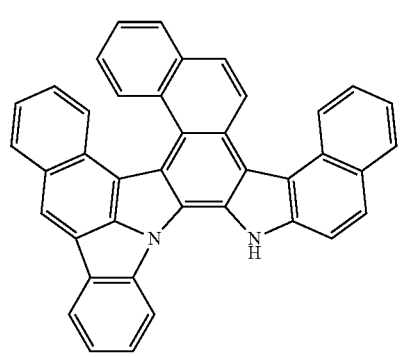
Core 1-8
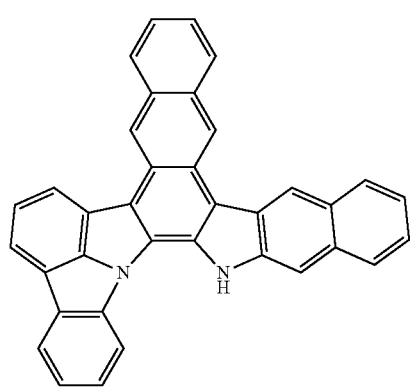
Core 1-9
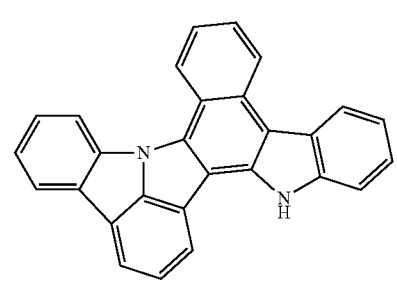
Core 1-10
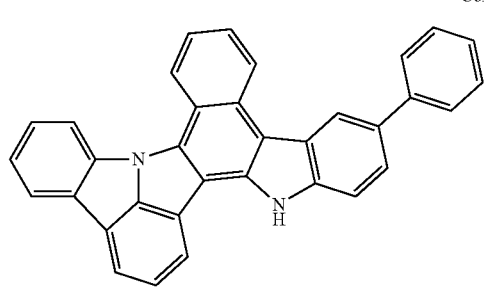
Core 1-11
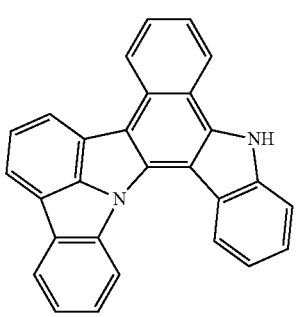
Core 1-12
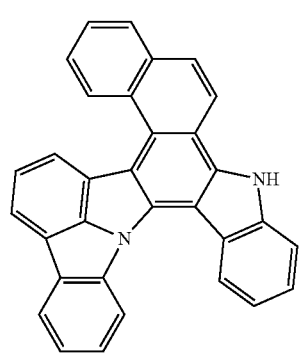
Core 1-13
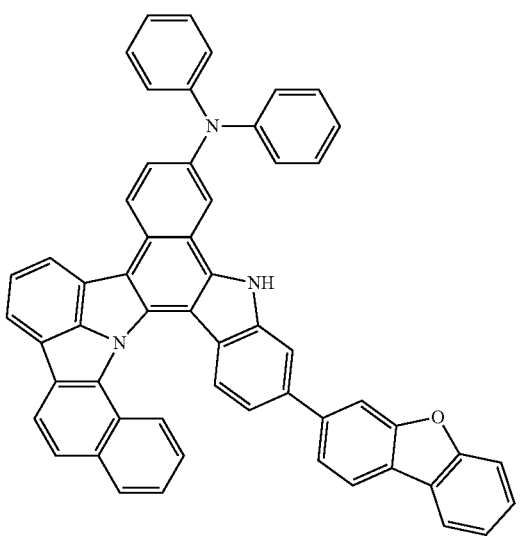
Core 1-14
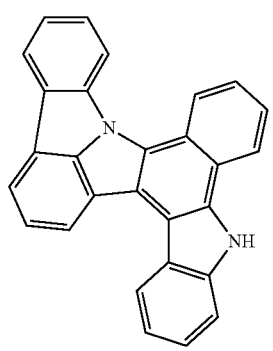

-continued

Core 1-15

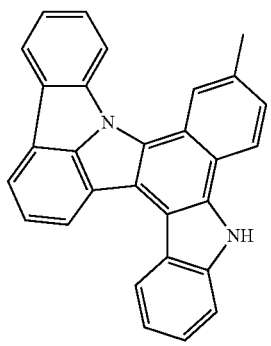

Core 1-16

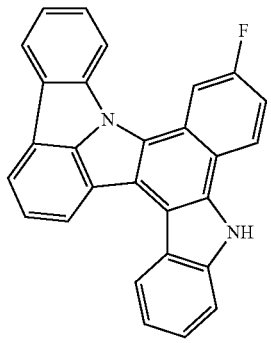

-continued

Core 1-17

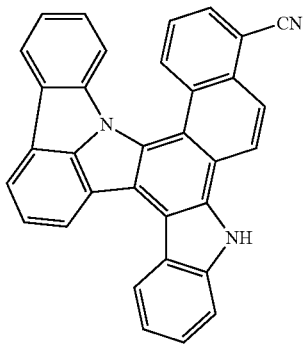

Core 1-18

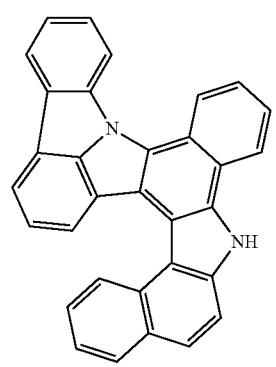

TABLE 1

| Compound | FD-MS | Compound | FD-MS |
| --- | --- | --- | --- |
| Core 1-1 | m/z = 380.13 ($C_{28}H_{16}N_2$ = 380.45) | Core 1-2 | m/z = 430.15 ($C_{32}H_{18}N_2$ = 430.51) |
| Core 1-3 | m/z = 562.15 ($C_{40}H_{22}N_2S$ = 562.69) | Core 1-4 | m/z = 430.15 ($C_{32}H_{18}N_2$ = 430.51) |
| Core 1-5 | m/z = 430.15 ($C_{32}H_{18}N_2$ = 430.51) | Core 1-6 | m/z = 430.15 ($C_{32}H_{18}N_2$ = 430.51) |
| Core 1-7 | m/z = 530.18 ($C_{40}H_{22}N_2$ = 530.63) | Core 1-8 | m/z = 430.15 ($C_{32}H_{18}N_2$ = 430.51) |
| Core 1-9 | m/z = 380.13 ($C_{28}H_{16}N_2$ = 380.45) | Core 1-10 | m/z = 456.16 ($C_{34}H_{20}N_2$ = 456.55) |
| Core 1-11 | m/z = 380.13 ($C_{28}H_{16}N_2$ = 380.45) | Core 1-12 | m/z = 430.15 ($C_{32}H_{18}N_2$ = 430.51) |
| Core 1-13 | m/z = 763.26 ($C_{56}H_{33}N_3O$ = 763.90) | Core 1-14 | m/z = 380.13 ($C_{28}H_{16}N_2$ = 380.45) |
| Core 1-15 | m/z = 394.15 ($C_{29}H_{18}N_2$ = 394.48) | Core 1-16 | m/z = 398.12 ($C_{28}H_{15}N_2F$ = 398.44) |
| Core 1-17 | m/z = 455.14 ($C_{33}H_{17}N_3$ = 455.52) | Core 1-18 | m/z = 430.15 ($C_{32}H_{18}N_2$ = 430.51) |

II. The Example of Sub

Sub of the Reaction Scheme 1 can be synthesized according to the reaction route of the following Reaction Scheme 8, but there is no limitation thereto.

<Reaction Scheme 8>

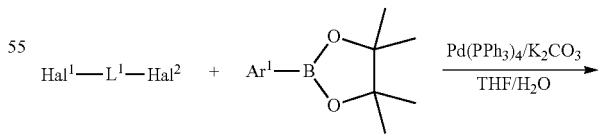

Hal$^1$—L$^1$—Ar$^1$
Sub (Hal$^1$ = I, Br or Cl; Hal$^2$ = Br or Cl)

Synthesis Example of Sub 1-11

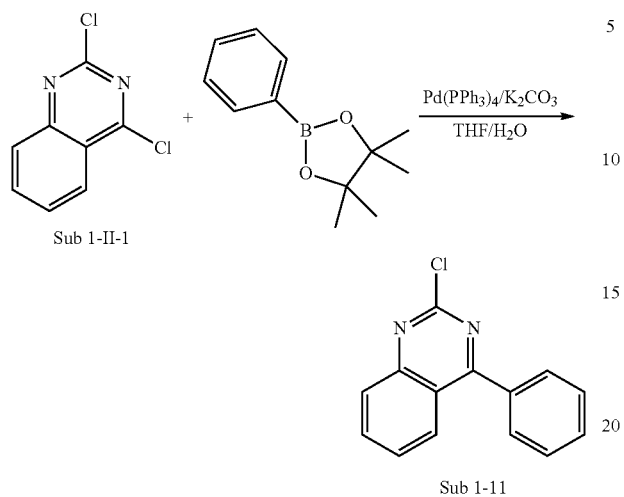

After Sub 1-II-1 (20 g, 100.49 mmol) and 4,4,5,5-tetramethyl-2-phenyl-1,3,2-dioxaborolane (24.61 g, 120.58 mmol) were dissolved in THF (368 mL), Pd(PPh$_3$)$_4$ (4.64 g, 4.02 mmol), K$_2$CO$_3$ (41.67 g, 301.46 mmol) and water (184 mL) were added thereto and the mixture was stirred under reflux. When the reaction was completed, the reaction product was extracted with ether and water and the organic layer was concentrated. The concentrated organic layer was dried with MgSO$_4$ and concentrated once more. The final concentrate was passed through silica gel column and recrystallized to obtain 18.14 g (yield: 75%) of product.

Synthesis Example of Sub 1-32

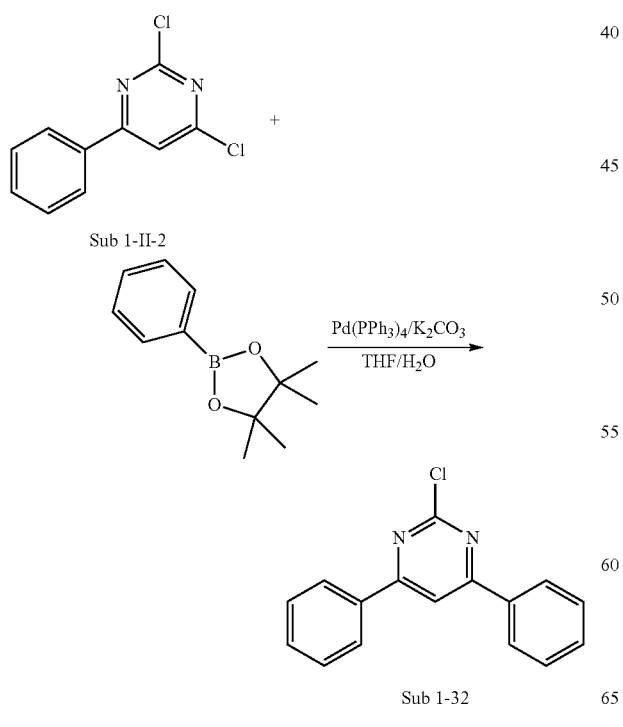

Sub 1-II-2 (20 g, 88.86 mmol), THF (326 mL), 4,4,5,5-tetramethyl-2-phenyl-1,3,2-dioxaborolane (21.76 g, 106.63 mmol), Pd(PPh$_3$)$_4$ (4.11 g, 3.55 mmol), K$_2$CO$_3$ (36.84 g, 266.58 mmol) and water (163 mL) were carried out in the same manner as the synthesis method of Sub 1-11 and 17.13 g (yield: 72%) of the product was obtained.

Synthesis Example of Sub 1-39

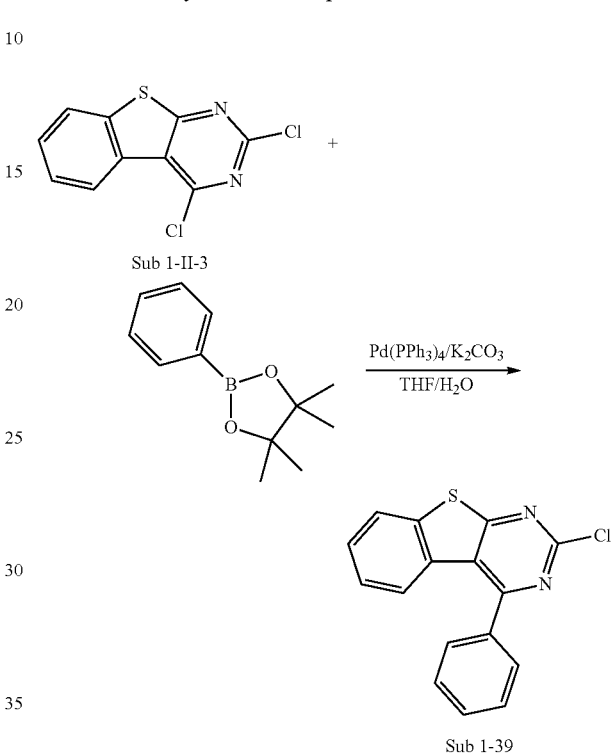

Sub 1-II-3 (20 g, 78.39 mmol), THF (287 mL), 4,4,5,5-tetramethyl-2-phenyl-1,3,2-dioxaborolane (19.20 g, 94.07 mmol), Pd(PPh$_3$)$_4$ (3.62 g, 3.14 mmol), K$_2$CO$_3$ (32.50 g, 235.18 mmol) and water (144 mL) were carried out in the same manner as the synthesis method of Sub 1-11 and 15.82 g (yield: 68%) of the product was obtained.

Compounds belonging to Sub 2 may be, but not limited to, the following compounds, and Table 2 shows the FD-MS values of the following compounds.

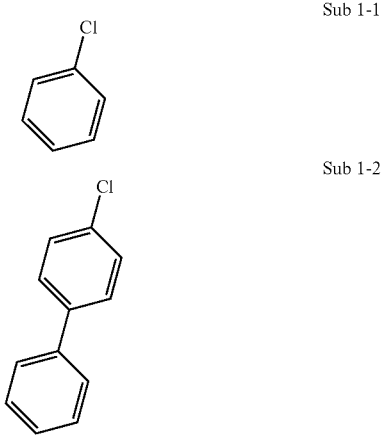

Sub 1-3
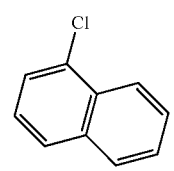
Sub 1-4
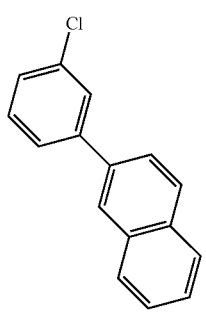
Sub 1-5
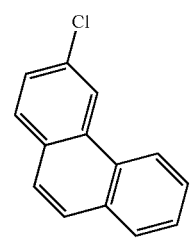
Sub 1-6
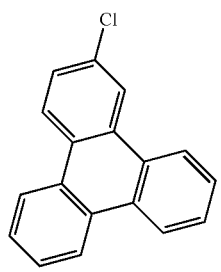
Sub 1-7
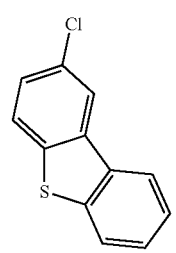
Sub 1-8
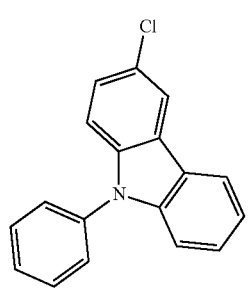
Sub 1-9
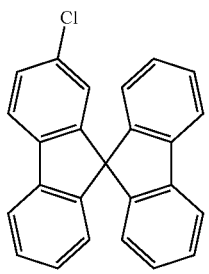
Sub 1-10
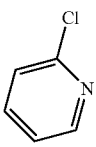
Sub 1-11
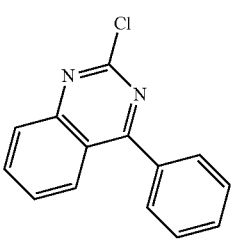
Sub 1-12
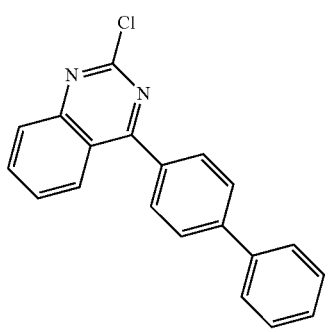
Sub 1-13
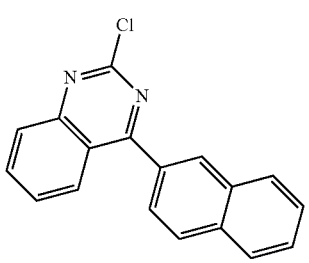
Sub 1-14
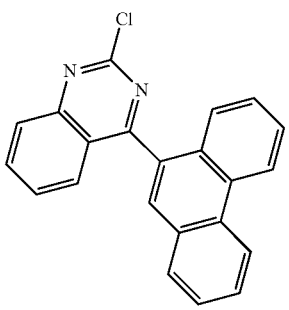

Sub 1-15 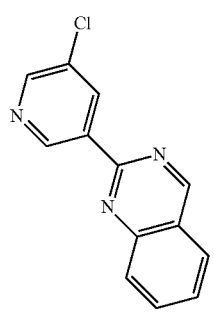
Sub 1-16 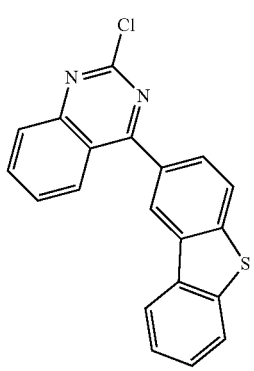
Sub 1-17 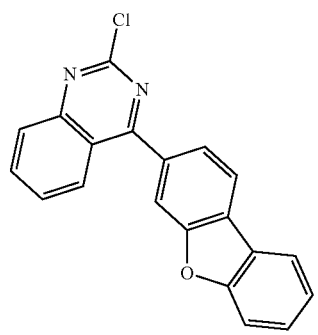
Sub 1-18 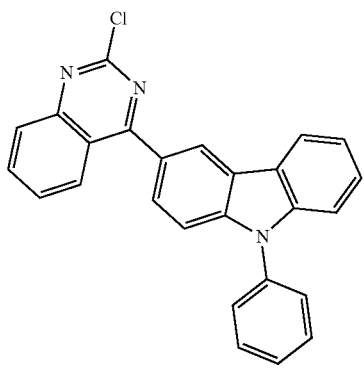
Sub 1-19 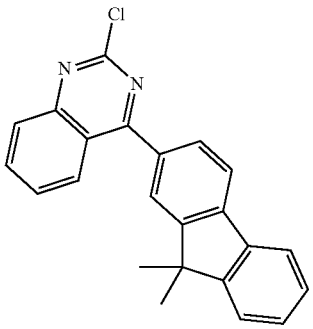
Sub 1-20 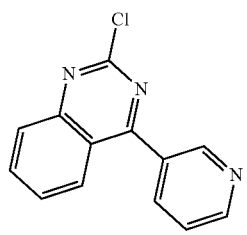
Sub 1-21 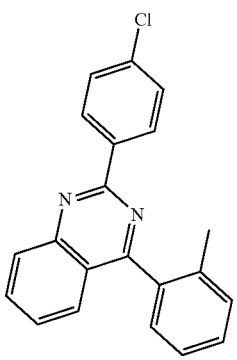
Sub 1-22 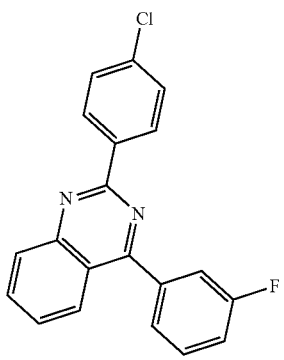

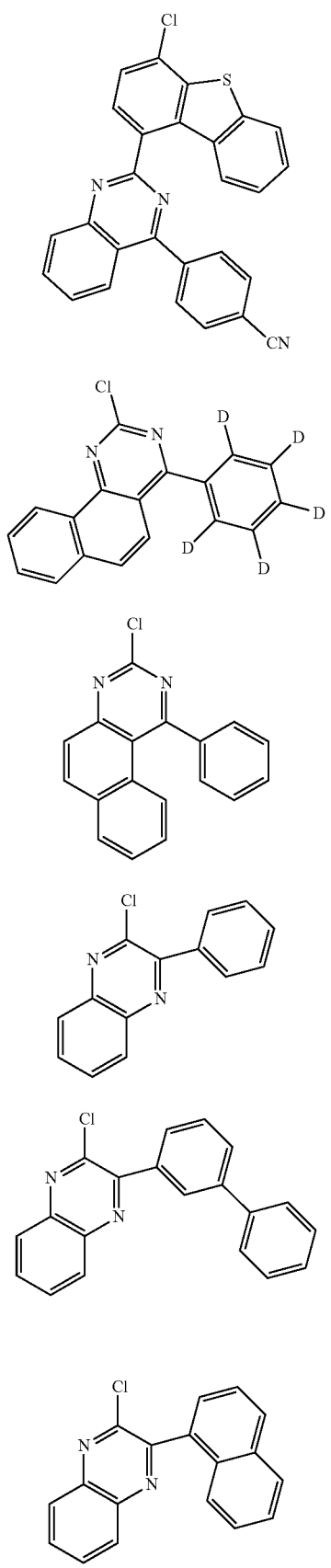
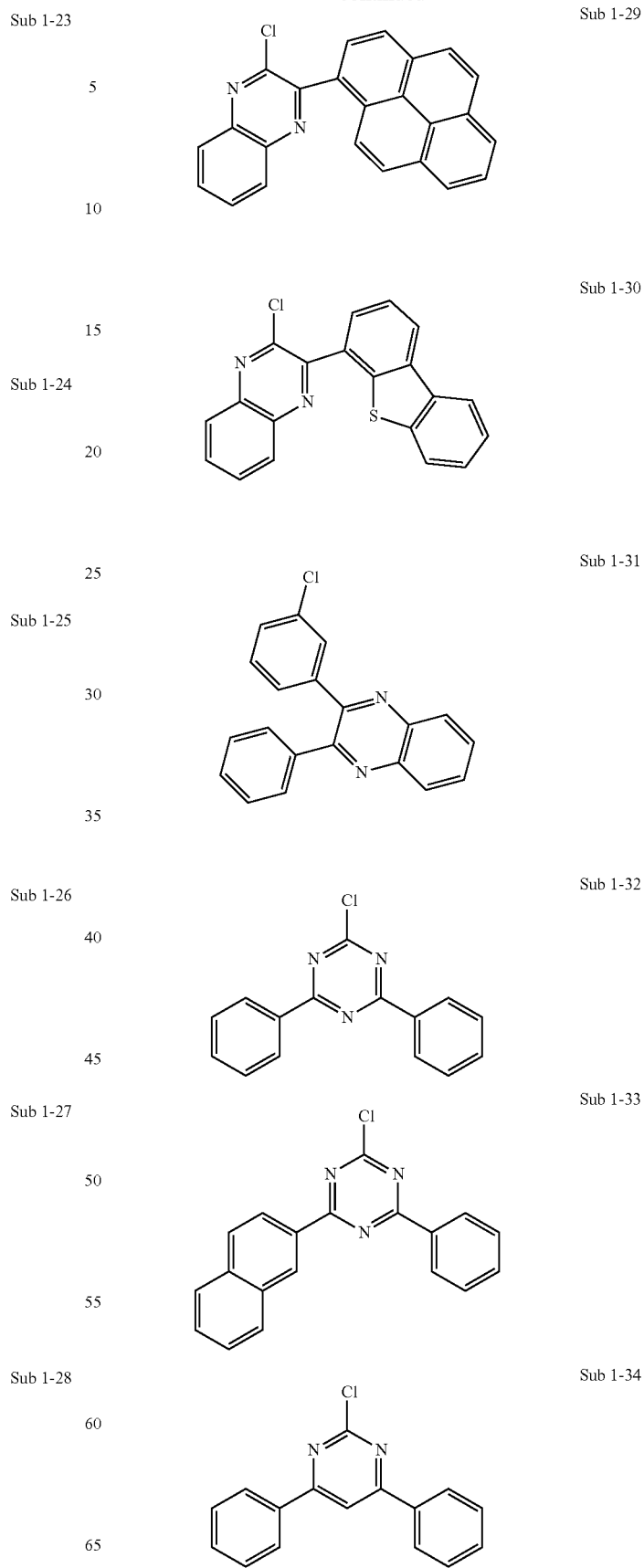

-continued
Sub 1-35
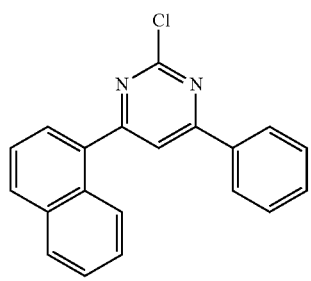
Sub 1-36
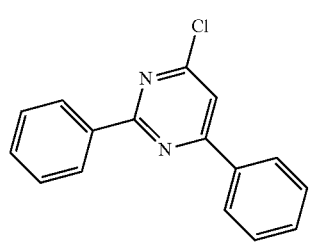
Sub 1-37
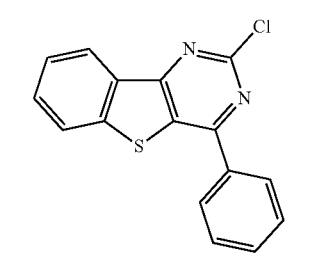
Sub 1-38
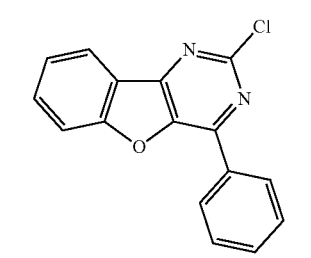
Sub 1-39
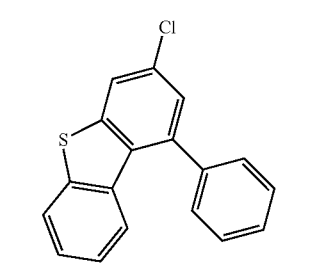
Sub 1-40
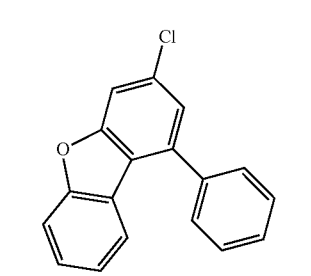
-continued
Sub 1-41
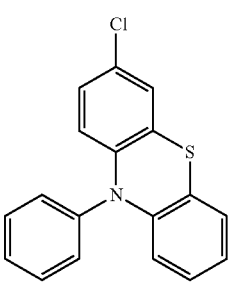
Sub 1-42
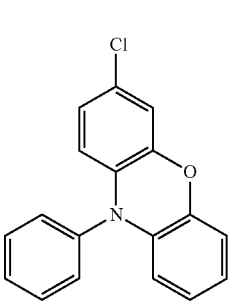
Sub 1-43
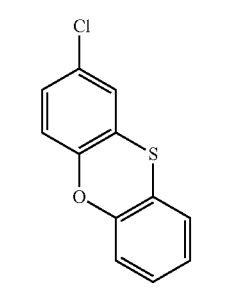
Sub 1-44
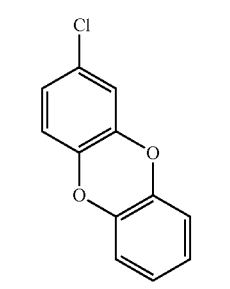
Sub 1-45
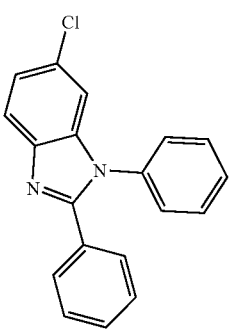

-continued
Sub 1-46
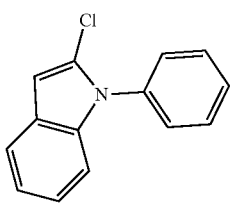
Sub 1-47
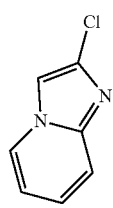
Sub 1-48
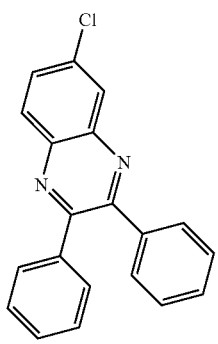
Sub 1-49
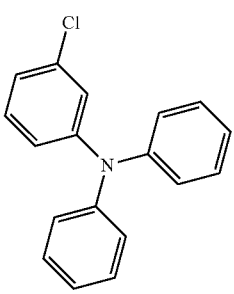
Sub 1-50
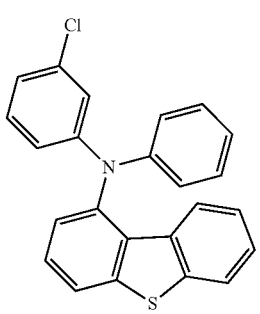
Sub 1-51
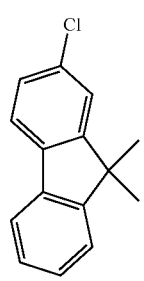
-continued
Sub 1-52
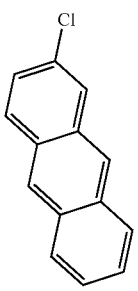
Sub 1-53
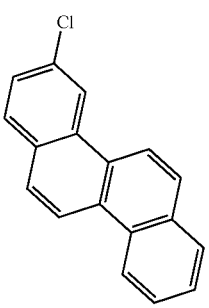
Sub 1-54
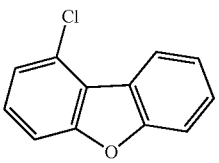
Sub 1-55
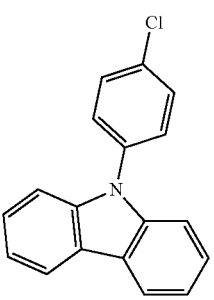
Sub 1-56
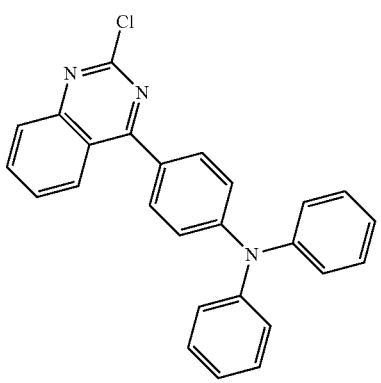

-continued

Sub 1-57

Sub 1-58

Sub 1-59

Sub 1-60

Sub 1-61

Sub 1-62

Sub 1-63

Sub 1-64

Sub 1-65

Sub 1-66

Sub 1-67

Sub 1-68

Sub 1-69

Sub 1-70

Sub 1-71

Sub 1-72

Sub 1-73

Sub 1-74

Sub 1-75

Sub 1-76

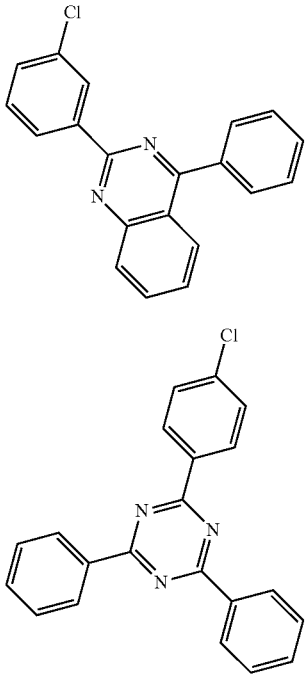

Sub 1-77

Sub 1-78

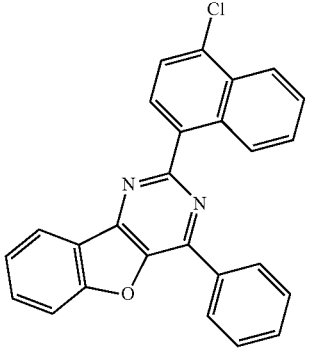

Sub 1-79

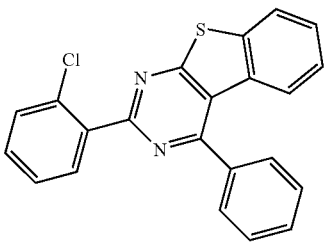

Sub 1-80

TABLE 2

| Compound | FD-MS | Compound | FD-MS |
| --- | --- | --- | --- |
| Sub 1-1 | m/z = 112.01 ($C_6H_5Cl$ = 112.56) | Sub 1-2 | m/z = 188.04 ($C_{12}H_9Cl$ = 188.65) |
| Sub 1-3 | m/z = 162.02 ($C_{10}H_7Cl$ = 162.62) | Sub 1-4 | m/z = 238.05 ($C_{16}H_{11}Cl$ = 238.71) |
| Sub 1-5 | m/z = 212.04 ($C_{14}H_9Cl$ = 212.68) | Sub 1-6 | m/z = 262.05 ($C_{18}H_{11}Cl$ = 262.74) |
| Sub 1-7 | m/z = 218.00 ($C_{12}H_7ClS$ = 218.70) | Sub 1-8 | m/z = 277.07 ($C_{18}H_{12}ClN$ = 277.75) |
| Sub 1-9 | m/z = 350.09 ($C_{25}H_{15}Cl$ = 350.85) | Sub 1-10 | m/z = 113.00 ($C_5H_4ClN$ = 113.54) |
| Sub 1-11 | m/z = 240.05 ($C_{14}H_9ClN_2$ = 240.69) | Sub 1-12 | m/z = 316.08 ($C_{20}H_{13}ClN_2$ = 316.79) |
| Sub 1-13 | m/z = 241.04 ($C_{18}H_{11}ClN_2$ = 241.68) | Sub 1-14 | m/z = 340.08 ($C_{22}H_{13}ClN_2$ = 340.81) |
| Sub 1-15 | m/z = 390.09 (C13H8ClN3 = 390.87) | Sub 1-16 | m/z = 346.03 ($C_{20}H_{11}ClN_2S$ = 346.83) |
| Sub 1-17 | m/z = 330.06 ($C_{20}H_{11}ClN_2O$ = 330.77) | Sub 1-18 | m/z = 405.10 ($C_{26}H_{15}ClN_3$ = 405.89) |
| Sub 1-19 | m/z = 356.11 ($C_{23}H_{17}ClN_2$ = 356.85) | Sub 1-20 | m/z = 241.04 ($C_{13}H_8ClN_3$ = 241.68) |
| Sub 1-21 | m/z = 330.09 ($C_{21}H_{15}ClN_2$ = 330.82) | Sub 1-22 | m/z = 384.08 ($C_{24}H_{14}ClFN_2$ = 384.84) |
| Sub 1-23 | m/z = 447.06 ($C_{27}H_{14}ClN_3S$ = 447.94) | Sub 1-24 | m/z = 295.09 ($C_{18}H_6D_5ClN_2$ = 295.78) |
| Sub 1-25 | m/z = 290.06 ($C_{18}H_{11}ClN_2$ = 290.75) | Sub 1-26 | m/z = 240.05 ($C_{14}H_9ClN_2$ = 240.69) |
| Sub 1-27 | m/z = 316.08 ($C_{20}H_{13}ClN_2$ = 316.79) | Sub 1-28 | m/z = 290.06 ($C_{18}H_{11}ClN_2$ = 290.75) |
| Sub 1-29 | m/z = 364.08 ($C_{24}H_{13}ClN_2$ = 364.83) | Sub 1-30 | m/z = 346.03 ($C_{20}H_{11}ClN_2S$ = 346.83) |
| Sub 1-31 | m/z = 316.08 ($C_{20}H_{13}ClN_2$ = 316.79) | Sub 1-32 | m/z = 267.06 ($C_{15}H_{10}ClN_3$ = 267.72) |
| Sub 1-33 | m/z = 317.07 ($C_{19}H_{12}ClN_3$ = 317.78) | Sub 1-34 | m/z = 266.06 ($C_{16}H_{11}ClN_2$ = 267.73) |
| Sub 1-35 | m/z = 316.08 ($C_{20}H_{13}ClN_2$ = 316.79) | Sub 1-36 | m/z = 266.06 ($C_{16}H_{11}ClN_2$ = 267.73) |
| Sub 1-37 | m/z = 296.02 ($C_{16}H_9ClN_2S$ = 296.77) | Sub 1-38 | m/z = 280.04 ($C_{16}H_9ClN_2O$ = 280.71) |
| Sub 1-39 | m/z = 296.02 ($C_{16}H_9ClN_2S$ = 296.77) | Sub 1-40 | m/z = 280.04 ($C_{16}H_9ClN_2O$ = 280.71) |
| Sub 1-41 | m/z = 309.04 ($C_{18}H_{12}ClNS$ = 309.81) | Sub 1-42 | m/z = 293.06 ($C_{18}H_{12}ClNO$ = 293.75) |
| Sub 1-43 | m/z = 233.99 ($C_{12}H_7ClOS$ = 234.70) | Sub 1-44 | m/z = 218.01 ($C_{12}H_7ClO_2$ = 218.64) |
| Sub 1-45 | m/z = 304.08 ($C_{19}H_{13}ClN_2$ = 304.78) | Sub 1-46 | m/z = 227.05 ($C_{14}H_{10}ClN$ = 227.69) |
| Sub 1-47 | m/z = 152.01 ($C_7H_5ClN_2$ = 152.58) | Sub 1-48 | m/z = 316.08 ($C_{20}H_{13}ClN_2$ = 316.79) |
| Sub 1-49 | m/z = 279.08 ($C_{18}H_{14}ClN$ = 279.77) | Sub 1-50 | m/z = 385.07 ($C_{24}H_{16}ClNS$ = 385.91) |
| Sub 1-51 | m/z = 228.07 ($C_{13}H_{13}Cl$ = 228.72) | Sub 1-52 | m/z = 212.04 ($C_{14}H_9Cl$ = 212.68) |
| Sub 1-53 | m/z = 262.05 ($C_{18}H_{11}Cl$ = 262.74) | Sub 1-54 | m/z = 202.02 ($C_{12}H_7ClO$ = 202.64) |
| Sub 1-55 | m/z = 277.07 ($C_{18}H_{12}ClN$ = 277.75) | Sub 1-56 | m/z = 407.12 ($C_{26}H_{18}ClN_3$ = 407.90) |
| Sub 1-57 | m/z = 299.06 ($C_{18}H_6D_5ClS$ = 299.83) | Sub 1-58 | m/z = 188.04 ($C_{12}H_9Cl$ = 188.65) |
| Sub 1-59 | m/z = 338.09 ($C_{24}H_{15}Cl$ = 338.83) | Sub 1-60 | m/z = 366.09 ($C_{24}H_{15}ClN_2$ = 366.85) |
| Sub 1-61 | m/z = 531.15 ($C_{36}H_{22}ClN_3$ = 531.04) | Sub 1-62 | m/z = 417.10 ($C_{27}H_{16}ClN_3$ = 417.90) |
| Sub 1-63 | m/z = 346.03 ($C_{20}H_{11}ClN_2S$ = 346.83) | Sub 1-64 | m/z = 381.07 ($C_{23}H_{12}ClN_3S$ = 381.82) |
| Sub 1-65 | m/z = 240.05 ($C_{14}H_9ClN_2$ = 240.69) | Sub 1-66 | m/z = 245.10 ($C_{15}H_{16}ClN$ = 245.75) |
| Sub 1-67 | m/z = 264.07 ($C_{18}H_{13}Cl$ = 264.75) | Sub 1-68 | m/z = 290.06 ($C_{18}H_{11}ClN_2$ = 290.75) |
| Sub 1-69 | m/z = 316.08 ($C_{20}H_{13}ClN_2$ = 316.79) | Sub 1-70 | m/z = 267.06 ($C_{15}H_{10}ClN_3$ = 267.72) |
| Sub 1-71 | m/z = 114.99 ($C_3H_2ClN_3$ = 115.52) | Sub 1-72 | m/z = 380.11 ($C_{25}H_{17}ClN_2$ = 380.88) |
| Sub 1-73 | m/z = 340.08 ($C_{22}H_{13}ClN_2$ = 340.81) | Sub 1-74 | m/z = 266.06 ($C_{16}H_{11}ClN_2$ = 267.73) |
| Sub 1-75 | m/z = 290.09 ($C_{20}H_{15}Cl$ = 290.79) | Sub 1-76 | m/z = 245.08 ($C_{14}H_4D_5ClN_2$ = 245.72) |
| Sub 1-77 | m/z = 316.08 ($C_{20}H_{13}ClN_2$ = 316.79) | Sub 1-78 | m/z = 343.09 ($C_{21}H_{14}ClN_3$ = 343.81) |
| Sub 1-79 | m/z = 406.09 ($C_{26}H_{15}ClN_2O$ = 406.87) | Sub 1-80 | m/z = 372.05 ($C_{22}H_{13}ClN_2S$ = 372.87) |

Synthesis Example of Final Product

Synthesis Example of P-11

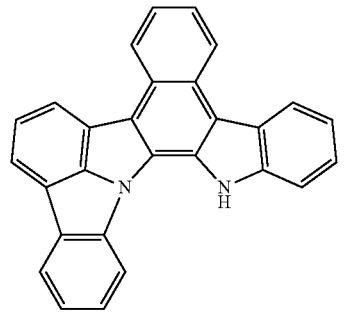

Core 1-1

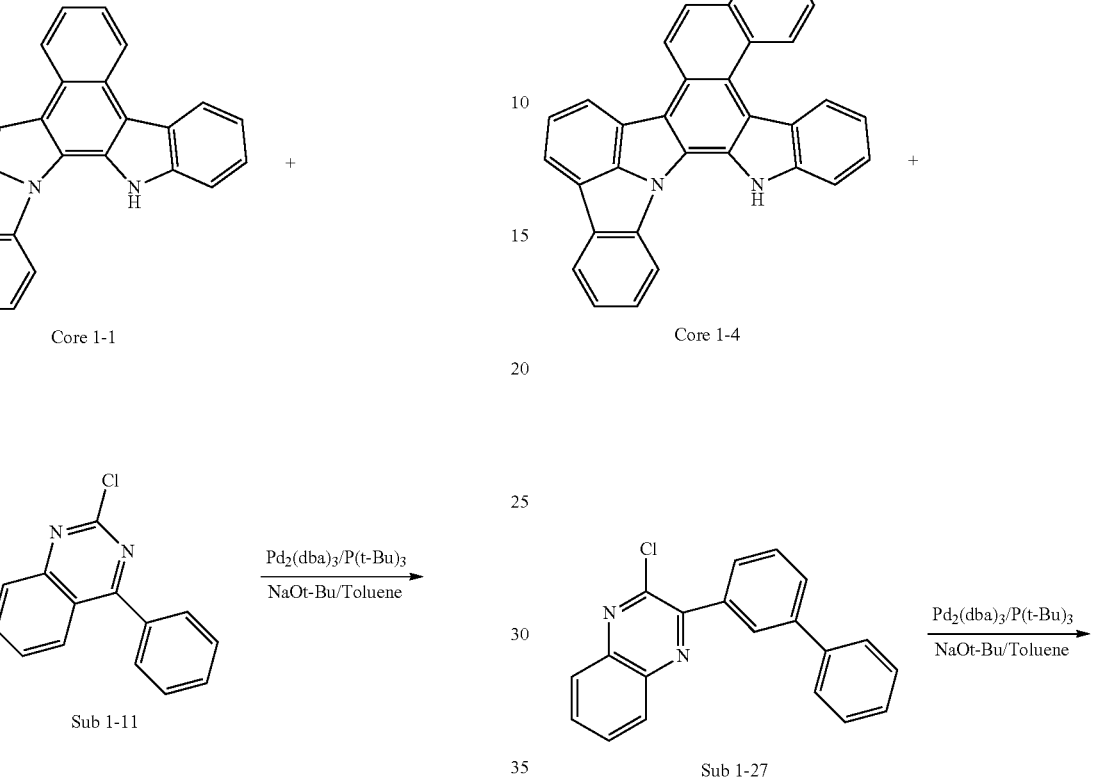

Sub 1-11

P-11

After Core 1-1 (10.0 g, 26.3 mmol) was dissolved in toluene (100 mL) in a round bottom flask, Sub 1-II [Cas. 29874-83-7] (6.3 g, 26.3 mmol), $Pd_2(dba)_3$ (0.7 g, 0.8 mmol), $P(t-Bu)_3$ (0.3 g, 1.6 mmol) and NaOt-Bu (7.5 g, 78.9 mmol) were added thereto and the mixture was stirred at 100° C. When the reaction was completed, the reaction product was extracted with $CH_2Cl_2$ and water. The organic layer was dried with $MgSO_4$ and concentrated. The concentrate was passed through silica gel column and recrystallized to obtain 11.4 g (yield: 74%) of product.

Synthesis Example of P-27

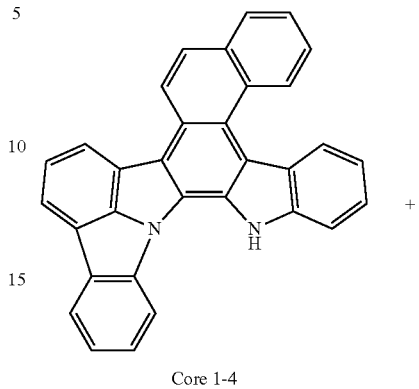

Core 1-4

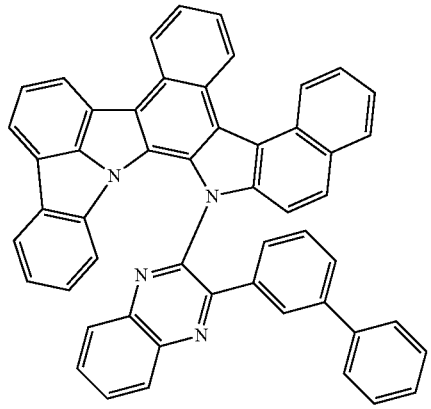

P-27

Core 1-4 (8.8 g, 20.4 mmol) and Sub 1-27 [Cas. 1413365-66-8] (6.5 g, 20.4 mmol) were carried out in the same manner as the synthesis method of P-11 and 12.2 g (yield: 84%) of the product was obtained.

Synthesis Example of P-63
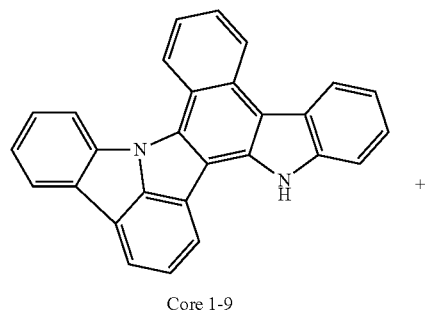
Core 1-9
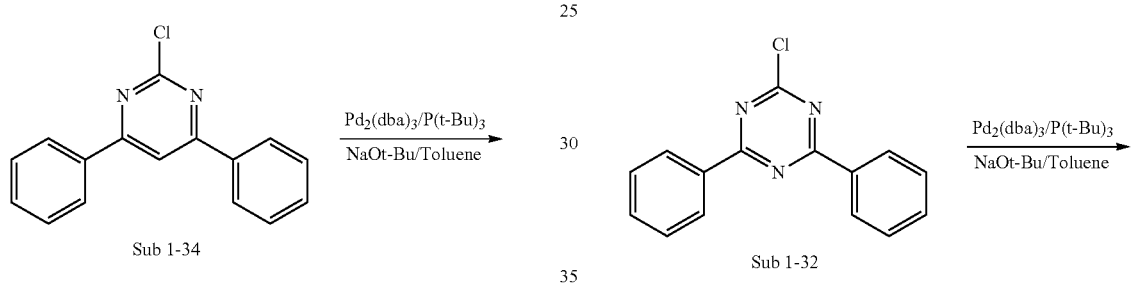
P-63
Core 1-9 (9.0 g, 23.6 mmol) and Sub 1-34 [Cas. 2915-16-4] (6.3 g, 23.6 mmol) were carried out in the same manner as the synthesis method of P-11 and 11.5 g (yield: 79%) of the product was obtained.
Synthesis Example of P-80
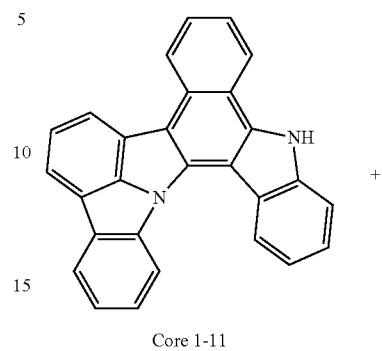
Core 1-11
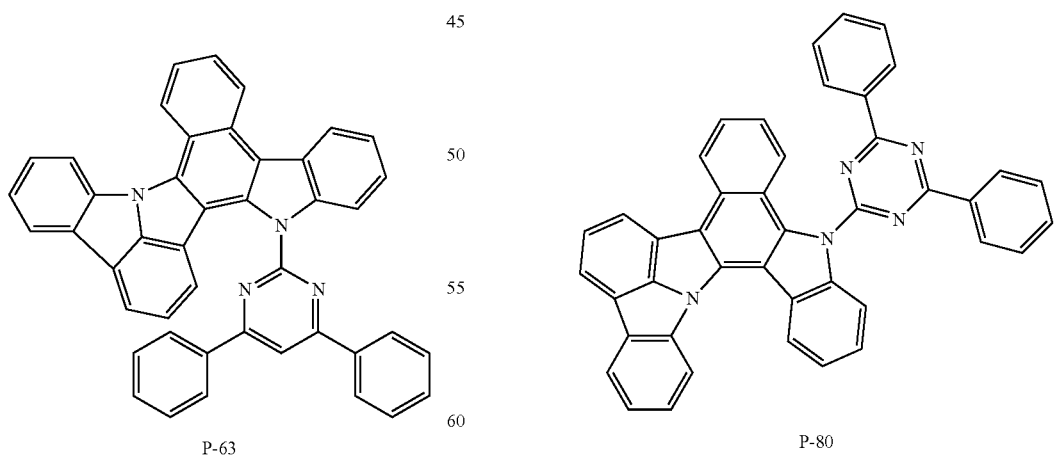
P-80
Core 1-11 (6.5 g, 17.0 mmol) and Sub 1-32 [Cas. 3842-55-5] (4.6 g, 17.0 mmol) were carried out in the same manner as the synthesis method of P-11 and 8.0 g (yield: 77%) of the product was obtained.

Synthesis Example of P-89

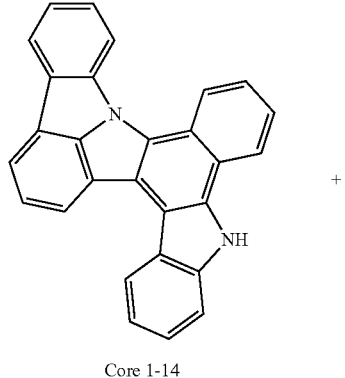

Core 1-14

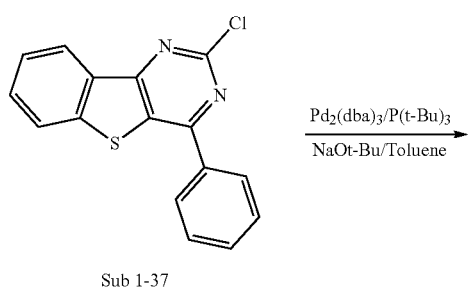

Sub 1-37

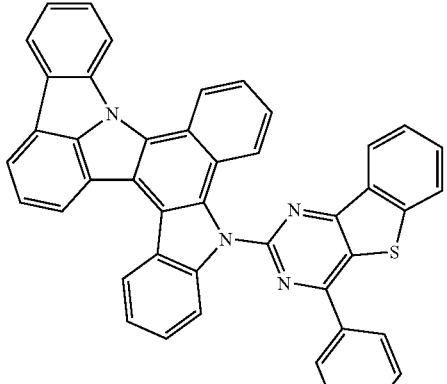

P-89

Core 1-14 (7.2 g, 18.9 mmol) and Sub 1-37 [Cas. 1801233-15-7] (5.6 g, 18.9 mmol) were carried out in the same manner as the synthesis method of P-11 and 9.3 g (yield: 76%) of the product was obtained.

The FD-MS values of the compounds P-1 to P-95 of the present invention prepared according to the above synthesis examples are shown in the following Table 3.

TABLE 3

| Compound | FD-MS | Compound | FD-MS |
| --- | --- | --- | --- |
| P-1 | m/z = 456.16 ($C_{34}H_{20}N_2$ = 456.55) | P-2 | m/z = 532.19 ($C_{40}H_{24}N_2$ = 532.65) |
| P-3 | m/z = 506.18 ($C_{38}H_{22}N_2$ = 506.61) | P-4 | m/z = 582.21 ($C_{44}H_{26}N_2$ = 582.71) |
| P-5 | m/z = 556.19 ($C_{42}H_{24}N_2$ = 556.67) | P-6 | m/z = 606.21 ($C_{46}H_{26}N_2$ = 606.73) |
| P-7 | m/z = 562.15 ($C_{40}H_{22}N_2S$ = 562.69) | P-8 | m/z = 621.22 ($C_{46}H_{27}N_3$ = 621.74) |
| P-9 | m/z = 694.24 ($C_{53}H_{30}N_2$ = 694.84) | P-10 | m/z = 457.16 ($C_{33}H_{19}N_3$ = 457.54) |
| P-11 | m/z = 584.20 ($C_{42}H_{24}N_4$ = 584.68) | P-12 | m/z = 660.23 ($C_{48}H_{28}N_4$ = 660.78) |
| P-13 | m/z = 660.23 ($C_{48}H_{28}N_4$ = 660.78) | P-14 | m/z = 684.23 ($C_{50}H_{28}N_4$ = 684.80) |
| P-15 | m/z = 585.20 ($C_{41}H_{23}N_5$ = 585.67) | P-16 | m/z = 690.19 ($C_{48}H_{26}N_4S$ = 690.82) |
| P-17 | m/z = 674.21 ($C_{48}H_{26}N_4O$ = 674.76) | P-18 | m/z = 749.26 ($C_{54}H_{31}N_5$ = 749.88) |
| P-19 | m/z = 700.26 ($C_{51}H_{32}N_4$ = 700.85) | P-20 | m/z = 585.20 ($C_{42}H_{24}N_4$ = 585.67) |
| P-21 | m/z = 670.27 ($C_{53}H_{34}$ = 670.86) | P-22 | m/z = 728.24 ($C_{52}H_{29}FN_4$ = 728.83) |
| P-23 | m/z = 791.21 ($C_{55}H_{29}N_5S$ = 791.93) | P-24 | m/z = 639.25 ($C_{46}H_{21}D_5N_4$ = 639.77) |
| P-25 | m/z = 684.23 ($C_{50}H_{28}N_4$ = 684.80) | P-26 | m/z = 584.20 ($C_{42}H_{24}N_4$ = 584.68) |
| P-27 | m/z = 710.25 ($C_{53}H_{30}N_4$ = 710.84) | P-28 | m/z = 634.22 ($C_{46}H_{26}N_4$ = 634.74) |
| P-29 | m/z = 890.25 ($C_{64}H_{34}N_4S$ = 891.06) | P-30 | m/z = 690.19 ($C_{48}H_{26}N_4S$ = 690.82) |
| P-31 | m/z = 660.23 ($C_{48}H_{28}N_4$ = 660.78) | P-32 | m/z = 611.21 ($C_{43}H_{25}N_5$ = 611.71) |
| P-33 | m/z = 661.23 ($C_{47}H_{27}N_5$ = 661.77) | P-34 | m/z = 687.24 ($C_{49}H_{29}N_5$ = 687.81) |
| P-35 | m/z = 660.23 ($C_{48}H_{28}N_4$ = 660.78) | P-36 | m/z = 610.22 ($C_{44}H_{26}N_4$ = 610.72) |
| P-37 | m/z = 640.17 ($C_{44}H_{24}N_4S$ = 640.76) | P-38 | m/z = 750.24 ($C_{54}H_{30}N_4O$ = 750.86) |
| P-39 | m/z = 716.20 ($C_{50}H_{28}N_4S$ = 716.86) | P-40 | m/z = 624.20 ($C_{44}H_{24}N_4O$ = 624.70) |
| P-41 | m/z = 653.19 ($C_{46}H_{27}N_3S$ = 653.80) | P-42 | m/z = 637.22 ($C_{46}H_{27}N_3O$ = 637.74) |
| P-43 | m/z = 578.15 ($C_{40}H_{22}N_2OS$ = 578.69) | P-44 | m/z = 562.17 ($C_{40}H_{22}N_2O_2$ = 562.63) |
| P-45 | m/z = 648.23 ($C_{47}H_{28}N_4$ = 648.77) | P-46 | m/z = 621.22 ($C_{46}H_{27}N_3$ = 621.74) |
| P-47 | m/z = 546.18 ($C_{39}H_{22}N_4$ = 546.63) | P-48 | m/z = 760.26 ($C_{56}H_{32}N_4$ = 760.90) |
| P-49 | m/z = 773.28 ($C_{58}H_{35}N_3$ = 773.94) | P-50 | m/z = 829.26 ($C_{60}H_{35}N_3S$ = 830.02) |
| P-51 | m/z = 572.23 ($C_{43}H_{28}N_2$ = 572.71) | P-52 | m/z = 556.19 ($C_{42}H_{24}N_2$ = 556.67) |
| P-53 | m/z = 606.21 ($C_{46}H_{26}N_2$ = 606.73) | P-54 | m/z = 504.16 ($C_{38}H_{20}N_2$ = 504.59) |
| P-55 | m/z = 621.22 ($C_{46}H_{27}N_3$ = 621.74) | P-56 | m/z = 546.17 ($C_{40}H_{22}N_2O$ = 546.63) |
| P-57 | m/z = 643.21 ($C_{46}H_{21}D_5N_2S$ = 643.82) | P-58 | m/z = 532.19 ($C_{40}H_{24}N_2$ = 532.65) |
| P-59 | m/z = 682.24 ($C_{52}H_{30}N_2$ = 682.83) | P-60 | m/z = 584.20 ($C_{42}H_{24}N_4$ = 584.68) |
| P-61 | m/z = 710.25 ($C_{51}H_{30}N_4$ = 710.84) | P-62 | m/z = 584.20 ($C_{42}H_{24}N_4$ = 584.68) |
| P-63 | m/z = 610.22 ($C_{44}H_{26}N_4$ = 610.72) | P-64 | m/z = 875.30 ($C_{64}H_{37}N_5$ = 876.04) |
| P-65 | m/z = 611.21 ($C_{43}H_{25}N_5$ = 611.71) | P-66 | m/z = 761.26 ($C_{55}H_{31}N_5$ = 761.89) |
| P-67 | m/z = 640.17 ($C_{44}H_{24}N_4S$ = 640.76) | P-68 | m/z = 690.19 ($C_{48}H_{26}N_4S$ = 690.82) |
| P-69 | m/z = 624.20 ($C_{44}H_{34}N_4O$ = 624.70) | P-70 | m/z = 725.22 ($C_{51}H_{27}N_5O$ = 725.81) |
| P-71 | m/z = 584.20 ($C_{42}H_{24}N_4$ = 584.68) | P-72 | m/z = 589.25 ($C_{43}H_{31}N_3$ = 589.74) |
| P-73 | m/z = 608.23 ($C_{46}H_{28}N_2$ = 608.74) | P-74 | m/z = 608.23 ($C_{46}H_{28}N_2$ = 608.74) |

TABLE 3-continued

| Compound | FD-MS | Compound | FD-MS |
|---|---|---|---|
| P-75 | m/z = 584.20 ($C_{42}H_{24}N_4$ = 584.68) | P-76 | m/z = 584.20 ($C_{42}H_{24}N_4$ = 584.68) |
| P-77 | m/z = 634.22 ($C_{46}H_{26}N_4$ = 634.74) | P-78 | m/z = 610.22 ($C_{44}H_{26}N_4$ = 610.72) |
| P-79 | m/z = 660.23 ($C_{48}H_{28}N_4$ = 660.78) | P-80 | m/z = 611.21 ($C_{43}H_{25}N_5$ = 611.71) |
| P-81 | m/z = 661.23 ($C_{47}H_{27}N_5$ = 661.77) | P-82 | m/z = 640.17 ($C_{44}H_{24}N_4S$ = 640.76) |
| P-83 | m/z = 624.20 ($C_{44}H_{24}N_4O$ = 624.70) | P-84 | m/z = 842.28 ($C_{59}H_{34}N_6O$ = 842.96) |
| P-85 | m/z = 584.20 ($C_{42}H_{24}N_4$ = 584.68) | P-86 | m/z = 584.20 ($C_{42}H_{24}N_4$ = 584.68) |
| P-87 | m/z = 610.22 ($C_{44}H_{26}N_4$ = 610.72) | P-88 | m/z = 611.21 ($C_{43}H_{25}N_5$ = 611.71) |
| P-89 | m/z = 640.17 ($C_{44}H_{24}N_4S$ = 640.76) | P-90 | m/z = 624.20 ($C_{44}H_{24}N_4O$ = 624.70) |
| P-91 | m/z = 724.26 ($C_{53}H_{32}N_4$ = 724.87) | P-92 | m/z = 698.25 ($C_{51}H_{30}N_4$ = 698.83) |
| P-93 | m/z = 628.21 ($C_{44}H_{24}5FN_4$ = 628.71) | P-94 | m/z = 709.25 ($C_{53}H_{31}N_3$ = 709.85) |
| P-95 | m/z = 639.25 ($C_{46}H_{21}D_5N_4$ = 639.77) | | |

Fabrication and Evaluation of Organic Electroluminescent Element

[Example 1] Red OLED (Host)

After vacuum-depositing $N^1$-(naphthalen-2-yl)-$N^4$,$N^4$-bis(4-(naphthalen-2-yl(phenyl)amino)phenyl)-$N^1$-phenylbenzene-1,4-diamine (hereinafter, "2-TNATA") on an ITO layer (anode) formed on a glass substrate to form a hole injection layer with a thickness of 60 nm, a hole transport layer with a thickness of 60 nm was formed by vacuum-depositing 4,4-bis[N-(1-naphthyl)-N-phenylamino]bipheny (hereinafter, "NPD") on the hole injection layer.

Next, the compound P-1 of the present invention as a host material and bis-(1-phenylisoquinolyl)iridium(III)acetylacetonate (hereinafter, "(piq)$_2$Ir(acac)") as a dopant material in a weight ratio of 95:5 were deposited on the hole transport layer to form a light emitting layer with a thickness of 30 nm.

Subsequently, (1,1'-bisphenyl-4-olato)bis(2-methyl-8-quinolinolato)aluminum (hereinafter, "BAlq") was vacuum-deposited to a thickness of 10 nm on the light emitting layer to form a hole blocking layer, and tris(8-quinolinolato)aluminum (hereinafter, "Alq$_3$") was vacuum-deposited to a thickness of 40 nm on the hole blocking layer to form a an electron transport layer.

Next, LiF was deposited to a thickness of 0.2 nm to form an electron injection layer, and then Al was deposited to a thickness of 150 to form a cathode.

[Example 2] to [Example 32]

The OLEDs were fabricated in the same manner as described in Example 1 except that the compound of the present invention described in the following Table 4, instead of the compound P-1 of the present invention, was used as host material of a light emitting layer.

[Comparative Example 1] and [Comparative Example 2]

The OLEDs were fabricated in the same manner as described in Example 1 except that one of the following Comparative compounds 1 or 2, instead of the compound P-1 of the present invention, was used as host material of a light emitting layer.

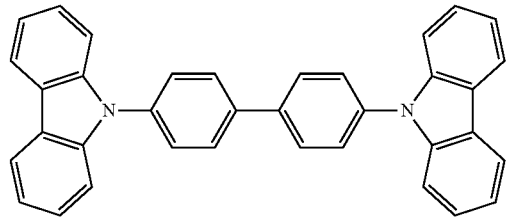
<Comp. compd 1>

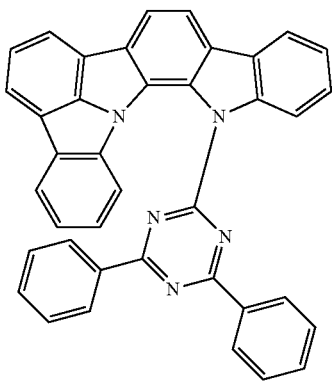
<Comp. compd 2>

Electroluminescence (EL) characteristics were measured with a PR-650 (Photoresearch) by applying a forward bias DC voltage to the OLEDs prepared in Examples 1 to 32 of the present invention and Comparative Examples 1 and 2. And, the T95 life time was measured using a life time measuring apparatus manufactured by ms science Inc. at reference brightness of 2500 cd/m$^2$. The measurement results are shown in Tables 4 below.

TABLE 4

| | Compound | Voltage (V) | Current Density (mA/cm²) | Brightness (cd/m²) | Efficiency (cd/A) | Lifetime T(95) | CIE X | CIE Y |
|---|---|---|---|---|---|---|---|---|
| comp. Ex(1) | comp. Com 1 | 6.2 | 34.7 | 2500 | 7.2 | 69.1 | 0.66 | 0.32 |
| comp. Ex(2) | comp. Com 2 | 5.4 | 26.3 | 2500 | 9.5 | 96.8 | 0.66 | 0.32 |
| Ex. (1) | Com. P-1 | 4.9 | 17.1 | 2500 | 14.6 | 116.8 | 0.66 | 0.34 |
| Ex. (2) | Com. P-2 | 4.9 | 17.2 | 2500 | 14.5 | 116.5 | 0.66 | 0.34 |
| Ex. (3) | Com. P-7 | 4.8 | 16.2 | 2500 | 15.4 | 117.9 | 0.66 | 0.33 |
| Ex. (4) | Com. P-8 | 4.8 | 15.9 | 2500 | 15.7 | 118.3 | 0.66 | 0.33 |
| Ex. (5) | Com. P-10 | 4.8 | 15.7 | 2500 | 15.9 | 118.6 | 0.66 | 0.34 |
| Ex. (6) | Com. P-11 | 4.8 | 14.8 | 2500 | 16.9 | 119.7 | 0.66 | 0.34 |
| Ex. (7) | Com. P-13 | 4.9 | 16.3 | 2500 | 15.3 | 117.7 | 0.66 | 0.34 |
| Ex. (8) | Com. P-15 | 4.9 | 17.2 | 2500 | 14.5 | 116.2 | 0.66 | 0.33 |
| Ex. (9) | Com. P-22 | 4.9 | 17.5 | 2500 | 14.3 | 115.7 | 0.66 | 0.34 |
| Ex. (10) | Com. P-23 | 5.0 | 17.7 | 2500 | 14.1 | 113.9 | 0.66 | 0.33 |
| Ex. (11) | Com. P-24 | 4.9 | 17.4 | 2500 | 14.4 | 115.3 | 0.66 | 0.34 |
| Ex. (12) | Com. P-29 | 5.1 | 22.7 | 2500 | 11.0 | 110.9 | 0.66 | 0.33 |
| Ex. (13) | Com. P-32 | 4.8 | 15.2 | 2500 | 16.4 | 119.4 | 0.66 | 0.34 |
| Ex. (14) | Com. P-34 | 4.9 | 16.4 | 2500 | 15.2 | 117.6 | 0.66 | 0.33 |
| Ex. (15) | Com. P-37 | 4.8 | 15.5 | 2500 | 16.1 | 119.2 | 0.66 | 0.34 |
| Ex. (16) | Com. P-38 | 4.9 | 16.8 | 2500 | 14.9 | 117.1 | 0.66 | 0.33 |
| Ex. (17) | Com. P-39 | 4.9 | 16.7 | 2500 | 15.0 | 117.4 | 0.66 | 0.34 |
| Ex. (18) | Com. P-41 | 5.0 | 18.1 | 2500 | 13.8 | 113.7 | 0.66 | 0.33 |
| Ex. (19) | Com. P-45 | 5.0 | 18.5 | 2500 | 13.5 | 113.4 | 0.66 | 0.34 |
| Ex. (20) | Com. P-46 | 5.0 | 19.1 | 2500 | 13.1 | 113.2 | 0.66 | 0.34 |
| Ex. (21) | Com. P-49 | 5.1 | 23.4 | 2500 | 10.7 | 110.8 | 0.66 | 0.33 |
| Ex. (22) | Com. P-57 | 4.9 | 17.0 | 2500 | 14.7 | 117.0 | 0.66 | 0.34 |
| Ex. (23) | Com. P-58 | 5.1 | 22.5 | 2500 | 11.1 | 111.2 | 0.66 | 0.34 |
| Ex. (24) | Com. P-62 | 5.0 | 17.0 | 2500 | 14.7 | 114.7 | 0.66 | 0.33 |
| Ex. (25) | Com. P-67 | 5.0 | 17.4 | 2500 | 14.4 | 114.3 | 0.66 | 0.33 |
| Ex. (26) | Com. P-74 | 5.1 | 23.6 | 2500 | 10.6 | 110.6 | 0.66 | 0.33 |
| Ex. (27) | Com. P-76 | 5.1 | 19.5 | 2500 | 12.8 | 112.7 | 0.66 | 0.33 |
| Ex. (28) | Com. P-85 | 5.1 | 20.0 | 2500 | 12.5 | 112.5 | 0.66 | 0.34 |
| Ex. (29) | Com. P-88 | 5.1 | 20.5 | 2500 | 12.2 | 112.2 | 0.66 | 0.34 |
| Ex. (30) | Com. P-89 | 5.1 | 21.2 | 2500 | 11.8 | 112.1 | 0.66 | 0.34 |
| Ex. (31) | Com. P-94 | 5.1 | 24.3 | 2500 | 10.3 | 110.2 | 0.66 | 0.33 |
| Ex. (32) | Com. P-95 | 5.1 | 21.9 | 2500 | 11.4 | 111.6 | 0.66 | 0.34 |

As can be seen from the results of Table 4, the characteristics of the element employing the compound according to an embodiment of the present invention as the phosphorescent host material of the light emitting layer are significantly improved, compared to the element employing Comparative Compound 1 or 2.

In more detail, the characteristics of element employing Comparative compound 2 having indolocarbazole as the main skeleton as host material is improved, compared to the element employing CBP (Comparative Compound 1) being a general host material, and driving voltage, efficiency and life time are improved when the compound of the present invention is used as a host material than Comparative Compound 2.

As can be seen from Table 5 below, the middle ring in Comparative Compound 2 is a benzene ring, but the compound of the present invention has a difference in that the middle ring is naphthalene. Due to this difference, the properties of both compounds are significantly different. Comparing the properties of Comparative Compound 2 and Compound P-32 of the present invention, it can be seen that there is a difference in the energy level of the compound, in particular, HOMO level and T1 level.

Therefore, in the case of the compound of the present invention, as one more benzene is introduced (fused) into the benzene in middle, the T1 value of the compound is lowered, and the charge transfer from the host to the dopant becomes smooth, thereby increasing the charge balance in the light emitting layer. As a result, it seems that the characteristics of the element are improved.

TABLE 5

| | comp.Com 2 | P-32 |
|---|---|---|
| Structure | | |
| HOMO (eV) | −5.19 | −5.24 |
| LUMO (eV) | −1.98 | −1.97 |
| Eg (eV) | 3.21 | 3.27 |
| T1 (eV) | 2.46 | 2.24 |

Although the exemplary embodiments of the present invention have been described for illustrative purposes, those skilled in the art to which the present invention pertains will be capable of various modifications without departing from the essential characteristics of the present invention. Therefore, the embodiment disclosed herein is intended to illustrate the scope of the technical idea of the present invention, and the spirit and scope of the present invention are not limited by the embodiments. The scope of the present invention shall be construed on the basis of the accompanying claims, and it shall be construed that all of the technical ideas included within the scope equivalent to the claims belong to the present invention.

The invention claimed is:

1. A compound of Formula 3:

[Formula 3]

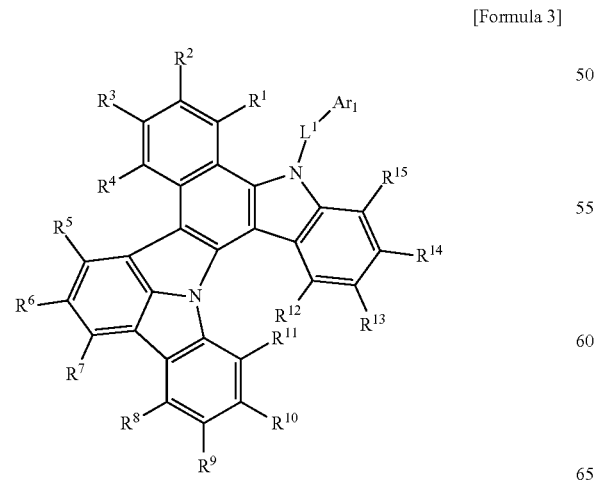

wherein:
$R^1$ to $R^{15}$ are each independently selected from the group consisting of hydrogen, deuterium, halogen, a $C_6$-$C_{60}$ aryl group, a fluorenyl group, a $C_2$-$C_{60}$ heterocyclic group containing at least one heteroatom of O, N, S, Si, and P, a $C_3$-$C_{60}$ aliphatic ring, a fused ring group formed by a $C_3$-$C_{60}$ aliphatic ring with a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group and a $C_6$-$C_{30}$ aryloxy group, and adjacent groups together may be bonded to each other to form a ring selected from the group consisting of a $C_6$-$C_{60}$ aromatic ring, a $C_2$-$C_{60}$ heterocycle, a $C_3$-$C_{60}$ aliphatic ring and a combination thereof, $L^1$ is selected from the group consisting of a single bond, a $C_6$-$C_{60}$ arylene group, a fluorenylene group, a $C_2$-$C_{60}$ heterocyclic group containing at least one heteroatom of O, N, S, Si, and P, a $C_3$-$C_{60}$ aliphatic ring, and a fused ring group formed by a $C_3$-$C_{60}$ aliphatic ring with a $C_6$-$C_{60}$ aromatic ring, $Ar_1$ is selected from the group consisting of a $C_6$-$C_{60}$ aryl group, a fluorenyl group, a $C_2$-$C_{60}$ heterocyclic group containing at least one heteroatom of O, N, S, Si, and P, a $C_3$-$C_{60}$ aliphatic ring, a fused ring group formed by a $C_3$-$C_{60}$ aliphatic ring with a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxy group and -L'-N($R_a$)($R_b$), L' is selected from the group consisting of a single bond, a $C_6$-$C_{60}$ arylene group, a fluorenylene group, a $C_2$-$C_{60}$ heterocyclic group containing at least one heteroatom of O, N, S, Si, and P, a $C_3$-$C_{60}$ aliphatic ring, and a fused ring group formed by a $C_3$-$C_{60}$ aliphatic ring with a $C_6$-$C_{60}$ aromatic ring, $R_a$ and $R_b$ are each independently selected from the group consisting of hydrogen, a $C_6$-$C_{60}$ aryl group, a fluorenyl group, a $C_2$-$C_{60}$ heterocyclic group containing at least one heteroatom of O, N, S, Si, and P, and a fused ring group formed by a $C_3$-$C_{60}$ aliphatic ring with a $C_6$-$C_{60}$ aromatic ring, and the above $R^1$ to $R^{15}$, $L^1$, $Ar_1$, a ring formed by adjacent groups among $R^1$ to $R^{15}$, L', $R_a$ and $R_b$ may be each optionally substituted with one or more substituents selected from the group consisting of deuterium, halogen, a silane group unsubstituted or substituted with a $C_1$-$C_{20}$ alkyl group or a $C_6$-$C_{20}$ aryl group, a siloxane group, a boron group, a germanium group, a cyano group, a nitro group, a phosphine oxide group unsubstituted or substituted with a $C_1$-$C_{20}$ alkyl group or a $C_6$-$C_{20}$ aryl group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom of O, N, S, Si, and P, a $C_3$-$C_{20}$ cycloalkyl group, a fused ring group formed by a $C_3$-$C_{60}$ aliphatic ring with a $C_6$-$C_{60}$ aromatic ring, a $C_7$-$C_{20}$ arylalkyl group, a $C_8$-$C_{20}$) arylalkenyl group and -L'-N($R_a$)($R_b$).

2. An organic electric element comprising a first electrode, a second electrode, and an organic material layer formed between the first electrode and the second electrode, wherein the organic material layer comprises a single compound or a mixture comprising two or more compounds represented by Formula 3 of claim 1.

3. The organic electric element of claim 2, wherein the organic material layer comprises at least one of a hole injection layer, a hole transport layer, an emission-auxiliary layer, a light emitting layer, an electron transport auxiliary layer, an electron transport layer and an electron injection layer.

4. The organic electric element of claim 3, wherein the light emitting layer comprises the compound or the mixture.

5. The organic electric element of claim 2, wherein the organic material layer is formed by a process of spin coating, nozzle printing, inkjet printing, slot coating, dip coating or roll-to-roll.

6. The organic electric element of claim 2, wherein the organic electric element further comprises a layer for improving luminous efficiency formed on one side of sides of the first electrode or the second electrode, and the one side is not facing the organic material layer.

7. An electronic device comprising a display device and a control unit for driving the display device, wherein the display device comprises the organic electric element of claim 2.

8. The electronic device of claim 7, wherein the organic electric element is selected from the group consisting of an organic electroluminescent element, an organic solar cell, an organic photo conductor, an organic transistor, an element for monochromatic illumination and element for quantum dot display.

9. A compound selected from the group consisting of the following compounds:

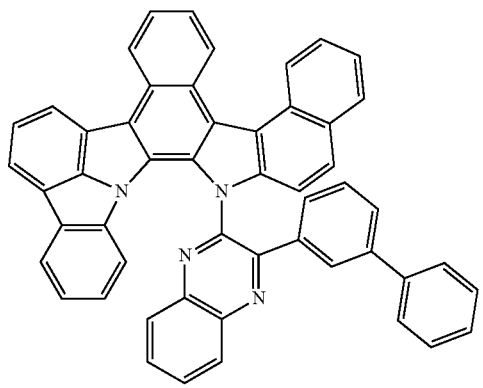

P-27

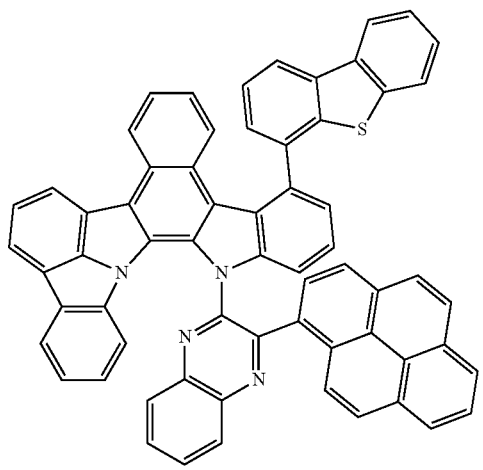

P-29

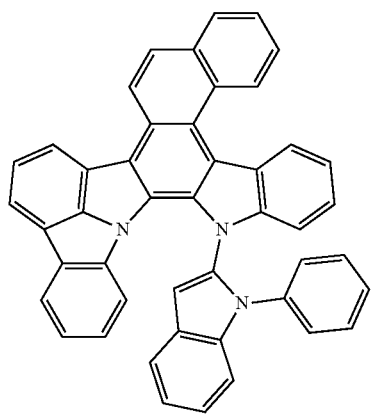

P-46

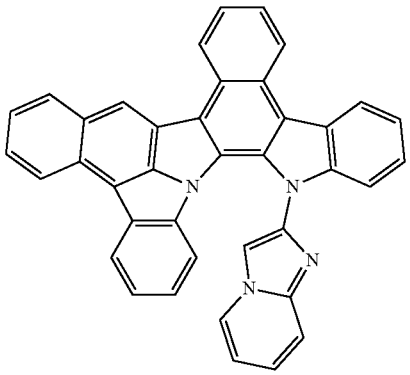

P-47

P-48
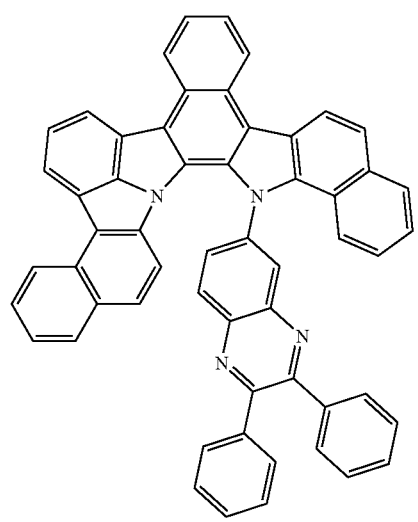
P-49
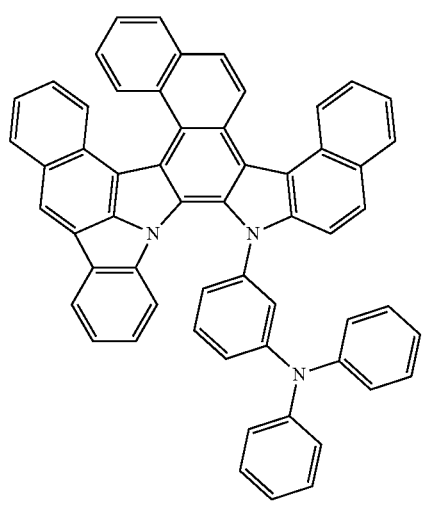
P-50
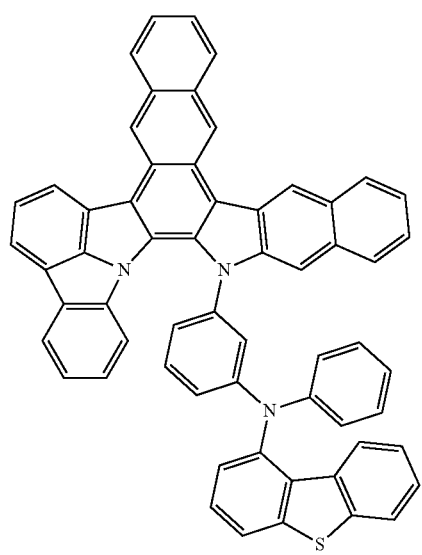
P-57
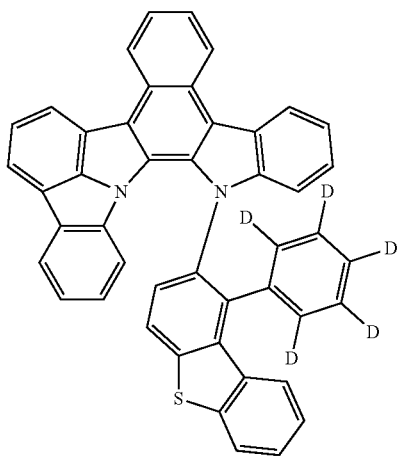
P-58
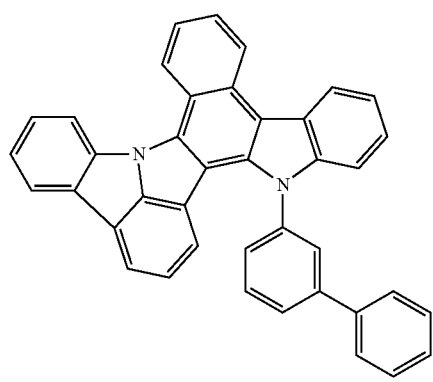
P-59
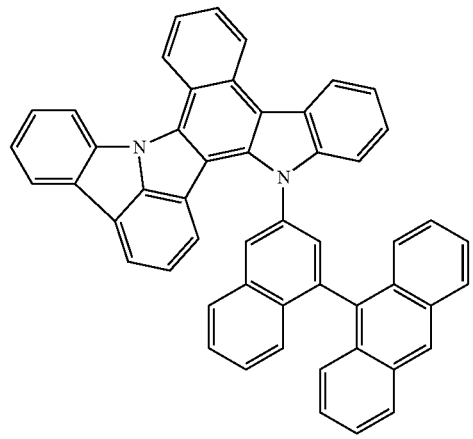
P-60
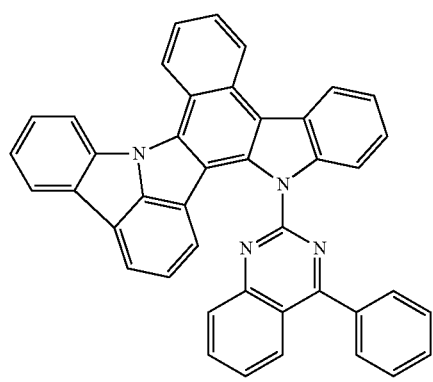

P-61
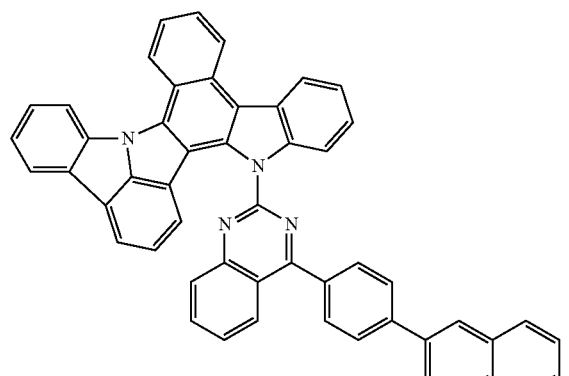
P-62
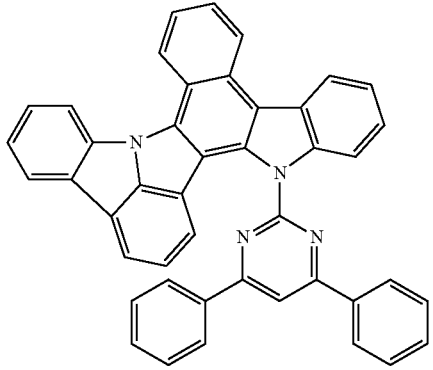
P-65
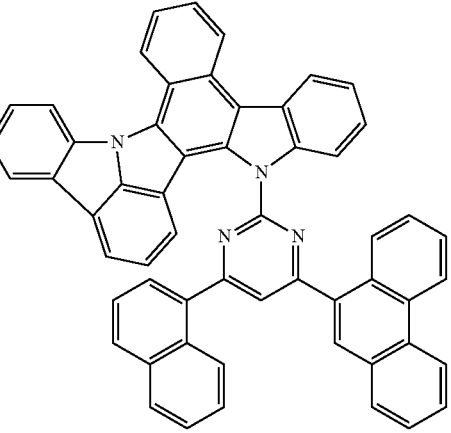
P-66
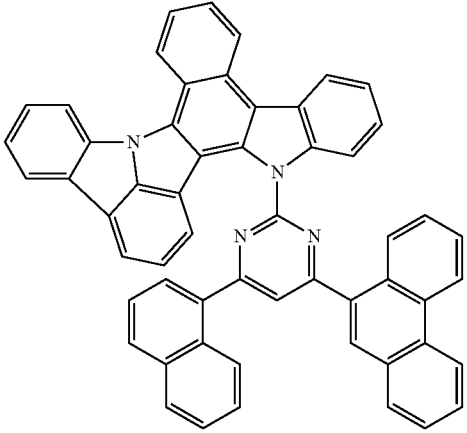
P-63
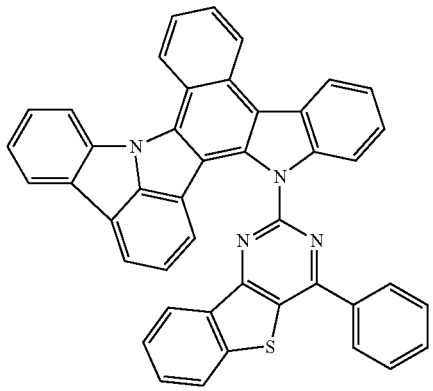
P-67
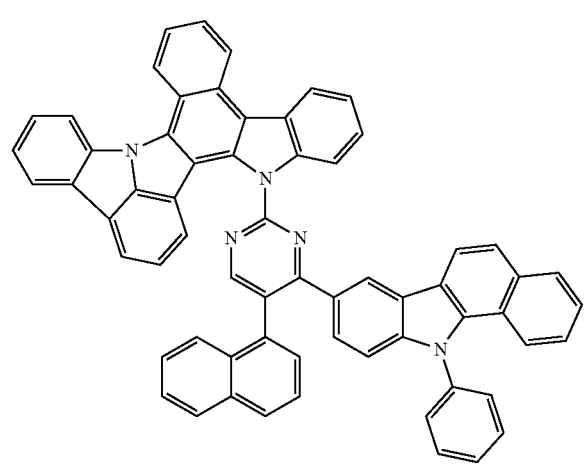
P-64
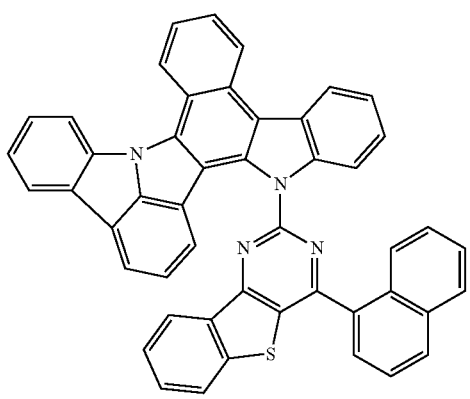
P-68

-continued
P-69
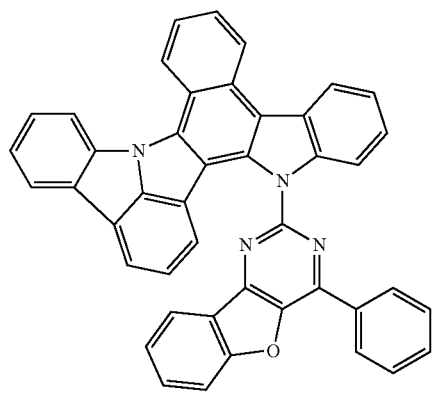
P-70
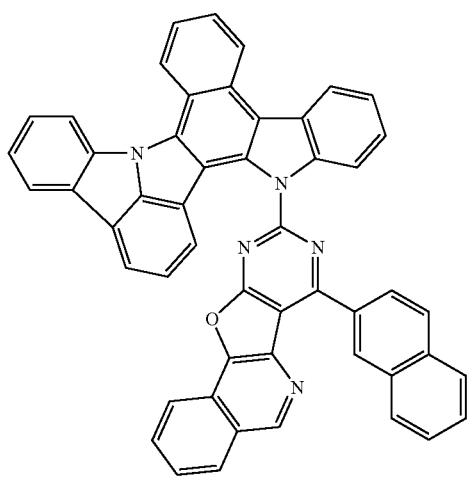
P-71
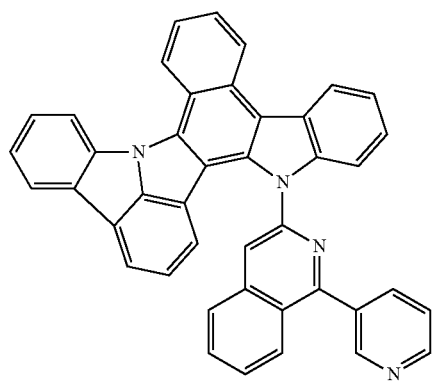
P-72
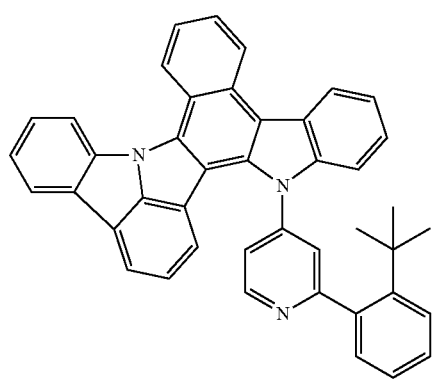
-continued
P-73
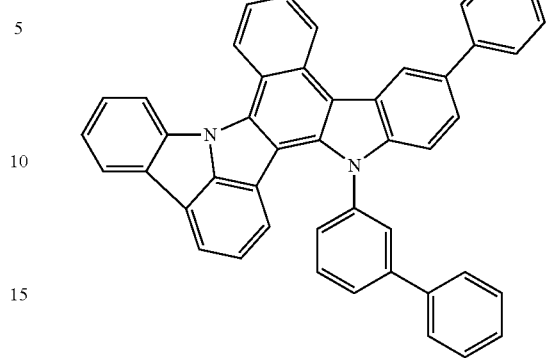
P-74
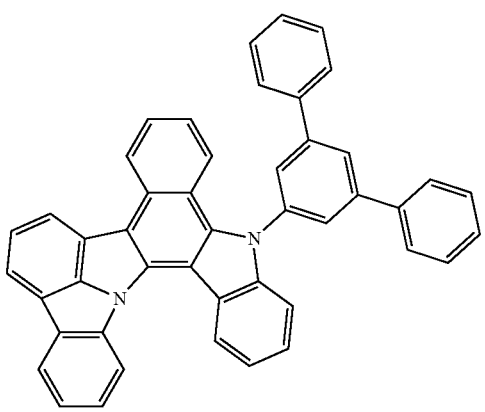
P-75
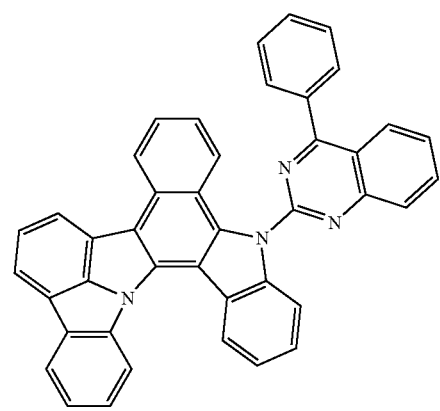
P-76
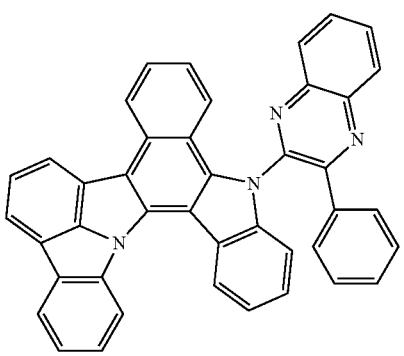

-continued
P-77
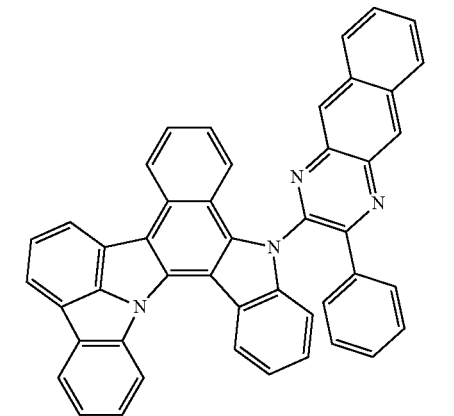
P-78
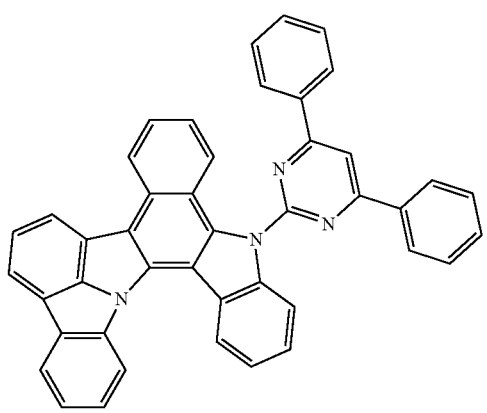
P-79
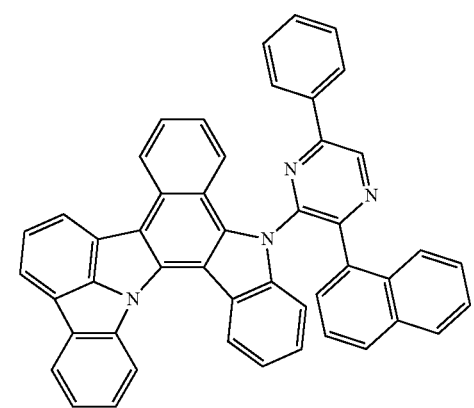
-continued
P-80
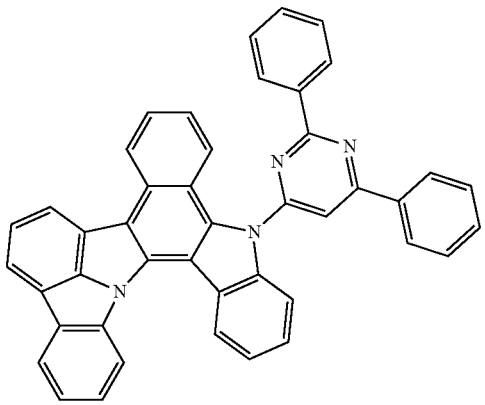
P-81
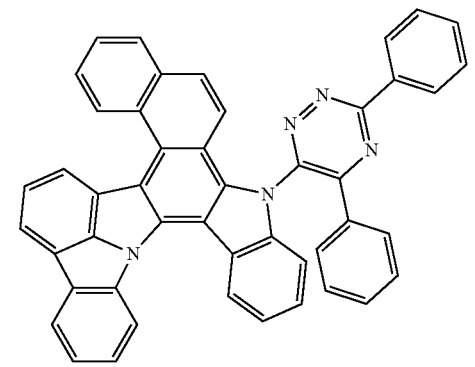
P-82
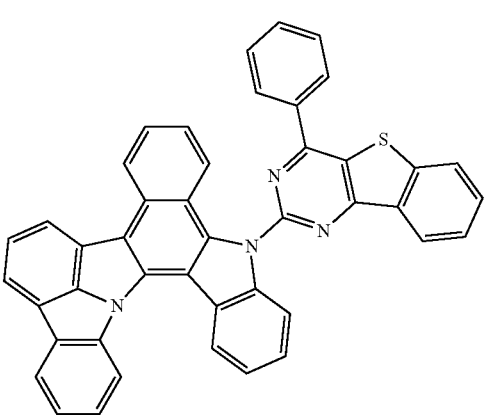
P-83
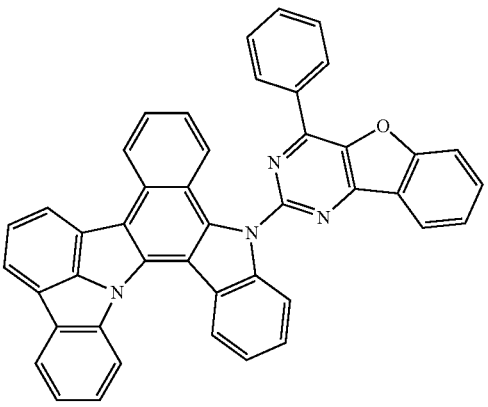

P-84
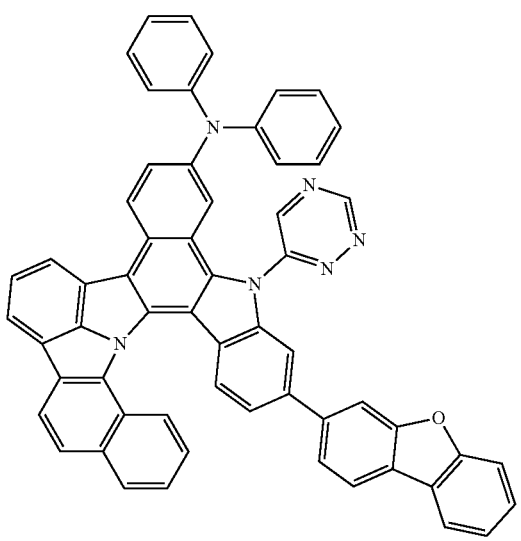
P-85
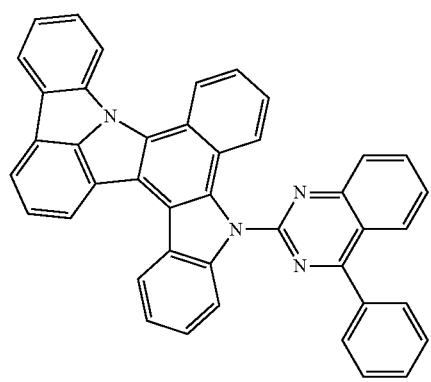
P-86
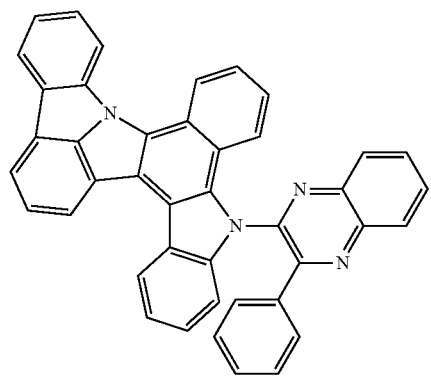
P-87
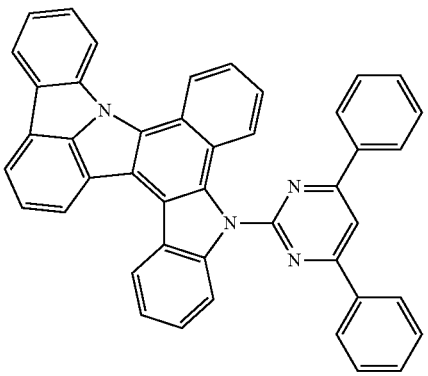
P-88
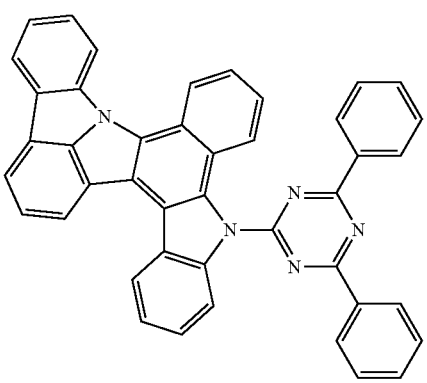
P-89
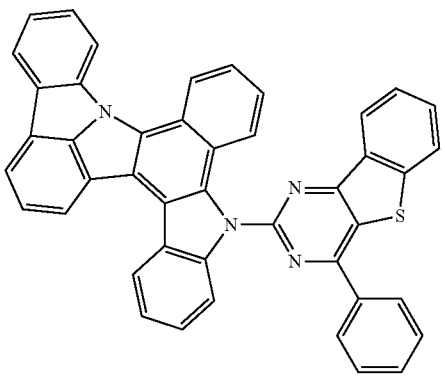
P-90
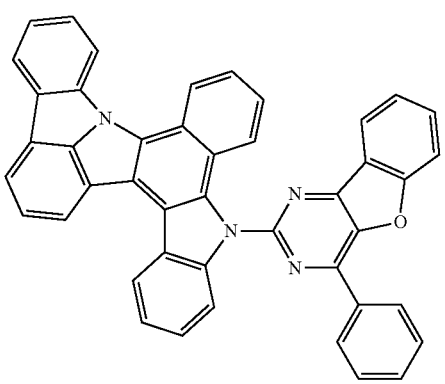

-continued

P-91
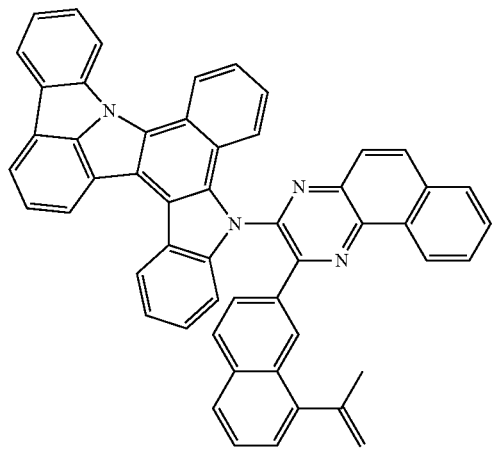

P-92
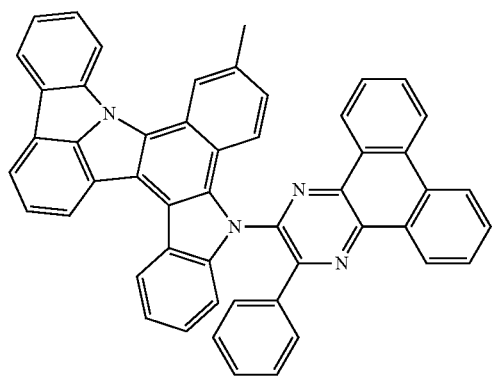

P-93
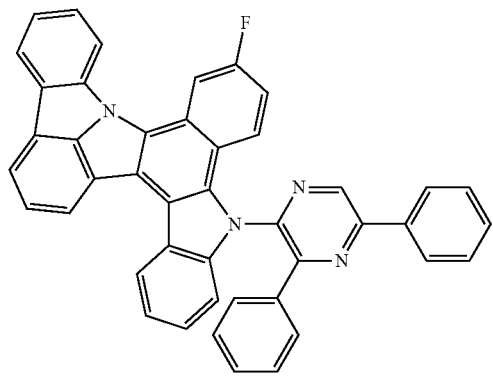

-continued

P-94
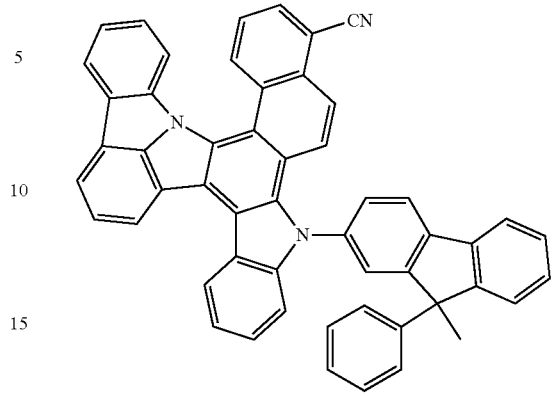

P-95
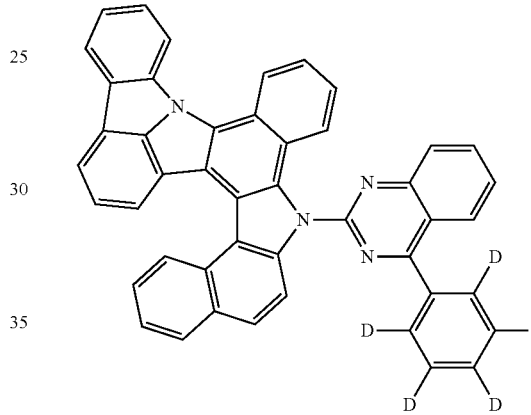

10. An organic electric element comprising a first electrode, a second electrode, and an organic material layer formed between the first electrode and the second electrode, wherein the organic material layer comprises a compound of claim 9 as a single compound or a mixture of two or more compounds.

11. An electronic device comprising a display device and a control unit for driving the display device, wherein the display device comprises the organic electric element of claim 10.

* * * * *